United States Patent
Yates et al.

(10) Patent No.: US 8,459,525 B2
(45) Date of Patent: Jun. 11, 2013

(54) MOTORIZED SURGICAL CUTTING AND FASTENING INSTRUMENT HAVING A MAGNETIC DRIVE TRAIN TORQUE LIMITING DEVICE

(75) Inventors: David C. Yates, West Chester, OH (US); Thomas W. Huitema, Cincinnati, OH (US)

(73) Assignee: Ethicon Endo-Sugery, Inc., Cincinnati, OH (US)

( * ) Notice: Subject to any disclaimer, the term of this patent is extended or adjusted under 35 U.S.C. 154(b) by 1385 days.

(21) Appl. No.: 12/031,542

(22) Filed: Feb. 14, 2008

(65) Prior Publication Data
US 2013/0041371 A1  Feb. 14, 2013

(51) Int. Cl.
*A61B 17/068* (2006.01)

(52) U.S. Cl.
USPC ....... 227/180.1; 227/19; 227/176.1; 173/178; 606/139; 606/219

(58) Field of Classification Search
USPC ............... 227/19, 175.1, 176.1, 175.2, 180.1, 227/178.1; 173/178, 176; 606/139, 219
See application file for complete search history.

(56) References Cited

U.S. PATENT DOCUMENTS

| | | | |
|---|---|---|---|
| 66,052 A | 6/1867 | Smith | |
| 662,587 A | 11/1900 | Blake | |
| 951,393 A | 3/1910 | Hahn | |
| 2,037,727 A | 4/1936 | La Chapelle | |
| 2,132,295 A | 10/1938 | Hawkins | |
| 2,161,632 A | 6/1939 | Nattenheimer | |
| 2,211,117 A | 8/1940 | Hess | |
| 2,214,870 A | 9/1940 | West | |
| 2,441,096 A | 5/1948 | Happe | |
| 2,526,902 A | 10/1950 | Rublee | |
| 2,674,149 A | 4/1954 | Benson | |
| 2,804,848 A | 9/1957 | O'Farrell et al. | |
| 2,808,482 A | 10/1957 | Zanichkowsky et al. | |
| 2,853,074 A | 9/1958 | Olson | |
| 3,032,769 A | 5/1962 | Palmer | |
| 3,075,062 A | 1/1963 | Iaccarino | |
| 3,078,465 A | 2/1963 | Bobrov | |
| 3,166,072 A | 1/1965 | Sullivan, Jr. | |
| 3,266,494 A | 8/1966 | Brownrigg et al. | |

(Continued)

FOREIGN PATENT DOCUMENTS

| CA | 2458946 A1 | 3/2003 |
|---|---|---|
| CA | 2414274 A1 | 1/2006 |

(Continued)

OTHER PUBLICATIONS

D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).

(Continued)

*Primary Examiner* — Scott A. Smith

(57) ABSTRACT

A surgical cutting and fastening instrument. The instrument comprises an end effector and a shaft connected to the end effector. The shaft comprises a drive train for powering the end effector. The instrument also comprises an electric, DC motor connected to the drive train for powering the drive train. The instrument also comprises a torque-limiting device connected between to an output pole of the motor and an input pole of the drive train.

15 Claims, 39 Drawing Sheets

U.S. PATENT DOCUMENTS

| | | |
|---|---|---|
| 3,269,630 A | 8/1966 | Fleischer |
| 3,357,296 A | 12/1967 | Lefever |
| 3,490,675 A | 1/1970 | Green et al, |
| 3,551,987 A | 1/1971 | Wilkinson |
| 3,598,943 A | 8/1971 | Barrett |
| 3,643,851 A | 2/1972 | Green et al. |
| 3,662,939 A | 5/1972 | Bryan |
| 3,717,294 A | 2/1973 | Green |
| 3,734,207 A | 5/1973 | Fishbein |
| 3,740,994 A | 6/1973 | DeCarlo, Jr. |
| 3,744,495 A | 7/1973 | Johnson |
| 3,746,002 A | 7/1973 | Haller |
| 3,751,902 A | 8/1973 | Kingsbury et al. |
| 3,819,100 A | 6/1974 | Noiles et al. |
| 3,821,919 A | 7/1974 | Knohl |
| 3,885,491 A | 5/1975 | Curtis |
| 3,892,228 A | 7/1975 | Mitsui |
| 3,894,174 A | 7/1975 | Cartun |
| 3,940,844 A | 3/1976 | Colby et al. |
| RE28,932 E | 8/1976 | Noiles et al. |
| 4,060,089 A | 11/1977 | Noiles |
| 4,129,059 A | 12/1978 | Van Eck |
| 4,213,562 A | 7/1980 | Garrett et al. |
| 4,250,436 A | 2/1981 | Weissman |
| 4,261,244 A | 4/1981 | Becht et al. |
| 4,272,662 A | 6/1981 | Simpson |
| 4,275,813 A | 6/1981 | Noiles |
| 4,289,133 A | 9/1981 | Rothfuss |
| 4,305,539 A | 12/1981 | Korolkov et al. |
| 4,317,451 A | 3/1982 | Cerwin et al. |
| 4,321,002 A | 3/1982 | Froehlich |
| 4,331,277 A | 5/1982 | Green |
| 4,340,331 A | 7/1982 | Savino |
| 4,347,450 A | 8/1982 | Colligan |
| 4,349,028 A | 9/1982 | Green |
| 4,353,371 A | 10/1982 | Cosman |
| 4,379,457 A | 4/1983 | Gravener et al. |
| 4,380,312 A | 4/1983 | Landrus |
| 4,383,634 A | 5/1983 | Green |
| 4,396,139 A | 8/1983 | Hall et al. |
| 4,402,445 A | 9/1983 | Green |
| 4,408,692 A | 10/1983 | Sigel et al. |
| 4,415,112 A | 11/1983 | Green |
| 4,428,376 A | 1/1984 | Mericle |
| 4,429,695 A | 2/1984 | Green |
| 4,434,796 A | 3/1984 | Karapetian et al. |
| 4,442,964 A | 4/1984 | Becht |
| 4,451,743 A | 5/1984 | Suzuki et al. |
| 4,454,887 A | 6/1984 | Krüger |
| 4,467,805 A | 8/1984 | Fukuda |
| 4,475,679 A | 10/1984 | Fleury, Jr. |
| 4,485,816 A | 12/1984 | Krumme |
| 4,489,875 A | 12/1984 | Crawford et al. |
| 4,500,024 A | 2/1985 | DiGiovanni et al. |
| 4,505,273 A | 3/1985 | Braun et al. |
| 4,505,414 A | 3/1985 | Filipi |
| 4,506,671 A | 3/1985 | Green |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,453 A | 7/1985 | Green |
| 4,548,202 A | 10/1985 | Duncan |
| 4,565,189 A | 1/1986 | Mabuchi |
| 4,566,620 A | 1/1986 | Green et al. |
| 4,573,469 A | 3/1986 | Golden et al. |
| 4,573,622 A | 3/1986 | Green et al. |
| 4,576,167 A | 3/1986 | Noiles |
| 4,580,712 A | 4/1986 | Green |
| 4,589,416 A | 5/1986 | Green |
| 4,591,085 A | 5/1986 | Di Giovanni |
| 4,604,786 A | 8/1986 | Howie, Jr. |
| 4,605,001 A | 8/1986 | Rothfuss et al. |
| 4,606,343 A | 8/1986 | Conta et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| 4,619,262 A | 10/1986 | Taylor |
| 4,629,107 A | 12/1986 | Fedotov et al. |
| 4,632,290 A | 12/1986 | Green et al. |
| 4,633,874 A | 1/1987 | Chow et al. |
| 4,641,076 A | 2/1987 | Linden |
| 4,646,722 A | 3/1987 | Silverstein et al. |
| 4,655,222 A | 4/1987 | Florez et al. |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,671,445 A | 6/1987 | Barker et al. |
| 4,676,245 A | 6/1987 | Fukuda |
| 4,693,248 A | 9/1987 | Failla |
| 4,709,120 A | 11/1987 | Pearson |
| 4,715,520 A | 12/1987 | Roehr, Jr. et al. |
| 4,719,917 A | 1/1988 | Barrows et al. |
| 4,728,020 A | 3/1988 | Green et al. |
| 4,728,876 A | 3/1988 | Mongeon et al. |
| 4,729,260 A | 3/1988 | Dudden |
| 4,741,336 A | 5/1988 | Failla et al. |
| 4,752,024 A | 6/1988 | Green et al. |
| 4,754,909 A | 7/1988 | Barker et al. |
| 4,767,044 A | 8/1988 | Green |
| 4,777,780 A | 10/1988 | Holzwarth |
| 4,787,387 A | 11/1988 | Burbank, III et al. |
| 4,790,225 A | 12/1988 | Moody et al. |
| 4,805,617 A | 2/1989 | Bedi et al. |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,844,068 A | 7/1989 | Arata et al. |
| 4,869,414 A | 9/1989 | Green et al. |
| 4,869,415 A | 9/1989 | Fox |
| 4,880,015 A | 11/1989 | Nierman |
| 4,890,613 A | 1/1990 | Golden et al. |
| 4,892,244 A | 1/1990 | Fox et al. |
| 4,915,100 A | 4/1990 | Green |
| 4,930,503 A | 6/1990 | Pruitt |
| 4,932,960 A | 6/1990 | Green et al. |
| 4,938,408 A | 7/1990 | Bedi et al. |
| 4,941,623 A | 7/1990 | Pruitt |
| 4,944,443 A | 7/1990 | Oddsen et al. |
| 4,955,959 A | 9/1990 | Tompkins et al. |
| 4,978,049 A | 12/1990 | Green |
| 4,986,808 A | 1/1991 | Broadwin et al. |
| 4,988,334 A | 1/1991 | Hornlein et al. |
| 5,002,553 A | 3/1991 | Shiber |
| 5,009,661 A | 4/1991 | Michelson |
| 5,014,899 A | 5/1991 | Presty et al. |
| 5,015,227 A | 5/1991 | Broadwin et al. |
| 5,027,834 A | 7/1991 | Pruitt |
| 5,031,814 A | 7/1991 | Tompkins et al. |
| 5,040,715 A | 8/1991 | Green et al. |
| 5,042,707 A | 8/1991 | Taheri |
| 5,061,269 A | 10/1991 | Muller |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,080,556 A | 1/1992 | Carreno |
| 5,083,695 A | 1/1992 | Foslien et al. |
| 5,084,057 A | 1/1992 | Green et al. |
| 5,088,580 A | 2/1992 | Grothe et al. |
| 5,088,979 A | 2/1992 | Filipi et al. |
| 5,088,997 A | 2/1992 | Delahuerga et al. |
| 5,094,247 A | 3/1992 | Hernandez et al. |
| 5,100,420 A | 3/1992 | Green et al. |
| 5,104,025 A | 4/1992 | Main et al. |
| 5,106,008 A | 4/1992 | Tompkins et al. |
| 5,111,987 A | 5/1992 | Moeinzadeh et al. |
| 5,116,349 A | 5/1992 | Aranyi |
| 5,129,570 A | 7/1992 | Schulze et al. |
| 5,137,198 A | 8/1992 | Nobis et al. |
| 5,139,513 A | 8/1992 | Segato |

| Patent Number | Date | Inventor |
|---|---|---|
| 5,141,144 A | 8/1992 | Foslien et al. |
| 5,156,315 A | 10/1992 | Green et al. |
| 5,156,614 A | 10/1992 | Green et al. |
| 5,158,567 A | 10/1992 | Green |
| D330,699 S | 11/1992 | Gill |
| 5,163,598 A | 11/1992 | Peters et al. |
| 5,171,247 A | 12/1992 | Hughett et al. |
| 5,171,249 A | 12/1992 | Stefanchik et al. |
| 5,188,111 A | 2/1993 | Yates et al. |
| 5,190,517 A | 3/1993 | Zieve et al. |
| 5,195,968 A | 3/1993 | Lundquist et al. |
| 5,197,648 A | 3/1993 | Gingold |
| 5,200,280 A | 4/1993 | Karasa |
| 5,205,459 A | 4/1993 | Brinkerhoff et al. |
| 5,207,697 A | 5/1993 | Carusillo et al. |
| 5,209,747 A | 5/1993 | Knoepfler |
| 5,211,649 A | 5/1993 | Kohler et al. |
| 5,217,457 A | 6/1993 | Delahuerga et al. |
| 5,217,478 A | 6/1993 | Rexroth |
| 5,219,111 A | 6/1993 | Bilotti et al. |
| 5,221,036 A | 6/1993 | Takase |
| 5,221,281 A | 6/1993 | Klicek |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| 5,234,447 A | 8/1993 | Kaster et al. |
| 5,236,440 A | 8/1993 | Hlavacek |
| 5,239,981 A | 8/1993 | Anapliotis |
| 5,240,163 A | 8/1993 | Stein et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,009 A | 11/1993 | Conners |
| 5,258,012 A | 11/1993 | Luscombe et al. |
| 5,259,366 A | 11/1993 | Reydel et al. |
| 5,260,637 A | 11/1993 | Pizzi |
| 5,263,629 A | 11/1993 | Trumbull et al. |
| 5,263,973 A | 11/1993 | Cook |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,323 A | 1/1994 | Schulze et al. |
| 5,275,608 A | 1/1994 | Forman et al. |
| 5,281,216 A | 1/1994 | Klicek |
| 5,282,806 A | 2/1994 | Haber et al. |
| 5,282,829 A | 2/1994 | Hermes |
| 5,297,714 A | 3/1994 | Kramer |
| 5,304,204 A | 4/1994 | Bregen |
| 5,307,976 A | 5/1994 | Olson et al. |
| 5,309,927 A | 5/1994 | Welch |
| 5,312,023 A | 5/1994 | Green et al. |
| 5,312,329 A | 5/1994 | Beaty et al. |
| 5,314,424 A | 5/1994 | Nicholas |
| 5,318,221 A | 6/1994 | Green et al. |
| 5,330,502 A | 7/1994 | Hassler et al. |
| 5,332,142 A | 7/1994 | Robinson et al. |
| 5,333,422 A | 8/1994 | Warren et al. |
| 5,334,183 A | 8/1994 | Wuchinich |
| 5,336,232 A | 8/1994 | Green et al. |
| 5,339,799 A | 8/1994 | Kami et al. |
| 5,341,724 A | 8/1994 | Vatel |
| 5,341,810 A | 8/1994 | Dardel |
| 5,342,395 A | 8/1994 | Jarrett et al. |
| 5,342,396 A | 8/1994 | Cook |
| 5,344,060 A | 9/1994 | Gravener et al. |
| 5,350,400 A | 9/1994 | Esposito et al. |
| 5,352,235 A | 10/1994 | Koros et al. |
| 5,352,238 A | 10/1994 | Green et al. |
| 5,354,303 A | 10/1994 | Spaeth et al. |
| 5,356,006 A | 10/1994 | Alpern et al. |
| 5,358,510 A | 10/1994 | Luscombe et al. |
| 5,359,231 A | 10/1994 | Flowers et al. |
| D352,780 S | 11/1994 | Glaeser et al. |
| 5,360,428 A | 11/1994 | Hutchinson, Jr. |
| 5,364,003 A | 11/1994 | Williamson, IV |
| 5,366,134 A | 11/1994 | Green et al. |
| 5,366,479 A | 11/1994 | McGarry et al. |
| 5,370,645 A | 12/1994 | Klicek et al. |
| 5,372,596 A | 12/1994 | Klicek et al. |
| 5,372,602 A | 12/1994 | Burke |
| 5,374,277 A | 12/1994 | Hassler |
| 5,379,933 A | 1/1995 | Green et al. |
| 5,381,782 A | 1/1995 | DeLaRama et al. |
| 5,382,247 A | 1/1995 | Cimino et al. |
| 5,383,880 A | 1/1995 | Hooven |
| 5,383,881 A | 1/1995 | Green et al. |
| 5,383,888 A | 1/1995 | Zvenyatsky et al. |
| 5,383,895 A | 1/1995 | Holmes et al. |
| 5,389,098 A | 2/1995 | Tsuruta et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,312 A | 3/1995 | Desai |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,405,344 A | 4/1995 | Williamson et al. |
| 5,407,293 A | 4/1995 | Crainich |
| 5,409,498 A | 4/1995 | Braddock et al. |
| 5,411,508 A | 5/1995 | Bessler et al. |
| 5,413,267 A | 5/1995 | Solyntjes et al. |
| 5,413,268 A | 5/1995 | Green et al. |
| 5,413,272 A | 5/1995 | Green et al. |
| 5,415,334 A | 5/1995 | Williamson, IV et al. |
| 5,415,335 A | 5/1995 | Knodell, Jr. |
| 5,417,361 A | 5/1995 | Williamson, IV |
| 5,421,829 A | 6/1995 | Olichney et al. |
| 5,422,567 A | 6/1995 | Matsunaga |
| 5,423,809 A | 6/1995 | Klicek |
| 5,425,745 A | 6/1995 | Green et al. |
| 5,431,322 A | 7/1995 | Green et al. |
| 5,431,668 A | 7/1995 | Burbank, III et al. |
| 5,433,721 A | 7/1995 | Hooven et al. |
| 5,438,302 A | 8/1995 | Goble |
| 5,439,479 A | 8/1995 | Schichman et al. |
| 5,441,193 A | 8/1995 | Gravener |
| 5,441,494 A | 8/1995 | Ortiz |
| 5,445,304 A | 8/1995 | Plyley et al. |
| 5,445,644 A | 8/1995 | Pietrafitta et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,452,836 A | 9/1995 | Huitema et al. |
| 5,452,837 A | 9/1995 | Williamson, IV et al. |
| 5,454,827 A | 10/1995 | Aust et al. |
| 5,456,401 A | 10/1995 | Green et al. |
| 5,458,579 A | 10/1995 | Chodorow et al. |
| 5,462,215 A | 10/1995 | Viola et al. |
| 5,464,300 A | 11/1995 | Crainich |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A * | 11/1995 | Tsuruta et al. ............. 227/175.1 |
| 5,470,006 A | 11/1995 | Rodak |
| 5,470,007 A | 11/1995 | Plyley et al. |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,566 A | 12/1995 | Alesi et al. |
| 5,476,206 A | 12/1995 | Green et al. |
| 5,476,479 A | 12/1995 | Green et al. |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,484,095 A | 1/1996 | Green et al. |
| 5,484,398 A | 1/1996 | Stoddard |
| 5,484,451 A | 1/1996 | Akopov et al. |

| Patent No. | Date | Inventor(s) |
|---|---|---|
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,496,312 A | 3/1996 | Klicek |
| 5,496,317 A | 3/1996 | Goble et al. |
| 5,497,933 A | 3/1996 | DeFonzo et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,426 A | 4/1996 | Young et al. |
| 5,509,596 A | 4/1996 | Green et al. |
| 5,509,916 A | 4/1996 | Taylor |
| 5,511,564 A | 4/1996 | Wilk |
| 5,514,129 A | 5/1996 | Smith |
| 5,514,157 A | 5/1996 | Nicholas et al. |
| 5,518,163 A | 5/1996 | Hooven |
| 5,518,164 A | 5/1996 | Hooven |
| 5,520,678 A | 5/1996 | Heckele et al. |
| 5,520,700 A | 5/1996 | Beyar et al. |
| 5,522,817 A | 6/1996 | Sander et al. |
| 5,527,320 A | 6/1996 | Carruthers et al. |
| 5,529,235 A | 6/1996 | Boiarski et al. |
| D372,086 S | 7/1996 | Grasso et al. |
| 5,531,744 A | 7/1996 | Nardella et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,541,376 A | 7/1996 | Ladtkow et al. |
| 5,542,594 A | 8/1996 | McKean et al. |
| 5,543,119 A | 8/1996 | Sutter et al. |
| 5,547,117 A | 8/1996 | Hamblin et al. |
| 5,549,621 A | 8/1996 | Bessler et al. |
| 5,549,628 A | 8/1996 | Cooper et al. |
| 5,549,637 A | 8/1996 | Crainich |
| 5,553,675 A | 9/1996 | Pitzen et al. |
| 5,553,765 A | 9/1996 | Knodel et al. |
| 5,554,169 A | 9/1996 | Green et al. |
| 5,556,416 A | 9/1996 | Clark et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,562,702 A | 10/1996 | Huitema et al. |
| 5,564,615 A | 10/1996 | Bishop et al. |
| 5,569,161 A | 10/1996 | Ebling et al. |
| 5,571,090 A | 11/1996 | Sherts |
| 5,571,100 A | 11/1996 | Goble et al. |
| 5,571,116 A | 11/1996 | Bolanos et al. |
| 5,573,543 A | 11/1996 | Akopov et al. |
| 5,574,431 A | 11/1996 | McKeown et al. |
| 5,575,789 A | 11/1996 | Bell et al. |
| 5,575,799 A | 11/1996 | Bolanos et al. |
| 5,575,803 A | 11/1996 | Cooper et al. |
| 5,577,654 A | 11/1996 | Bishop |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,584,425 A | 12/1996 | Savage et al. |
| 5,586,711 A | 12/1996 | Plyley et al. |
| 5,588,579 A | 12/1996 | Schnut et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,344 A | 2/1997 | Paterson |
| 5,599,350 A | 2/1997 | Schulze et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,450 A | 3/1997 | Zvenyatsky et al. |
| 5,609,285 A | 3/1997 | Grant et al. |
| 5,611,709 A | 3/1997 | McAnulty |
| 5,613,966 A | 3/1997 | Makower et al. |
| 5,618,294 A | 4/1997 | Aust et al. |
| 5,618,303 A | 4/1997 | Marlow et al. |
| 5,618,307 A | 4/1997 | Donlon et al. |
| 5,620,289 A | 4/1997 | Curry |
| 5,620,452 A | 4/1997 | Yoon |
| 5,624,452 A | 4/1997 | Yates |
| 5,626,587 A | 5/1997 | Bishop et al. |
| 5,628,446 A | 5/1997 | Geiste et al. |
| 5,628,743 A | 5/1997 | Cimino |
| 5,630,539 A | 5/1997 | Plyley et al. |
| 5,630,540 A | 5/1997 | Blewett |
| 5,630,782 A | 5/1997 | Adair |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,639,639 A | 6/1997 | Reddy et al. |
| 5,643,291 A | 7/1997 | Pier et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,651,491 A | 7/1997 | Heaton et al. |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,655,698 A | 8/1997 | Yoon |
| 5,657,921 A | 8/1997 | Young et al. |
| 5,658,281 A | 8/1997 | Heard |
| 5,658,300 A | 8/1997 | Bito et al. |
| 5,662,258 A | 9/1997 | Knodel et al. |
| 5,662,260 A | 9/1997 | Yoon |
| 5,662,662 A | 9/1997 | Bishop et al. |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,683,349 A | 11/1997 | Makower et al. |
| 5,685,474 A | 11/1997 | Seeber |
| 5,688,270 A | 11/1997 | Yates et al. |
| 5,690,269 A | 11/1997 | Bolanos et al. |
| 5,692,668 A | 12/1997 | Schulze et al. |
| 5,693,042 A | 12/1997 | Boiarski et al. |
| 5,693,051 A | 12/1997 | Schulze et al. |
| 5,695,494 A | 12/1997 | Becker |
| 5,695,504 A | 12/1997 | Gifford, III et al. |
| 5,695,524 A | 12/1997 | Kelley et al. |
| 5,697,543 A | 12/1997 | Burdorff |
| 5,697,943 A | 12/1997 | Sauer et al. |
| 5,700,270 A | 12/1997 | Peyser et al. |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |

| | | |
|---|---|---|
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,680 A | 1/1998 | Yates et al. |
| 5,711,472 A | 1/1998 | Bryan |
| 5,713,128 A | 2/1998 | Schrenk et al. |
| 5,713,505 A | 2/1998 | Huitema |
| 5,713,895 A | 2/1998 | Lontine et al. |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Cotellessa |
| 5,720,744 A | 2/1998 | Eggleston et al. |
| D393,067 S | 3/1998 | Geary et al. |
| 5,725,536 A | 3/1998 | Oberlin et al. |
| 5,725,554 A | 3/1998 | Simon et al. |
| 5,728,121 A | 3/1998 | Bimbo et al. |
| 5,730,758 A | 3/1998 | Allgeyer |
| 5,732,871 A | 3/1998 | Clark et al. |
| 5,732,872 A | 3/1998 | Bolduc et al. |
| 5,735,445 A | 4/1998 | Vidal et al. |
| 5,735,848 A | 4/1998 | Yates et al. |
| 5,735,874 A | 4/1998 | Measamer et al. |
| 5,738,474 A | 4/1998 | Blewett |
| 5,738,648 A | 4/1998 | Lands et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |
| 5,752,644 A | 5/1998 | Bolanos et al. |
| 5,752,965 A | 5/1998 | Francis et al. |
| 5,755,717 A | 5/1998 | Yates et al. |
| 5,758,814 A | 6/1998 | Gallagher et al. |
| 5,762,255 A | 6/1998 | Chrisman et al. |
| 5,762,256 A | 6/1998 | Mastri et al. |
| 5,766,188 A | 6/1998 | Igaki |
| 5,766,205 A | 6/1998 | Zvenyatsky et al. |
| 5,769,892 A | 6/1998 | Kingwell |
| 5,772,379 A | 6/1998 | Evensen |
| 5,772,578 A | 6/1998 | Heimberger et al. |
| 5,772,659 A | 6/1998 | Becker et al. |
| 5,776,130 A | 7/1998 | Buysse et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A * | 7/1998 | Koukline .................. 227/176.1 |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,787,897 A | 8/1998 | Kieturakis |
| 5,792,135 A | 8/1998 | Madhani et al. |
| 5,792,165 A | 8/1998 | Klieman et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,906 A | 8/1998 | Rhum et al. |
| 5,797,959 A | 8/1998 | Castro et al. |
| 5,799,857 A | 9/1998 | Robertson et al. |
| 5,807,378 A | 9/1998 | Jensen et al. |
| 5,807,393 A | 9/1998 | Williamson, IV et al. |
| 5,809,441 A | 9/1998 | McKee |
| 5,810,811 A | 9/1998 | Yates et al. |
| 5,810,855 A | 9/1998 | Rayburn et al. |
| 5,813,813 A | 9/1998 | Daum et al. |
| 5,814,057 A | 9/1998 | Oi et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,826,776 A | 10/1998 | Schulze et al. |
| 5,827,271 A | 10/1998 | Buysse et al. |
| 5,829,662 A | 11/1998 | Allen et al. |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,843,132 A | 12/1998 | Ilvento |
| 5,846,254 A | 12/1998 | Schulze et al. |
| 5,849,011 A | 12/1998 | Jones et al. |
| 5,855,311 A | 1/1999 | Hamblin et al. |
| 5,855,583 A | 1/1999 | Wang et al. |
| 5,860,975 A | 1/1999 | Goble et al. |
| 5,865,361 A | 2/1999 | Milliman et al. |
| 5,868,760 A | 2/1999 | McGuckin, Jr. |
| 5,871,135 A | 2/1999 | Williamson IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,937 A | 3/1999 | Green et al. |
| 5,878,938 A | 3/1999 | Bittner et al. |
| 5,891,160 A | 4/1999 | Williamson, IV et al. |
| 5,893,506 A | 4/1999 | Powell |
| 5,894,979 A | 4/1999 | Powell |
| 5,897,562 A | 4/1999 | Bolanos et al. |
| 5,899,914 A | 5/1999 | Zirps et al. |
| 5,901,895 A | 5/1999 | Heaton et al. |
| 5,902,312 A | 5/1999 | Frater et al. |
| 5,904,693 A | 5/1999 | Dicesare et al. |
| 5,906,625 A | 5/1999 | Bito et al. |
| 5,908,402 A | 6/1999 | Blythe |
| 5,908,427 A | 6/1999 | McKean et al. |
| 5,911,353 A | 6/1999 | Bolanos et al. |
| 5,915,616 A | 6/1999 | Viola et al. |
| 5,918,791 A | 7/1999 | Sorrentino et al. |
| 5,919,198 A | 7/1999 | Graves, Jr. et al. |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,944,172 A | 8/1999 | Hannula |
| 5,944,715 A | 8/1999 | Goble et al. |
| 5,948,030 A | 9/1999 | Miller et al. |
| 5,951,552 A | 9/1999 | Long et al. |
| 5,951,574 A | 9/1999 | Stefanchik et al. |
| 5,954,259 A * | 9/1999 | Viola et al. .................. 227/176.1 |
| 5,964,774 A | 10/1999 | McKean et al. |
| 5,971,916 A | 10/1999 | Koren |
| 5,988,479 A | 11/1999 | Palmer |
| 6,003,517 A | 12/1999 | Sheffield et al. |
| 6,004,319 A | 12/1999 | Goble et al. |
| 6,010,054 A | 1/2000 | Johnson et al. |
| 6,012,494 A | 1/2000 | Balazs |
| 6,013,076 A | 1/2000 | Goble et al. |
| 6,015,406 A | 1/2000 | Goble et al. |
| 6,017,322 A | 1/2000 | Snoke et al. |
| 6,017,356 A | 1/2000 | Frederick et al. |
| 6,022,352 A | 2/2000 | Vandewalle |
| 6,024,741 A | 2/2000 | Williamson, IV et al. |
| 6,024,748 A | 2/2000 | Manzo et al. |
| 6,027,501 A | 2/2000 | Goble et al. |
| 6,032,849 A | 3/2000 | Mastri et al. |
| 6,033,378 A | 3/2000 | Lundquist et al. |
| 6,033,399 A | 3/2000 | Gines |
| 6,033,427 A | 3/2000 | Lee |
| 6,039,733 A | 3/2000 | Buysse et al. |
| 6,039,734 A | 3/2000 | Goble |
| 6,045,560 A | 4/2000 | McKean et al. |
| 6,050,472 A | 4/2000 | Shibata |
| 6,053,390 A | 4/2000 | Green et al. |
| 6,056,746 A | 5/2000 | Goble et al. |
| 6,063,097 A | 5/2000 | Oi et al. |
| 6,063,098 A | 5/2000 | Houser et al. |
| 6,066,132 A | 5/2000 | Chen et al. |
| 6,068,627 A | 5/2000 | Orszulak et al. |
| 6,071,233 A | 6/2000 | Ishikawa et al. |

| | | |
|---|---|---|
| 6,074,386 A | 6/2000 | Goble et al. |
| 6,077,286 A | 6/2000 | Cuschieri et al. |
| 6,079,606 A | 6/2000 | Milliman et al. |
| 6,082,577 A | 7/2000 | Coates et al. |
| 6,083,234 A | 7/2000 | Nicholas et al. |
| 6,083,242 A | 7/2000 | Cook |
| 6,086,600 A | 7/2000 | Kortenbach |
| 6,090,106 A | 7/2000 | Goble et al. |
| 6,093,186 A | 7/2000 | Goble |
| 6,099,537 A | 8/2000 | Sugai et al. |
| 6,099,551 A | 8/2000 | Gabbay |
| 6,102,271 A | 8/2000 | Longo et al. |
| 6,109,500 A | 8/2000 | Alli et al. |
| 6,117,158 A | 9/2000 | Measamer et al. |
| 6,119,913 A | 9/2000 | Adams et al. |
| 6,120,433 A | 9/2000 | Mizuno et al. |
| 6,123,241 A | 9/2000 | Walter et al. |
| H1904 H | 10/2000 | Yates et al. |
| 6,126,058 A | 10/2000 | Adams et al. |
| 6,126,670 A | 10/2000 | Walker et al. |
| 6,131,789 A | 10/2000 | Schulze et al. |
| 6,132,368 A | 10/2000 | Cooper |
| 6,139,546 A | 10/2000 | Koenig et al. |
| 6,155,473 A | 12/2000 | Tompkins et al. |
| 6,156,056 A | 12/2000 | Kearns et al. |
| 6,159,146 A | 12/2000 | El Gazayerli |
| 6,159,200 A | 12/2000 | Verdura et al. |
| 6,162,208 A | 12/2000 | Hipps |
| 6,165,175 A | 12/2000 | Wampler et al. |
| 6,165,184 A | 12/2000 | Verdura et al. |
| 6,168,605 B1 | 1/2001 | Measamer et al. |
| 6,171,316 B1 | 1/2001 | Kovac et al. |
| 6,171,330 B1 | 1/2001 | Benchetrit |
| 6,174,308 B1 | 1/2001 | Goble et al. |
| 6,174,309 B1 | 1/2001 | Wrublewski et al. |
| 6,179,776 B1 | 1/2001 | Adams et al. |
| 6,181,105 B1 | 1/2001 | Cutolo et al. |
| 6,193,129 B1 | 2/2001 | Bittner et al. |
| 6,197,042 B1 | 3/2001 | Ginn et al. |
| 6,202,914 B1 | 3/2001 | Geiste et al. |
| 6,214,028 B1 | 4/2001 | Yoon et al. |
| 6,220,368 B1 | 4/2001 | Ark et al. |
| 6,223,835 B1 | 5/2001 | Habedank et al. |
| 6,228,081 B1 | 5/2001 | Goble |
| 6,228,084 B1 | 5/2001 | Kirwan, Jr. |
| 6,231,565 B1 | 5/2001 | Tovey et al. |
| 6,234,178 B1 | 5/2001 | Goble et al. |
| 6,241,139 B1 | 6/2001 | Milliman et al. |
| 6,241,723 B1 | 6/2001 | Heim et al. |
| 6,249,076 B1 | 6/2001 | Madden et al. |
| 6,250,532 B1 | 6/2001 | Green et al. |
| 6,258,107 B1 | 7/2001 | Balazs et al. |
| 6,261,286 B1 | 7/2001 | Goble et al. |
| 6,264,086 B1 | 7/2001 | McGuckin, Jr. |
| 6,264,087 B1 | 7/2001 | Whitman |
| 6,270,508 B1 | 8/2001 | Klieman et al. |
| 6,273,897 B1 | 8/2001 | Dalessandro et al. |
| 6,277,114 B1 | 8/2001 | Bullivant et al. |
| 6,293,942 B1 | 9/2001 | Goble et al. |
| 6,296,640 B1 | 10/2001 | Wampler et al. |
| 6,302,311 B1 | 10/2001 | Adams et al. |
| 6,306,134 B1 | 10/2001 | Goble et al. |
| 6,309,403 B1 | 10/2001 | Minor et al. |
| 6,315,184 B1 | 11/2001 | Whitman |
| 6,320,123 B1 | 11/2001 | Reimers |
| 6,324,339 B1 | 11/2001 | Hudson et al. |
| 6,325,799 B1 | 12/2001 | Goble |
| 6,325,810 B1 | 12/2001 | Hamilton et al. |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,334,860 B1 | 1/2002 | Dorn |
| 6,336,926 B1 | 1/2002 | Goble |
| 6,338,737 B1 | 1/2002 | Toledano |
| 6,346,077 B1 | 2/2002 | Taylor et al. |
| 6,352,503 B1 | 3/2002 | Matsui et al. |
| 6,358,224 B1 | 3/2002 | Tims et al. |
| 6,364,877 B1 | 4/2002 | Goble et al. |
| 6,364,888 B1 | 4/2002 | Niemeyer et al. |
| 6,373,152 B1 | 4/2002 | Wang et al. |
| 6,387,113 B1 | 5/2002 | Hawkins et al. |
| 6,387,114 B2 | 5/2002 | Adams |
| 6,391,038 B2 | 5/2002 | Vargas et al. |
| 6,398,781 B1 | 6/2002 | Goble et al. |
| 6,398,797 B2 | 6/2002 | Bombard et al. |
| 6,406,440 B1 | 6/2002 | Stefanchik |
| 6,409,724 B1 | 6/2002 | Penny et al. |
| H2037 H | 7/2002 | Yates et al. |
| 6,416,486 B1 | 7/2002 | Wampler |
| 6,416,509 B1 | 7/2002 | Goble et al. |
| 6,419,695 B1 | 7/2002 | Gabbay |
| RE37,814 E | 8/2002 | Allgeyer |
| 6,436,097 B1 | 8/2002 | Nardella |
| 6,436,107 B1 | 8/2002 | Wang et al. |
| 6,436,122 B1 | 8/2002 | Frank et al. |
| 6,439,446 B1 | 8/2002 | Perry et al. |
| 6,440,146 B2 | 8/2002 | Nicholas et al. |
| 6,443,973 B1 | 9/2002 | Whitman |
| 6,450,391 B1 | 9/2002 | Kayan et al. |
| 6,468,275 B1 | 10/2002 | Wampler et al. |
| 6,471,106 B1 | 10/2002 | Reining |
| 6,482,200 B2 | 11/2002 | Shippert |
| 6,485,490 B2 | 11/2002 | Wampler et al. |
| 6,488,196 B1 | 12/2002 | Fenton, Jr. |
| 6,488,197 B1 | 12/2002 | Whitman |
| 6,491,201 B1 | 12/2002 | Whitman |
| 6,491,690 B1 | 12/2002 | Goble et al. |
| 6,491,701 B2 | 12/2002 | Tierney et al. |
| 6,492,785 B1 | 12/2002 | Kasten et al. |
| 6,494,896 B1 | 12/2002 | D'Alessio et al. |
| 6,503,257 B2 | 1/2003 | Grant et al. |
| 6,503,259 B2 | 1/2003 | Huxel et al. |
| 6,505,768 B2 | 1/2003 | Whitman |
| 6,510,854 B2 | 1/2003 | Goble |
| 6,511,468 B1 | 1/2003 | Cragg et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,522,101 B2 | 2/2003 | Malackowski |
| 6,543,456 B1 | 4/2003 | Freeman |
| 6,547,786 B1 | 4/2003 | Goble |
| 6,550,546 B2 | 4/2003 | Thurler et al. |
| 6,551,333 B2 | 4/2003 | Kuhns et al. |
| 6,554,861 B2 | 4/2003 | Knox et al. |
| 6,558,379 B1 | 5/2003 | Batchelor et al. |
| 6,565,560 B1 | 5/2003 | Goble et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,427 B1 | 6/2003 | Goble et al. |
| 6,588,643 B2 | 7/2003 | Bolduc et al. |
| 6,589,164 B1 | 7/2003 | Flaherty |
| 6,592,597 B2 | 7/2003 | Grant et al. |
| 6,596,432 B2 | 7/2003 | Kawakami et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,605,078 B2 | 8/2003 | Adams |
| 6,605,669 B2 | 8/2003 | Awokola et al. |
| 6,616,686 B2 | 9/2003 | Coleman et al. |
| 6,619,529 B2 | 9/2003 | Green et al. |
| 6,620,166 B1 | 9/2003 | Wenstrom, Jr. et al. |
| 6,629,630 B2 | 10/2003 | Adams |
| 6,629,974 B2 | 10/2003 | Penny et al. |
| 6,629,988 B2 | 10/2003 | Weadock |
| 6,636,412 B2 | 10/2003 | Smith |
| 6,638,108 B2 | 10/2003 | Tachi |
| 6,638,285 B2 | 10/2003 | Gabbay |
| 6,641,528 B2 | 11/2003 | Torii |
| 6,644,532 B2 | 11/2003 | Green et al. |
| 6,648,816 B2 | 11/2003 | Irion et al. |
| D484,243 S | 12/2003 | Ryan et al. |
| D484,595 S | 12/2003 | Ryan et al. |
| D484,596 S | 12/2003 | Ryan et al. |
| 6,656,193 B2 | 12/2003 | Grant et al. |
| 6,666,875 B1 | 12/2003 | Sakurai et al. |
| 6,669,073 B2 | 12/2003 | Milliman et al. |

| Patent | Kind | Date | Inventor |
|---|---|---|---|
| 6,671,185 | B2 | 12/2003 | Duval |
| D484,977 | S | 1/2004 | Ryan et al. |
| 6,676,660 | B2 | 1/2004 | Wampler et al. |
| 6,679,410 | B2 | 1/2004 | Würsch et al. |
| 6,681,978 | B2 | 1/2004 | Geiste et al. |
| 6,681,979 | B2 | 1/2004 | Whitman |
| 6,682,527 | B2 | 1/2004 | Strul |
| 6,682,528 | B2 | 1/2004 | Frazier et al. |
| 6,685,727 | B2 | 2/2004 | Fisher et al. |
| 6,692,507 | B2 | 2/2004 | Pugsley et al. |
| 6,695,199 | B2 | 2/2004 | Whitman |
| 6,698,643 | B2 | 3/2004 | Whitman |
| 6,699,235 | B2 | 3/2004 | Wallace et al. |
| 6,704,210 | B1 | 3/2004 | Myers |
| 6,705,503 | B1 | 3/2004 | Pedicini et al. |
| 6,716,223 | B2 | 4/2004 | Leopold et al. |
| 6,716,232 | B1 | 4/2004 | Vidal et al. |
| 6,716,233 | B1 | 4/2004 | Whitman |
| 6,722,552 | B2 | 4/2004 | Fenton, Jr. |
| 6,723,087 | B2 | 4/2004 | O'Neill et al. |
| 6,723,091 | B2 | 4/2004 | Goble et al. |
| 6,726,697 | B2 | 4/2004 | Nicholas et al. |
| 6,740,030 | B2 | 5/2004 | Martone et al. |
| 6,747,121 | B2 | 6/2004 | Gogolewski |
| 6,749,560 | B1 | 6/2004 | Konstorum et al. |
| 6,752,768 | B2 | 6/2004 | Burdorff et al. |
| 6,752,816 | B2 | 6/2004 | Culp et al. |
| 6,755,195 | B1 | 6/2004 | Lemke et al. |
| 6,755,338 | B2 | 6/2004 | Hahnen et al. |
| 6,758,846 | B2 | 7/2004 | Goble et al. |
| 6,761,685 | B2 | 7/2004 | Adams et al. |
| 6,767,352 | B2 | 7/2004 | Field et al. |
| 6,767,356 | B2 | 7/2004 | Kanner et al. |
| 6,769,594 | B2 | 8/2004 | Orban, III |
| 6,773,438 | B1 | 8/2004 | Knodel et al. |
| 6,780,151 | B2 | 8/2004 | Grabover et al. |
| 6,780,180 | B1 | 8/2004 | Goble et al. |
| 6,783,524 | B2 | 8/2004 | Anderson et al. |
| 6,786,382 | B1 | 9/2004 | Hoffman |
| 6,786,864 | B2 | 9/2004 | Matsuura et al. |
| 6,786,896 | B1 | 9/2004 | Madhani et al. |
| 6,790,173 | B2 | 9/2004 | Saadat et al. |
| 6,793,652 | B1 | 9/2004 | Whitman et al. |
| 6,805,273 | B2 | 10/2004 | Bilotti et al. |
| 6,806,808 | B1 | 10/2004 | Watters et al. |
| 6,808,525 | B2 | 10/2004 | Latterell et al. |
| 6,814,741 | B2 | 11/2004 | Bowman et al. |
| 6,817,508 | B1 | 11/2004 | Racenet et al. |
| 6,817,509 | B2 | 11/2004 | Geiste et al. |
| 6,817,974 | B2 | 11/2004 | Cooper et al. |
| 6,821,273 | B2 | 11/2004 | Mollenauer |
| 6,821,284 | B2 | 11/2004 | Sturtz et al. |
| 6,827,725 | B2 | 12/2004 | Batchelor et al. |
| 6,828,902 | B2 | 12/2004 | Casden |
| 6,830,174 | B2 | 12/2004 | Hillstead et al. |
| 6,832,998 | B2 | 12/2004 | Goble |
| 6,834,001 | B2 | 12/2004 | Myono |
| 6,835,199 | B2 | 12/2004 | McGuckin, Jr. et al. |
| 6,843,403 | B2 | 1/2005 | Whitman |
| 6,843,789 | B2 | 1/2005 | Goble |
| 6,846,307 | B2 | 1/2005 | Whitman et al. |
| 6,846,308 | B2 | 1/2005 | Whitman et al. |
| 6,846,309 | B2 | 1/2005 | Whitman et al. |
| 6,849,071 | B2 | 2/2005 | Whitman et al. |
| RE38,708 | E | 3/2005 | Bolanos et al. |
| 6,866,178 | B2 | 3/2005 | Adams et al. |
| 6,866,671 | B2 | 3/2005 | Tierney et al. |
| 6,872,214 | B2 | 3/2005 | Sonnenschein et al. |
| 6,874,669 | B2 | 4/2005 | Adams et al. |
| 6,877,647 | B2 | 4/2005 | Ratcliff et al. |
| 6,878,106 | B1 | 4/2005 | Herrmann |
| 6,889,116 | B2 | 5/2005 | Jinno |
| 6,893,435 | B2 | 5/2005 | Goble |
| 6,905,057 | B2 | 6/2005 | Swayze et al. |
| 6,905,497 | B2 | 6/2005 | Truckai et al. |
| 6,913,608 | B2 | 7/2005 | Liddicoat et al. |
| 6,913,613 | B2 | 7/2005 | Schwarz et al. |
| 6,923,803 | B2 | 8/2005 | Goble |
| 6,929,641 | B2 | 8/2005 | Goble et al. |
| 6,931,830 | B2 | 8/2005 | Liao |
| 6,936,042 | B2 | 8/2005 | Wallace et al. |
| 6,939,358 | B2 | 9/2005 | Palacios et al. |
| 6,942,662 | B2 | 9/2005 | Goble et al. |
| 6,945,444 | B2 | 9/2005 | Gresham et al. |
| 6,953,138 | B1 | 10/2005 | Dworak et al. |
| 6,953,139 | B2 | 10/2005 | Milliman et al. |
| 6,959,851 | B2 | 11/2005 | Heinrich |
| 6,959,852 | B2 | 11/2005 | Shelton, IV et al. |
| 6,960,163 | B2 | 11/2005 | Ewers et al. |
| 6,960,220 | B2 | 11/2005 | Marino et al. |
| 6,964,363 | B2 | 11/2005 | Wales et al. |
| 6,966,907 | B2 | 11/2005 | Goble |
| 6,966,909 | B2 | 11/2005 | Marshall et al. |
| 6,972,199 | B2 | 12/2005 | Lebouitz et al. |
| 6,974,462 | B2 | 12/2005 | Sater |
| 6,978,921 | B2 | 12/2005 | Shelton, IV et al. |
| 6,978,922 | B2 | 12/2005 | Bilotti et al. |
| 6,981,628 | B2 | 1/2006 | Wales |
| 6,981,941 | B2 | 1/2006 | Whitman et al. |
| 6,981,978 | B2 | 1/2006 | Gannoe |
| 6,984,203 | B2 | 1/2006 | Tartaglia et al. |
| 6,984,231 | B2 | 1/2006 | Goble et al. |
| 6,986,451 | B1 | 1/2006 | Mastri et al. |
| 6,988,649 | B2 | 1/2006 | Shelton, IV et al. |
| 6,988,650 | B2 | 1/2006 | Schwemberger et al. |
| 6,990,796 | B2 | 1/2006 | Schnipke et al. |
| 6,994,708 | B2 | 2/2006 | Manzo |
| 6,997,931 | B2 | 2/2006 | Sauer et al. |
| 7,000,819 | B2 | 2/2006 | Swayze et al. |
| 7,001,380 | B2 | 2/2006 | Goble |
| 7,001,408 | B2 | 2/2006 | Knodel et al. |
| 7,008,435 | B2 | 3/2006 | Cummins |
| 7,018,390 | B2 | 3/2006 | Turovskiy et al. |
| 7,025,743 | B2 | 4/2006 | Mann et al. |
| 7,029,435 | B2 | 4/2006 | Nakao |
| 7,032,793 | B2 | 4/2006 | Roberts et al. |
| 7,032,799 | B2 | 4/2006 | Viola et al. |
| 7,033,356 | B2 | 4/2006 | Latterell et al. |
| 7,036,680 | B1 | 5/2006 | Flannery |
| 7,037,344 | B2 | 5/2006 | Kagan et al. |
| 7,044,352 | B2 | 5/2006 | Shelton, IV et al. |
| 7,044,353 | B2 | 5/2006 | Mastri et al. |
| 7,048,687 | B1 | 5/2006 | Reuss et al. |
| 7,052,494 | B2 | 5/2006 | Goble et al. |
| 7,055,730 | B2 | 6/2006 | Ehrenfels et al. |
| 7,055,731 | B2 | 6/2006 | Shelton, IV et al. |
| 7,056,284 | B2 | 6/2006 | Martone et al. |
| 7,056,330 | B2 | 6/2006 | Gayton |
| 7,059,508 | B2 | 6/2006 | Shelton, IV et al. |
| 7,063,712 | B2 | 6/2006 | Vargas et al. |
| 7,066,879 | B2 | 6/2006 | Fowler et al. |
| 7,066,944 | B2 | 6/2006 | Laufer et al. |
| 7,070,083 | B2 | 7/2006 | Jankowski |
| 7,070,559 | B2 | 7/2006 | Adams et al. |
| 7,071,287 | B2 | 7/2006 | Rhine et al. |
| 7,075,770 | B1 | 7/2006 | Smith |
| 7,077,856 | B2 | 7/2006 | Whitman |
| 7,080,769 | B2 | 7/2006 | Vresh et al. |
| 7,081,114 | B2 | 7/2006 | Rashidi |
| 7,083,073 | B2 | 8/2006 | Yoshie et al. |
| 7,083,075 | B2 | 8/2006 | Swayze et al. |
| 7,083,571 | B2 | 8/2006 | Wang et al. |
| 7,083,615 | B2 | 8/2006 | Peterson et al. |
| 7,087,071 | B2 | 8/2006 | Nicholas et al. |
| 7,090,637 | B2 | 8/2006 | Danitz et al. |
| 7,090,673 | B2 | 8/2006 | Dycus et al. |
| 7,090,684 | B2 | 8/2006 | McGuckin, Jr. et al. |
| 7,094,202 | B2 | 8/2006 | Nobis et al. |
| 7,097,089 | B2 | 8/2006 | Marczyk |
| 7,098,794 | B2 | 8/2006 | Lindsay et al. |
| 7,104,741 | B2 | 9/2006 | Krohn |
| 7,108,695 | B2 | 9/2006 | Witt et al. |
| 7,108,701 | B2 | 9/2006 | Evens et al. |
| 7,108,709 | B2 | 9/2006 | Cummins |
| 7,111,769 | B2 | 9/2006 | Wales et al. |
| 7,112,214 | B2 | 9/2006 | Peterson et al. |
| RE39,358 | E | 10/2006 | Goble |
| 7,114,642 | B2 | 10/2006 | Whitman |

| | | | | | | |
|---|---|---|---|---|---|---|
| 7,118,582 B1 | 10/2006 | Wang et al. | | 7,336,184 B2 | 2/2008 | Smith et al. |
| 7,121,446 B2 | 10/2006 | Arad et al. | | 7,338,513 B2 | 3/2008 | Lee et al. |
| 7,122,028 B2 | 10/2006 | Looper et al. | | 7,343,920 B2 | 3/2008 | Toby et al. |
| 7,128,253 B2 | 10/2006 | Mastri et al. | | 7,348,763 B1 | 3/2008 | Reinhart et al. |
| 7,128,254 B2 | 10/2006 | Shelton, IV et al. | | 7,351,258 B2 | 4/2008 | Ricotta et al. |
| 7,128,748 B2 | 10/2006 | Mooradian et al. | | 7,354,447 B2 | 4/2008 | Shelton, IV et al. |
| 7,131,445 B2 | 11/2006 | Amoah | | 7,357,287 B2 | 4/2008 | Shelton, IV et al. |
| 7,133,601 B2 | 11/2006 | Phillips et al. | | 7,364,060 B2 | 4/2008 | Milliman |
| 7,140,527 B2 | 11/2006 | Ehrenfels et al. | | 7,364,061 B2 | 4/2008 | Swayze et al. |
| 7,140,528 B2 | 11/2006 | Shelton, IV | | 7,377,928 B2 | 5/2008 | Zubik et al. |
| 7,143,923 B2 | 12/2006 | Shelton, IV et al. | | 7,380,695 B2 | 6/2008 | Doll et al. |
| 7,143,924 B2 | 12/2006 | Scirica et al. | | 7,380,696 B2 | 6/2008 | Shelton, IV et al. |
| 7,143,925 B2 | 12/2006 | Shelton, IV et al. | | 7,388,217 B2 | 6/2008 | Buschbeck et al. |
| 7,143,926 B2 | 12/2006 | Shelton, IV et al. | | 7,396,356 B2 | 7/2008 | Mollenauer |
| 7,147,138 B2 | 12/2006 | Shelton, IV | | 7,397,364 B2 | 7/2008 | Govari |
| 7,147,139 B2 | 12/2006 | Schwemberger et al. | | 7,398,907 B2 | 7/2008 | Racenet et al. |
| 7,147,637 B2 | 12/2006 | Goble | | 7,398,908 B2 | 7/2008 | Holsten et al. |
| 7,147,650 B2 | 12/2006 | Lee | | 7,404,508 B2 | 7/2008 | Smith et al. |
| 7,150,748 B2 | 12/2006 | Ebbutt et al. | | 7,404,509 B2 | 7/2008 | Ortiz et al. |
| 7,153,300 B2 | 12/2006 | Goble | | 7,407,075 B2 | 8/2008 | Holsten et al. |
| 7,156,863 B2 | 1/2007 | Sonnenschein et al. | | 7,407,078 B2 | 8/2008 | Shelton, IV et al. |
| 7,159,750 B2 | 1/2007 | Racenet et al. | | 7,410,086 B2 | 8/2008 | Ortiz et al. |
| 7,160,299 B2 | 1/2007 | Baily | | 7,416,101 B2 | 8/2008 | Shelton, IV et al. |
| 7,161,036 B2 | 1/2007 | Oikawa et al. | | 7,418,078 B2 | 8/2008 | Blanz et al. |
| 7,168,604 B2 | 1/2007 | Milliman et al. | | 7,419,080 B2 | 9/2008 | Smith et al. |
| 7,172,104 B2 | 2/2007 | Scirica et al. | | 7,422,136 B1 * | 9/2008 | Marczyk ............... 227/175.1 |
| 7,179,223 B2 | 2/2007 | Motoki et al. | | 7,422,139 B2 * | 9/2008 | Shelton et al. ............ 227/180.1 |
| 7,179,267 B2 | 2/2007 | Nolan et al. | | 7,424,965 B2 | 9/2008 | Racenet et al. |
| 7,182,239 B1 | 2/2007 | Myers | | 7,431,188 B1 * | 10/2008 | Marczyk ............... 227/175.1 |
| 7,188,758 B2 | 3/2007 | Viola et al. | | 7,431,189 B2 | 10/2008 | Shelton, IV et al. |
| 7,195,627 B2 | 3/2007 | Amoah et al. | | 7,431,694 B2 | 10/2008 | Stefanchik et al. |
| 7,204,835 B2 | 4/2007 | Latterell et al. | | 7,431,730 B2 | 10/2008 | Viola |
| 7,207,233 B2 | 4/2007 | Wadge | | 7,434,715 B2 | 10/2008 | Shelton, IV et al. |
| 7,207,471 B2 | 4/2007 | Heinrich et al. | | 7,434,717 B2 | 10/2008 | Shelton, IV et al. |
| 7,207,472 B2 | 4/2007 | Wukusick et al. | | 7,438,209 B1 | 10/2008 | Hess et al. |
| 7,208,005 B2 | 4/2007 | Frecker et al. | | 7,439,354 B2 | 10/2008 | Lenges et al. |
| 7,210,609 B2 | 5/2007 | Leiboff et | | 7,441,684 B2 | 10/2008 | Shelton, IV et al. |
| 7,211,081 B2 | 5/2007 | Goble | | 7,441,685 B1 | 10/2008 | Boudreaux |
| 7,211,084 B2 | 5/2007 | Goble et al. | | 7,442,201 B2 | 10/2008 | Pugsley et al. |
| 7,213,736 B2 | 5/2007 | Wales et al. | | 7,448,525 B2 | 11/2008 | Shelton, IV et al. |
| 7,214,224 B2 | 5/2007 | Goble | | 7,455,208 B2 | 11/2008 | Wales et al. |
| 7,217,285 B2 | 5/2007 | Vargas et al. | | 7,461,767 B2 | 12/2008 | Viola et al. |
| 7,220,260 B2 | 5/2007 | Fleming et al. | | 7,464,846 B2 | 12/2008 | Shelton, IV et al. |
| 7,220,272 B2 | 5/2007 | Weadock | | 7,464,847 B2 | 12/2008 | Viola et al. |
| 7,225,963 B2 | 6/2007 | Scirica | | 7,464,849 B2 * | 12/2008 | Shelton et al. ............ 227/178.1 |
| 7,225,964 B2 | 6/2007 | Mastri et al. | | 7,467,740 B2 | 12/2008 | Shelton, IV et al. |
| 7,234,624 B2 | 6/2007 | Gresham et al. | | 7,467,849 B2 | 12/2008 | Silverbrook et al. |
| 7,235,089 B1 | 6/2007 | McGuckin, Jr. | | 7,472,814 B2 | 1/2009 | Mastri et al. |
| 7,235,302 B2 | 6/2007 | Jing et al. | | 7,472,815 B2 | 1/2009 | Shelton, IV et al. |
| 7,237,708 B1 | 7/2007 | Guy et al. | | 7,473,253 B2 | 1/2009 | Dycus et al. |
| 7,238,195 B2 | 7/2007 | Viola | | 7,479,608 B2 | 1/2009 | Smith |
| 7,241,288 B2 | 7/2007 | Braun | | 7,481,347 B2 | 1/2009 | Roy |
| 7,246,734 B2 | 7/2007 | Shelton, IV | | 7,481,349 B2 | 1/2009 | Holsten et al. |
| 7,247,161 B2 | 7/2007 | Johnston et al. | | 7,481,824 B2 | 1/2009 | Boudreaux et al. |
| 7,252,660 B2 | 8/2007 | Kunz | | 7,485,133 B2 | 2/2009 | Cannon et al. |
| 7,255,696 B2 | 8/2007 | Goble et al. | | 7,490,749 B2 | 2/2009 | Schall et al. |
| 7,258,262 B2 | 8/2007 | Mastri et al. | | 7,494,039 B2 | 2/2009 | Racenet et al. |
| 7,260,431 B2 | 8/2007 | Libbus et al. | | 7,494,499 B2 | 2/2009 | Nagase et al. |
| 7,265,374 B2 | 9/2007 | Lee et al. | | 7,501,198 B2 | 3/2009 | Barlev et al. |
| 7,267,679 B2 | 9/2007 | McGuckin, Jr. et al. | | 7,506,790 B2 | 3/2009 | Shelton, IV |
| 7,273,483 B2 | 9/2007 | Wiener et al. | | 7,506,791 B2 | 3/2009 | Omaits et al. |
| 7,278,562 B2 | 10/2007 | Mastri et al. | | 7,510,107 B2 | 3/2009 | Timm et al. |
| 7,278,563 B1 | 10/2007 | Green | | 7,524,320 B2 | 4/2009 | Tierney et al. |
| 7,278,994 B2 | 10/2007 | Goble | | 7,530,985 B2 | 5/2009 | Takemoto et al. |
| 7,282,048 B2 | 10/2007 | Goble et al. | | 7,546,940 B2 | 6/2009 | Milliman et al. |
| 7,295,907 B2 | 11/2007 | Lu et al. | | 7,547,312 B2 | 6/2009 | Bauman et al. |
| 7,296,724 B2 | 11/2007 | Green et al. | | 7,549,563 B2 | 6/2009 | Mather et al. |
| 7,297,149 B2 | 11/2007 | Vitali et al. | | 7,549,564 B2 | 6/2009 | Boudreaux |
| 7,300,450 B2 | 11/2007 | Vleugels et al. | | 7,552,854 B2 | 6/2009 | Wixey et al. |
| 7,303,106 B2 | 12/2007 | Milliman et al. | | 7,556,185 B2 | 7/2009 | Viola |
| 7,303,107 B2 | 12/2007 | Milliman et al. | | 7,556,186 B2 | 7/2009 | Milliman |
| 7,303,108 B2 | 12/2007 | Shelton, IV | | 7,559,450 B2 | 7/2009 | Wales et al. |
| 7,303,556 B2 | 12/2007 | Metzger | | 7,559,452 B2 | 7/2009 | Wales et al. |
| 7,308,998 B2 | 12/2007 | Mastri et al. | | 7,563,862 B2 | 7/2009 | Sieg et al. |
| 7,324,572 B2 | 1/2008 | Chang | | 7,566,300 B2 | 7/2009 | Devierre et al. |
| 7,328,828 B2 | 2/2008 | Ortiz et al. | | 7,568,603 B2 | 8/2009 | Shelton, IV et al. |
| 7,328,829 B2 | 2/2008 | Arad et al. | | 7,568,604 B2 | 8/2009 | Ehrenfels et al. |
| 7,330,004 B2 | 2/2008 | DeJonge et al. | | 7,568,619 B2 | 8/2009 | Todd et al. |
| 7,334,717 B2 | 2/2008 | Rethy et al. | | 7,575,144 B2 | 8/2009 | Ortiz et al. |

| Patent No. | Date | Inventor |
|---|---|---|
| 7,588,175 B2 | 9/2009 | Timm et al. |
| 7,588,176 B2 * | 9/2009 | Timm et al. ............. 227/179.1 |
| 7,597,229 B2 | 10/2009 | Boudreaux et al. |
| 7,600,663 B2 | 10/2009 | Green |
| 7,604,150 B2 | 10/2009 | Boudreaux |
| 7,604,151 B2 | 10/2009 | Hess et al. |
| 7,611,038 B2 | 11/2009 | Racenet et al. |
| 7,615,003 B2 | 11/2009 | Stefanchik et al. |
| 7,624,902 B2 | 12/2009 | Marczyk et al. |
| 7,631,793 B2 | 12/2009 | Rethy et al. |
| 7,637,409 B2 | 12/2009 | Marczyk |
| 7,641,092 B2 | 1/2010 | Kruszynski et al. |
| 7,641,093 B2 | 1/2010 | Doll et al. |
| 7,644,848 B2 | 1/2010 | Swayze et al. |
| 7,651,498 B2 | 1/2010 | Shifrin et al. |
| 7,656,131 B2 | 2/2010 | Embrey et al. |
| 7,658,311 B2 * | 2/2010 | Boudreaux ............. 227/175.2 |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,674,255 B2 | 3/2010 | Braun |
| 7,682,307 B2 | 3/2010 | Danitz et al. |
| 7,686,826 B2 | 3/2010 | Lee et al. |
| 7,688,028 B2 | 3/2010 | Phillips et al. |
| 7,691,098 B2 | 4/2010 | Wallace et al. |
| 7,699,204 B2 | 4/2010 | Viola |
| 7,699,859 B2 | 4/2010 | Bombard et al. |
| 7,708,180 B2 | 5/2010 | Murray et al. |
| 7,708,758 B2 | 5/2010 | Lee et al. |
| 7,714,239 B2 | 5/2010 | Smith |
| 7,717,312 B2 | 5/2010 | Beetel |
| 7,721,930 B2 | 5/2010 | McKenna et al. |
| 7,721,931 B2 | 5/2010 | Shelton, IV et al. |
| 7,721,934 B2 | 5/2010 | Shelton, IV et al. |
| 7,721,936 B2 * | 5/2010 | Shalton et al. ............. 227/180.1 |
| 7,722,610 B2 | 5/2010 | Viola et al. |
| 7,726,537 B2 | 6/2010 | Olson et al. |
| 7,726,538 B2 | 6/2010 | Holsten et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,744,627 B2 | 6/2010 | Orban, III et al. |
| 7,753,245 B2 | 7/2010 | Boudreaux et al. |
| 7,753,904 B2 | 7/2010 | Shelton, IV et al. |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,775 B2 | 8/2010 | Shelton, IV et al. |
| 7,771,396 B2 | 8/2010 | Stefanchik et al. |
| 7,772,720 B2 | 8/2010 | McGee et al. |
| 7,776,060 B2 | 8/2010 | Mooradian et al. |
| 7,780,054 B2 | 8/2010 | Wales |
| 7,780,055 B2 | 8/2010 | Scirica et al. |
| 7,780,663 B2 | 8/2010 | Yates et al. |
| 7,780,685 B2 | 8/2010 | Hunt et al. |
| 7,784,662 B2 | 8/2010 | Wales et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,803,151 B2 * | 9/2010 | Whitman ............. 606/1 |
| 7,806,891 B2 | 10/2010 | Nowlin et al. |
| 7,810,692 B2 | 10/2010 | Hall et al. |
| 7,810,693 B2 | 10/2010 | Broehl et al. |
| 7,815,565 B2 | 10/2010 | Stefanchik et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,824,401 B2 | 11/2010 | Manzo et al. |
| 7,828,794 B2 | 11/2010 | Sartor |
| 7,828,808 B2 | 11/2010 | Hinman et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,836,400 B2 | 11/2010 | May et al. |
| 7,837,080 B2 | 11/2010 | Schwemberger |
| 7,837,081 B2 | 11/2010 | Holsten et al. |
| 7,845,533 B2 | 12/2010 | Marczyk et al. |
| 7,845,534 B2 | 12/2010 | Viola et al. |
| 7,846,149 B2 | 12/2010 | Jankowski |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,870,989 B2 | 1/2011 | Viola et al. |
| 7,871,418 B2 | 1/2011 | Thompson et al. |
| 7,887,530 B2 | 2/2011 | Zemlok et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,909,191 B2 | 3/2011 | Baker et al. |
| 7,909,221 B2 | 3/2011 | Viola et al. |
| 7,913,891 B2 | 3/2011 | Doll et al. |
| 7,914,543 B2 | 3/2011 | Roth et al. |
| 7,918,377 B2 | 4/2011 | Measamer et al. |
| 7,922,061 B2 | 4/2011 | Shelton, IV et al. |
| 7,922,063 B2 | 4/2011 | Zemlok et al. |
| 7,934,630 B2 | 5/2011 | Shelton, IV et al. |
| 7,938,307 B2 | 5/2011 | Bettuchi |
| 7,941,865 B2 | 5/2011 | Seman, Jr. et al. |
| 7,942,303 B2 | 5/2011 | Shah |
| 7,942,890 B2 | 5/2011 | D'Agostino et al. |
| 7,944,175 B2 | 5/2011 | Mori et al. |
| 7,950,560 B2 * | 5/2011 | Zemlok et al. ............. 227/175.1 |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,959,050 B2 * | 6/2011 | Smith et al. ............. 227/175.2 |
| 7,959,051 B2 | 6/2011 | Smith et al. |
| 7,963,963 B2 | 6/2011 | Francischelli et al. |
| 7,966,799 B2 | 6/2011 | Morgan et al. |
| 7,967,180 B2 | 6/2011 | Scirica |
| 7,972,298 B2 | 7/2011 | Wallace et al. |
| 7,980,443 B2 | 7/2011 | Scheib et al. |
| 8,002,795 B2 | 8/2011 | Beetel |
| 8,011,551 B2 | 9/2011 | Marczyk et al. |
| 8,011,555 B2 | 9/2011 | Tarinelli et al. |
| 8,020,743 B2 | 9/2011 | Shelton, IV |
| 8,025,199 B2 | 9/2011 | Whitman et al. |
| 8,028,883 B2 | 10/2011 | Stopek |
| 8,034,077 B2 | 10/2011 | Smith et al. |
| 8,038,045 B2 | 10/2011 | Bettuchi et al. |
| 8,038,046 B2 | 10/2011 | Smith et al. |
| 8,056,787 B2 | 11/2011 | Boudreaux et al. |
| 8,062,330 B2 | 11/2011 | Prommersberger et al. |
| 8,066,167 B2 | 11/2011 | Measamer et al. |
| D650,074 S | 12/2011 | Hunt et al. |
| 8,083,120 B2 | 12/2011 | Shelton, IV et al. |
| 8,091,756 B2 | 1/2012 | Viola |
| 8,097,017 B2 | 1/2012 | Viola |
| 8,108,072 B2 | 1/2012 | Zhao et al. |
| 8,113,410 B2 | 2/2012 | Hall et al. |
| 8,123,103 B2 | 2/2012 | Milliman |
| 8,136,712 B2 | 3/2012 | Zingman |
| 8,141,762 B2 | 3/2012 | Bedi et al. |
| 8,152,041 B2 | 4/2012 | Kostrzewski |
| 8,157,145 B2 | 4/2012 | Shelton, IV et al. |
| 8,157,152 B2 | 4/2012 | Holsten et al. |
| 8,157,153 B2 | 4/2012 | Shelton, IV et al. |
| 8,161,977 B2 | 4/2012 | Shelton, IV et al. |
| 8,167,185 B2 | 5/2012 | Shelton, IV et al. |
| 8,167,895 B2 | 5/2012 | D'Agostino et al. |
| 8,172,124 B2 | 5/2012 | Shelton, IV et al. |
| 8,186,555 B2 | 5/2012 | Shelton, IV et al. |
| 8,186,560 B2 | 5/2012 | Hess et al. |
| 8,196,795 B2 | 6/2012 | Moore et al. |
| 8,196,796 B2 | 6/2012 | Shelton, IV et al. |
| 8,205,781 B2 | 6/2012 | Baxter, III et al. |
| 8,210,411 B2 | 7/2012 | Yates et al. |

| | | |
|---|---|---|
| 8,211,125 B2 | 7/2012 | Spivey |
| 8,215,531 B2 | 7/2012 | Shelton, IV et al. |
| 8,220,468 B2 | 7/2012 | Cooper et al. |
| 8,225,799 B2 | 7/2012 | Bettuchi |
| 8,241,271 B2 | 8/2012 | Millman et al. |
| 8,245,898 B2 | 8/2012 | Smith et al. |
| 8,245,901 B2 | 8/2012 | Stopek |
| 8,256,654 B2 | 9/2012 | Bettuchi et al. |
| 8,257,391 B2 | 9/2012 | Orban, III et al. |
| 2002/0022836 A1 | 2/2002 | Goble et al. |
| 2002/0029036 A1 | 3/2002 | Goble et al. |
| 2002/0117534 A1 | 8/2002 | Green et al. |
| 2002/0134811 A1 | 9/2002 | Napier et al. |
| 2002/0165541 A1 | 11/2002 | Whitman |
| 2003/0093103 A1 | 5/2003 | Malackowski et al. |
| 2003/0105478 A1 | 6/2003 | Whitman et al. |
| 2003/0130677 A1 | 7/2003 | Whitman et al. |
| 2003/0139741 A1 | 7/2003 | Goble et al. |
| 2003/0153908 A1 | 8/2003 | Goble et al. |
| 2003/0195387 A1 | 10/2003 | Kortenbach et al. |
| 2003/0205029 A1 | 11/2003 | Chapolini et al. |
| 2003/0216732 A1 | 11/2003 | Truckai et al. |
| 2003/0220660 A1 | 11/2003 | Kortenbach et al. |
| 2004/0002726 A1 | 1/2004 | Nunez et al. |
| 2004/0006335 A1 | 1/2004 | Garrison |
| 2004/0006340 A1 | 1/2004 | Latterell et al. |
| 2004/0006372 A1 | 1/2004 | Racenet et al. |
| 2004/0030333 A1 | 2/2004 | Goble |
| 2004/0034357 A1 | 2/2004 | Beane et al. |
| 2004/0034369 A1 | 2/2004 | Sauer et al. |
| 2004/0044364 A1 | 3/2004 | DeVries et al. |
| 2004/0068161 A1 | 4/2004 | Couvillon, Jr. |
| 2004/0068307 A1 | 4/2004 | Goble |
| 2004/0070369 A1 | 4/2004 | Sakahibara |
| 2004/0078037 A1 | 4/2004 | Batchelor et al. |
| 2004/0093024 A1 | 5/2004 | Lousararian et al. |
| 2004/0094597 A1 | 5/2004 | Whitman et al. |
| 2004/0097987 A1 | 5/2004 | Pugsley et al. |
| 2004/0101822 A1 | 5/2004 | Wiesner et al. |
| 2004/0108357 A1 | 6/2004 | Milliman et al. |
| 2004/0111081 A1 | 6/2004 | Whitman et al. |
| 2004/0115022 A1 | 6/2004 | Albertson et al. |
| 2004/0116952 A1 | 6/2004 | Sakurai et al. |
| 2004/0147909 A1 | 7/2004 | Johnston et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0181219 A1 | 9/2004 | Goble et al. |
| 2004/0186470 A1 | 9/2004 | Goble et al. |
| 2004/0193189 A1 | 9/2004 | Kortenbach et al. |
| 2004/0222268 A1 | 11/2004 | Bilotti et al. |
| 2004/0230214 A1 | 11/2004 | Donofrio et al. |
| 2004/0232196 A1 | 11/2004 | Shelton, IV et al. |
| 2004/0232201 A1 | 11/2004 | Wenchell et al. |
| 2004/0243151 A1 | 12/2004 | Demmy et al. |
| 2004/0243163 A1 | 12/2004 | Casiano et al. |
| 2004/0243176 A1 | 12/2004 | Hahnen et al. |
| 2004/0254566 A1 | 12/2004 | Plicchi et al. |
| 2004/0254608 A1 | 12/2004 | Huitema et al. |
| 2004/0267310 A1 | 12/2004 | Racenet et al. |
| 2005/0032511 A1 | 2/2005 | Malone et al. |
| 2005/0033357 A1 | 2/2005 | Braun |
| 2005/0054946 A1 | 3/2005 | Krzyzanowski |
| 2005/0059997 A1 | 3/2005 | Bauman et al. |
| 2005/0070929 A1 | 3/2005 | Dalessandro et al. |
| 2005/0080454 A1 | 4/2005 | Drews et al. |
| 2005/0085693 A1 | 4/2005 | Belson et al. |
| 2005/0090817 A1 | 4/2005 | Phan |
| 2005/0103819 A1 | 5/2005 | Racenet et al. |
| 2005/0107814 A1 | 5/2005 | Johnston et al. |
| 2005/0107824 A1 | 5/2005 | Hillstead et al. |
| 2005/0113820 A1 | 5/2005 | Goble et al. |
| 2005/0119525 A1 | 6/2005 | Takemoto |
| 2005/0119669 A1 | 6/2005 | Demmy |
| 2005/0124855 A1 | 6/2005 | Jaffe et al. |
| 2005/0125009 A1 | 6/2005 | Perry et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131437 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0143759 A1 | 6/2005 | Kelly |
| 2005/0145675 A1 | 7/2005 | Hartwick et al. |
| 2005/0154258 A1 | 7/2005 | Tartaglia et al. |
| 2005/0165419 A1 | 7/2005 | Sauer et al. |
| 2005/0165435 A1 | 7/2005 | Johnston et al. |
| 2005/0169974 A1 | 8/2005 | Tenerz et al. |
| 2005/0171522 A1 | 8/2005 | Christopherson |
| 2005/0177181 A1 | 8/2005 | Kagan et al. |
| 2005/0182298 A1 | 8/2005 | Ikeda et al. |
| 2005/0184121 A1 | 8/2005 | Heinrich |
| 2005/0187545 A1 | 8/2005 | Hooven et al. |
| 2005/0187572 A1 | 8/2005 | Johnston et al. |
| 2005/0187576 A1 | 8/2005 | Whitman et al. |
| 2005/0189397 A1 | 9/2005 | Jankowski |
| 2005/0192609 A1 | 9/2005 | Whitman et al. |
| 2005/0192628 A1 | 9/2005 | Viola |
| 2005/0203550 A1 | 9/2005 | Laufer et al. |
| 2005/0216055 A1 | 9/2005 | Scirica et al. |
| 2005/0240222 A1 | 10/2005 | Shipp |
| 2005/0245965 A1 | 11/2005 | Orban, III et al. |
| 2005/0251128 A1 | 11/2005 | Amoah |
| 2005/0256522 A1 | 11/2005 | Francischelli et al. |
| 2005/0261676 A1 | 11/2005 | Hall et al. |
| 2005/0261677 A1 | 11/2005 | Hall et al. |
| 2005/0263563 A1 | 12/2005 | Racenet et al. |
| 2005/0267455 A1 | 12/2005 | Eggers et al. |
| 2005/0274768 A1 | 12/2005 | Cummins et al. |
| 2006/0004407 A1 | 1/2006 | Hiles et al. |
| 2006/0008787 A1 | 1/2006 | Hayman et al. |
| 2006/0011699 A1 | 1/2006 | Olson et al. |
| 2006/0015009 A1 | 1/2006 | Jaffe et al. |
| 2006/0020247 A1 | 1/2006 | Kagan et al. |
| 2006/0020336 A1 | 1/2006 | Liddicoat |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0047275 A1 | 3/2006 | Goble |
| 2006/0047303 A1 | 3/2006 | Ortiz et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0064086 A1 | 3/2006 | Odom |
| 2006/0079735 A1 | 4/2006 | Martone et al. |
| 2006/0085031 A1 | 4/2006 | Bettuchi |
| 2006/0085033 A1 | 4/2006 | Criscuolo et al. |
| 2006/0086032 A1 | 4/2006 | Valencic et al. |
| 2006/0100643 A1 | 5/2006 | Laufer et al. |
| 2006/0108393 A1 | 5/2006 | Heinrich et al. |
| 2006/0111710 A1 | 5/2006 | Goble et al. |
| 2006/0111711 A1 | 5/2006 | Goble |
| 2006/0111723 A1 | 5/2006 | Chapolini et al. |
| 2006/0122636 A1 | 6/2006 | Bailly et al. |
| 2006/0142772 A1 | 6/2006 | Ralph et al. |
| 2006/0149163 A1 | 7/2006 | Hibner et al. |
| 2006/0161185 A1 | 7/2006 | Saadat et al. |
| 2006/0173470 A1 | 8/2006 | Oray et al. |
| 2006/0180634 A1 | 8/2006 | Shelton, IV et al. |
| 2006/0183246 A1 | 8/2006 | Wiesner et al. |
| 2006/0200123 A1 | 9/2006 | Ryan |
| 2006/0212069 A1 | 9/2006 | Shelton, IV |
| 2006/0217729 A1 | 9/2006 | Eskridge et al. |
| 2006/0226196 A1 | 10/2006 | Hueil et al. |
| 2006/0228224 A1 | 10/2006 | Hong et al. |
| 2006/0235469 A1 | 10/2006 | Viola |
| 2006/0241655 A1 | 10/2006 | Viola |
| 2006/0241692 A1 | 10/2006 | McGuckin, Jr. et al. |
| 2006/0244460 A1 | 11/2006 | Weaver |
| 2006/0245971 A1 | 11/2006 | Burns et al. |
| 2006/0258904 A1 | 11/2006 | Stefanchik et al. |
| 2006/0259073 A1 | 11/2006 | Miyamoto et al. |
| 2006/0264927 A1 | 11/2006 | Ryan |
| 2006/0264929 A1 | 11/2006 | Goble et al. |
| 2006/0271042 A1 | 11/2006 | Latterell et al. |

| Pub. No. | Date | Inventor |
|---|---|---|
| 2006/0271102 A1 | 11/2006 | Bosshard et al. |
| 2006/0278680 A1 | 12/2006 | Viola et al. |
| 2006/0278681 A1 | 12/2006 | Viola et al. |
| 2006/0289602 A1 | 12/2006 | Wales et al. |
| 2006/0291981 A1 | 12/2006 | Viola et al. |
| 2007/0023476 A1 | 2/2007 | Whitman et al. |
| 2007/0023477 A1 | 2/2007 | Whitman et al. |
| 2007/0027468 A1 | 2/2007 | Wales et al. |
| 2007/0027469 A1 | 2/2007 | Smith et al. |
| 2007/0034668 A1 | 2/2007 | Holsten et al. |
| 2007/0055219 A1 | 3/2007 | Whitman et al. |
| 2007/0070574 A1 | 3/2007 | Nerheim et al. |
| 2007/0073341 A1 | 3/2007 | Smith |
| 2007/0078484 A1 | 4/2007 | Talarico et al. |
| 2007/0083193 A1 | 4/2007 | Werneth et al. |
| 2007/0084897 A1 | 4/2007 | Shelton, IV et al. |
| 2007/0102452 A1 | 5/2007 | Shelton, IV et al. |
| 2007/0102453 A1 | 5/2007 | Morgan et al. |
| 2007/0102472 A1 | 5/2007 | Shelton, IV |
| 2007/0106113 A1 | 5/2007 | Ravo |
| 2007/0106317 A1 | 5/2007 | Shelton, IV et al. |
| 2007/0114261 A1 | 5/2007 | Ortiz et al. |
| 2007/0118175 A1 | 5/2007 | Butler et al. |
| 2007/0129605 A1 | 6/2007 | Schaaf |
| 2007/0135803 A1 | 6/2007 | Belson |
| 2007/0158358 A1 | 7/2007 | Mason, II et al. |
| 2007/0158385 A1 | 7/2007 | Hueil et al. |
| 2007/0170225 A1 | 7/2007 | Shelton, IV et al. |
| 2007/0173806 A1 | 7/2007 | Orszulak et al. |
| 2007/0173813 A1 | 7/2007 | Odom |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175955 A1 | 8/2007 | Shelton, IV et al. |
| 2007/0175962 A1 | 8/2007 | Shelton, IV et al. |
| 2007/0175964 A1 | 8/2007 | Shelton, IV et al. |
| 2007/0181632 A1 | 8/2007 | Milliman |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0203510 A1 | 8/2007 | Bettuchi |
| 2007/0213750 A1 | 9/2007 | Weadock |
| 2007/0221700 A1 | 9/2007 | Ortiz et al. |
| 2007/0221701 A1 | 9/2007 | Ortiz et al. |
| 2007/0225562 A1 | 9/2007 | Spivey et al. |
| 2007/0239028 A1 | 10/2007 | Houser et al. |
| 2007/0246505 A1 | 10/2007 | Pace-Floridia et al. |
| 2007/0260278 A1 | 11/2007 | Wheeler et al. |
| 2007/0262116 A1 | 11/2007 | Hueil et al. |
| 2007/0270784 A1 | 11/2007 | Smith et al. |
| 2007/0270884 A1 | 11/2007 | Smith et al. |
| 2007/0288044 A1 | 12/2007 | Jinno et al. |
| 2007/0295780 A1 | 12/2007 | Shelton et al. |
| 2007/0299427 A1 | 12/2007 | Yeung et al. |
| 2008/0015598 A1 | 1/2008 | Prommersberger |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0078800 A1 | 4/2008 | Hess et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083813 A1 | 4/2008 | Zemlok et al. |
| 2008/0114385 A1 | 5/2008 | Byrum et al. |
| 2008/0129253 A1 | 6/2008 | Shiue et al. |
| 2008/0140115 A1 | 6/2008 | Stopek |
| 2008/0167522 A1 | 7/2008 | Giordano et al. |
| 2008/0167672 A1 | 7/2008 | Giordano et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0172088 A1 | 7/2008 | Smith et al. |
| 2008/0183193 A1 | 7/2008 | Omori et al. |
| 2008/0185419 A1 | 8/2008 | Smith et al. |
| 2008/0197167 A1 | 8/2008 | Viola et al. |
| 2008/0200835 A1 | 8/2008 | Monson et al. |
| 2008/0228029 A1 | 9/2008 | Mikkaichi et al. |
| 2008/0245841 A1 | 10/2008 | Smith et al. |
| 2008/0251568 A1 | 10/2008 | Zemlok et al. |
| 2008/0251569 A1 | 10/2008 | Smith et al. |
| 2008/0255413 A1 | 10/2008 | Zemlok et al. |
| 2008/0262654 A1 | 10/2008 | Omori et al. |
| 2008/0283570 A1 | 11/2008 | Boyden et al. |
| 2008/0287944 A1 | 11/2008 | Pearson et al. |
| 2008/0290134 A1 | 11/2008 | Bettuchi et al. |
| 2008/0296346 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012534 A1 | 1/2009 | Madhani et al. |
| 2009/0012556 A1 | 1/2009 | Boudreaux et al. |
| 2009/0020958 A1 | 1/2009 | Soul |
| 2009/0054908 A1 | 2/2009 | Zand et al. |
| 2009/0057369 A1 | 3/2009 | Smith et al. |
| 2009/0090763 A1 | 4/2009 | Zemlok et al. |
| 2009/0093728 A1 | 4/2009 | Hyde et al. |
| 2009/0108048 A1 | 4/2009 | Zemlok et al. |
| 2009/0114701 A1 | 5/2009 | Zemlok et al. |
| 2009/0143805 A1 | 6/2009 | Palmer et al. |
| 2009/0149871 A9 | 6/2009 | Kagan et al. |
| 2009/0157067 A1 | 6/2009 | Kane et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0209946 A1 | 8/2009 | Swayze et al. |
| 2009/0209979 A1 | 8/2009 | Yates et al. |
| 2009/0209990 A1 | 8/2009 | Yates et al. |
| 2009/0213685 A1 | 8/2009 | Mak et al. |
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0292283 A1 | 11/2009 | Odom |
| 2009/0308907 A1 | 12/2009 | Nalagatla et al. |
| 2010/0012704 A1 | 1/2010 | Tarinelli Racenet et al. |
| 2010/0023024 A1 | 1/2010 | Zeiner et al. |
| 2010/0049084 A1 | 2/2010 | Nock et al. |
| 2010/0069942 A1 | 3/2010 | Shelton, IV |
| 2010/0072254 A1 | 3/2010 | Aranyi et al. |
| 2010/0076475 A1 | 3/2010 | Yates et al. |
| 2010/0089970 A1 | 4/2010 | Smith et al. |
| 2010/0089972 A1 | 4/2010 | Marczyk |
| 2010/0096431 A1 | 4/2010 | Smith et al. |
| 2010/0108740 A1 | 5/2010 | Pastorelli et al. |
| 2010/0108741 A1 | 5/2010 | Hessler et al. |

| | | | | | | |
|---|---|---|---|---|---|---|
| 2010/0127042 A1 | 5/2010 | Shelton, IV | | 2011/0290851 A1 | 12/2011 | Shelton, IV |
| 2010/0133317 A1 | 6/2010 | Shelton, IV et al. | | 2011/0290853 A1 | 12/2011 | Shelton, IV et al. |
| 2010/0133318 A1 | 6/2010 | Boudreaux | | 2011/0290854 A1 | 12/2011 | Timm et al. |
| 2010/0145146 A1 | 6/2010 | Melder | | 2011/0290855 A1 | 12/2011 | Moore et al. |
| 2010/0163598 A1 | 7/2010 | Belzer | | 2011/0290856 A1 | 12/2011 | Shelton, IV et al. |
| 2010/0179382 A1 | 7/2010 | Shelton, IV et al. | | 2011/0290857 A1 | 12/2011 | Shelton, IV et al. |
| 2010/0186219 A1 | 7/2010 | Smith | | 2011/0295242 A1 | 12/2011 | Spivey et al. |
| 2010/0193566 A1 | 8/2010 | Scheib et al. | | 2011/0295269 A1 | 12/2011 | Swensgard et al. |
| 2010/0193567 A1 | 8/2010 | Scheib et al. | | 2011/0295270 A1 | 12/2011 | Giordano et al. |
| 2010/0193568 A1 | 8/2010 | Scheib et al. | | 2011/0295295 A1 | 12/2011 | Shelton, IV et al. |
| 2010/0193569 A1 | 8/2010 | Yates et al. | | 2012/0022523 A1 | 1/2012 | Smith et al. |
| 2010/0198220 A1 | 8/2010 | Boudreaux et al. | | 2012/0024934 A1 | 2/2012 | Shelton, IV et al. |
| 2010/0200637 A1 | 8/2010 | Beetel | | 2012/0024935 A1 | 2/2012 | Shelton, IV et al. |
| 2010/0213241 A1 | 8/2010 | Bedi et al. | | 2012/0024936 A1 | 2/2012 | Baxter, III et al. |
| 2010/0222901 A1 | 9/2010 | Swayze et al. | | 2012/0029272 A1 | 2/2012 | Shelton, IV et al. |
| 2010/0224669 A1 | 9/2010 | Shelton, IV et al. | | 2012/0029544 A1 | 2/2012 | Shelton, IV et al. |
| 2010/0230465 A1 | 9/2010 | Smith et al. | | 2012/0029547 A1 | 2/2012 | Shelton, IV et al. |
| 2010/0243707 A1 | 9/2010 | Olson et al. | | 2012/0046692 A1 | 2/2012 | Smith et al. |
| 2010/0243708 A1 | 9/2010 | Aranyi et al. | | 2012/0061448 A1 | 3/2012 | Zingman |
| 2010/0243709 A1 | 9/2010 | Hess et al. | | 2012/0071711 A1 | 3/2012 | Shelton, IV et al. |
| 2010/0258611 A1 | 10/2010 | Smith et al. | | 2012/0071866 A1 | 3/2012 | Kerr et al. |
| 2010/0264193 A1 | 10/2010 | Huang et al. | | 2012/0074196 A1 | 3/2012 | Shelton, IV et al. |
| 2010/0264194 A1 | 10/2010 | Huang et al. | | 2012/0074198 A1 | 3/2012 | Huitema et al. |
| 2010/0276471 A1 | 11/2010 | Whitman | | 2012/0074200 A1 | 3/2012 | Schmid et al. |
| 2010/0294827 A1 | 11/2010 | Boyden et al. | | 2012/0074201 A1 | 3/2012 | Baxter, III et al. |
| 2010/0294829 A1 | 11/2010 | Giordano et al. | | 2012/0080332 A1 | 4/2012 | Shelton, IV et al. |
| 2010/0301095 A1 | 12/2010 | Shelton, IV et al. | | 2012/0080333 A1 | 4/2012 | Woodard, Jr. et al. |
| 2010/0305552 A1 | 12/2010 | Shelton, IV et al. | | 2012/0080334 A1 | 4/2012 | Shelton, IV et al. |
| 2010/0308100 A1 | 12/2010 | Boudreaux | | 2012/0080335 A1 | 4/2012 | Shelton, IV et al. |
| 2010/0312261 A1 | 12/2010 | Suzuki et al. | | 2012/0080336 A1 | 4/2012 | Shelton, IV et al. |
| 2011/0006099 A1 | 1/2011 | Hall et al. | | 2012/0080337 A1 | 4/2012 | Shelton, IV et al. |
| 2011/0006101 A1 | 1/2011 | Hall et al. | | 2012/0080338 A1 | 4/2012 | Shelton, IV et al. |
| 2011/0006103 A1 | 1/2011 | Laurent et al. | | 2012/0080339 A1 | 4/2012 | Shelton, IV et al. |
| 2011/0011914 A1 | 1/2011 | Baxter, III et al. | | 2012/0080340 A1 | 4/2012 | Shelton, IV et al. |
| 2011/0011915 A1 | 1/2011 | Shelton, IV | | 2012/0080344 A1 | 4/2012 | Shelton, IV |
| 2011/0017801 A1 | 1/2011 | Zemlok et al. | | 2012/0080345 A1 | 4/2012 | Morgan et al. |
| 2011/0022032 A1 | 1/2011 | Zemlok et al. | | 2012/0080475 A1 | 4/2012 | Smith et al. |
| 2011/0024477 A1 | 2/2011 | Hall et al. | | 2012/0080477 A1 | 4/2012 | Leimbach et al. |
| 2011/0024478 A1 | 2/2011 | Shelton, IV | | 2012/0080478 A1 | 4/2012 | Morgan et al. |
| 2011/0024479 A1 | 2/2011 | Swensgard et al. | | 2012/0080479 A1 | 4/2012 | Shelton, IV |
| 2011/0036887 A1 | 2/2011 | Zemlok et al. | | 2012/0080480 A1 | 4/2012 | Woodard, Jr. et al. |
| 2011/0042441 A1 | 2/2011 | Shelton, IV et al. | | 2012/0080481 A1 | 4/2012 | Widenhouse et al. |
| 2011/0060363 A1 | 3/2011 | Hess et al. | | 2012/0080482 A1 | 4/2012 | Schall et al. |
| 2011/0068145 A1 | 3/2011 | Bedi et al. | | 2012/0080483 A1 | 4/2012 | Riestenberg et al. |
| 2011/0068148 A1 | 3/2011 | Hall et al. | | 2012/0080484 A1 | 4/2012 | Morgan et al. |
| 2011/0084112 A1 | 4/2011 | Kostrzewski | | 2012/0080485 A1 | 4/2012 | Woodard, Jr. et al. |
| 2011/0084115 A1 | 4/2011 | Bedi et al. | | 2012/0080486 A1 | 4/2012 | Woodard, Jr. et al. |
| 2011/0087276 A1 | 4/2011 | Bedi et al. | | 2012/0080487 A1 | 4/2012 | Woodard, Jr. et al. |
| 2011/0087279 A1 | 4/2011 | Shah et al. | | 2012/0080488 A1 | 4/2012 | Shelton, IV et al. |
| 2011/0095068 A1 | 4/2011 | Patel | | 2012/0080489 A1 | 4/2012 | Shelton, IV et al. |
| 2011/0101065 A1 | 5/2011 | Milliman | | 2012/0080490 A1 | 4/2012 | Shelton, IV et al. |
| 2011/0114697 A1 | 5/2011 | Baxter, III et al. | | 2012/0080491 A1 | 4/2012 | Shelton, IV et al. |
| 2011/0114698 A1 | 5/2011 | Baxter, III et al. | | 2012/0080493 A1 | 4/2012 | Shelton, IV et al. |
| 2011/0114699 A1 | 5/2011 | Baxter, III et al. | | 2012/0080496 A1 | 4/2012 | Schall et al. |
| 2011/0114700 A1 | 5/2011 | Baxter, III et al. | | 2012/0080498 A1 | 4/2012 | Shelton, IV et al. |
| 2011/0118761 A1 | 5/2011 | Baxter, III et al. | | 2012/0080499 A1 | 4/2012 | Schall et al. |
| 2011/0125176 A1 | 5/2011 | Yates et al. | | 2012/0080500 A1 | 4/2012 | Morgan et al. |
| 2011/0125177 A1 | 5/2011 | Yates et al. | | 2012/0080501 A1 | 4/2012 | Morgan et al. |
| 2011/0132963 A1 | 6/2011 | Giordano et al. | | 2012/0080502 A1 | 4/2012 | Morgan et al. |
| 2011/0132964 A1 | 6/2011 | Weisenburgh, II et al. | | 2012/0080503 A1 | 4/2012 | Woodard, Jr. et al. |
| 2011/0132965 A1 | 6/2011 | Moore et al. | | 2012/0083833 A1 | 4/2012 | Shelton, IV et al. |
| 2011/0144430 A1 | 6/2011 | Spivey et al. | | 2012/0083834 A1 | 4/2012 | Shelton, IV et al. |
| 2011/0147433 A1 | 6/2011 | Shelton, IV et al. | | 2012/0083835 A1 | 4/2012 | Shelton, IV et al. |
| 2011/0147434 A1 | 6/2011 | Hueil et al. | | 2012/0083836 A1 | 4/2012 | Shelton, IV et al. |
| 2011/0155780 A1 | 6/2011 | Boudreaux | | 2012/0132450 A1 | 5/2012 | Timm et al. |
| 2011/0155781 A1 | 6/2011 | Swensgard et al. | | 2012/0138660 A1 | 6/2012 | Shelton, IV |
| 2011/0155785 A1 | 6/2011 | Laurent et al. | | 2012/0160721 A1 | 6/2012 | Shelton, IV et al. |
| 2011/0155787 A1 | 6/2011 | Baxter, III et al. | | 2012/0175399 A1 | 7/2012 | Shelton et al. |
| 2011/0163147 A1 | 7/2011 | Laurent et al. | | 2012/0187179 A1 | 7/2012 | Gleiman |
| 2011/0174861 A1 | 7/2011 | Shelton, IV et al. | | 2012/0199630 A1 | 8/2012 | Shelton, IV et al. |
| 2011/0174863 A1 | 7/2011 | Shelton, IV et al. | | 2012/0199631 A1 | 8/2012 | Shelton, IV et al. |
| 2011/0178536 A1 | 7/2011 | Kostrzewski | | 2012/0199632 A1 | 8/2012 | Spivey et al. |
| 2011/0192882 A1 | 8/2011 | Hess et al. | | 2012/0199633 A1 | 8/2012 | Shelton, IV et al. |
| 2011/0210156 A1 | 9/2011 | Smith et al. | | 2012/0203247 A1 | 8/2012 | Shelton, IV et al. |
| 2011/0226837 A1 | 9/2011 | Baxter, III et al. | | 2012/0205421 A1 | 8/2012 | Shelton, IV |
| 2011/0233258 A1 | 9/2011 | Boudreaux | | 2012/0211546 A1 | 8/2012 | Shelton, IV |
| 2011/0275901 A1 | 11/2011 | Shelton, IV | | 2012/0234890 A1 | 9/2012 | Aronhalt et al. |
| 2011/0276083 A1 | 11/2011 | Shelton, IV et al. | | 2012/0234891 A1 | 9/2012 | Aronhalt et al. |
| 2011/0288573 A1 | 11/2011 | Yates et al. | | 2012/0234892 A1 | 9/2012 | Aronhalt et al. |

| | | | |
|---|---|---|---|
| 2012/0234893 A1 | 9/2012 | Schuckmann et al. | |
| 2012/0234895 A1 | 9/2012 | O'Connor et al. | |
| 2012/0234896 A1 | 9/2012 | Ellerhorst et al. | |
| 2012/0234897 A1 | 9/2012 | Shelton, IV et al. | |
| 2012/0234898 A1 | 9/2012 | Shelton, IV et al. | |
| 2012/0234899 A1 | 9/2012 | Scheib et al. | |
| 2012/0234900 A1 | 9/2012 | Swayze | |
| 2012/0238823 A1 | 9/2012 | Hagerty et al. | |
| 2012/0238824 A1 | 9/2012 | Widenhouse et al. | |
| 2012/0238826 A1 | 9/2012 | Yoo et al. | |
| 2012/0238829 A1 | 9/2012 | Shelton, IV et al. | |
| 2012/0239009 A1 | 9/2012 | Mollere et al. | |
| 2012/0239010 A1 | 9/2012 | Shelton, IV et al. | |
| 2012/0239012 A1 | 9/2012 | Laurent et al. | |
| 2012/0239075 A1 | 9/2012 | Widenhouse et al. | |
| 2012/0239082 A1 | 9/2012 | Shelton, IV et al. | |
| 2012/0241491 A1 | 9/2012 | Aldridge et al. | |
| 2012/0241492 A1 | 9/2012 | Shelton, IV et al. | |
| 2012/0241493 A1 | 9/2012 | Baxter, III et al. | |
| 2012/0241494 A1 | 9/2012 | Mandakolathur Vasudevan et al. | |
| 2012/0241497 A1 | 9/2012 | Mandakolathur Vasudevan et al. | |
| 2012/0241498 A1 | 9/2012 | Gonzalez et al. | |
| 2012/0241499 A1 | 9/2012 | Baxter, III et al. | |
| 2012/0241500 A1 | 9/2012 | Timmer et al. | |
| 2012/0241501 A1 | 9/2012 | Swayze et al. | |
| 2012/0241502 A1 | 9/2012 | Aldridge et al. | |
| 2012/0241503 A1 | 9/2012 | Baxter, III et al. | |
| 2012/0241505 A1 | 9/2012 | Alexander, III et al. | |
| 2012/0248169 A1 | 10/2012 | Widenhouse et al. | |
| 2012/0253298 A1 | 10/2012 | Henderson et al. | |
| 2012/0265230 A1 | 10/2012 | Yates et al. | |
| 2012/0273551 A1 | 11/2012 | Shelton, IV et al. | |
| 2012/0283707 A1 | 11/2012 | Giordano et al. | |
| 2012/0286019 A1 | 11/2012 | Hueil et al. | |
| 2012/0292367 A1 | 11/2012 | Morgan et al. | |
| 2012/0292370 A1 | 11/2012 | Hess et al. | |
| 2012/0298719 A1 | 11/2012 | Shelton, IV et al. | |
| 2013/0012931 A1 | 1/2013 | Spivey et al. | |
| 2013/0012957 A1 | 1/2013 | Shelton, IV et al. | |
| 2013/0020376 A1 | 1/2013 | Shelton, IV et al. | |
| 2013/0023861 A1 | 1/2013 | Shelton, IV et al. | |

FOREIGN PATENT DOCUMENTS

| | | |
|---|---|---|
| CA | 2512960 A1 | 1/2006 |
| CN | 2488482 Y | 5/2002 |
| CN | 1634601 A | 7/2005 |
| CN | 1868411 A | 11/2006 |
| CN | 1915180 A | 2/2007 |
| CN | 101011286 A | 8/2007 |
| CN | 101095621 A | 1/2008 |
| DE | 2736139 C | 5/1914 |
| DE | 1775926 A | 1/1972 |
| DE | 3036217 A1 | 4/1982 |
| DE | 3210466 A1 | 9/1983 |
| DE | 9412228 U | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 10052679 A1 | 5/2001 |
| DE | 20112837 U1 | 10/2001 |
| DE | 20121753 U1 | 4/2003 |
| DE | 10314072 A2 | 10/2004 |
| DE | 202007003114 U1 | 6/2007 |
| EP | 0122045 A1 | 10/1984 |
| EP | 0646357 A1 | 4/1985 |
| EP | 0070230 B1 | 10/1985 |
| EP | 0156774 A2 | 10/1985 |
| EP | 0387980 B1 | 10/1985 |
| EP | 0033548 B1 | 5/1986 |
| EP | 0129442 B1 | 11/1987 |
| EP | 0276104 A2 | 7/1988 |
| EP | 0178941 B1 | 1/1991 |
| EP | 0248844 B1 | 1/1993 |
| EP | 0545029 A1 | 6/1993 |
| EP | 0277959 B1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0634144 A1 | 1/1995 |
| EP | 0646356 A2 | 4/1995 |
| EP | 0653189 A2 | 5/1995 |
| EP | 0669104 A1 | 8/1995 |
| EP | 0511470 B1 | 10/1995 |
| EP | 0679367 A2 | 11/1995 |
| EP | 0392647 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0705571 A1 | 4/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0625077 B1 | 7/1997 |
| EP | 0633749 B1 | 8/1997 |
| EP | 0710090 B1 | 8/1997 |
| EP | 0578125 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0676173 B1 | 9/1998 |
| EP | 0678007 B1 | 9/1998 |
| EP | 0698618 B1 | 9/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0700230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0843906 B1 | 3/2000 |
| EP | 0552050 B1 | 5/2000 |
| EP | 0833592 B1 | 5/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1090592 A1 | 4/2001 |
| EP | 1095627 A1 | 5/2001 |
| EP | 1256318 B1 | 5/2001 |
| EP | 0806914 B1 | 9/2001 |
| EP | 0768840 B1 | 12/2001 |
| EP | 0908152 B1 | 1/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 1284120 A1 | 2/2003 |

| | | | | | | |
|---|---|---|---|---|---|---|
| EP | 1287788 | A1 | 3/2003 | EP | 1769758 A1 | 4/2007 |
| EP | 0717966 | B1 | 4/2003 | EP | 1581128 B1 | 5/2007 |
| EP | 0869742 | B1 | 5/2003 | EP | 1785097 A2 | 5/2007 |
| EP | 0829235 | B1 | 6/2003 | EP | 1790293 A2 | 5/2007 |
| EP | 0887046 | B1 | 7/2003 | EP | 1800610 A1 | 6/2007 |
| EP | 0852480 | B1 | 8/2003 | EP | 1300117 B1 | 8/2007 |
| EP | 0891154 | B1 | 9/2003 | EP | 1813199 A1 | 8/2007 |
| EP | 0813843 | B1 | 10/2003 | EP | 1813201 A1 | 8/2007 |
| EP | 0873089 | B1 | 10/2003 | EP | 1813202 A1 | 8/2007 |
| EP | 0856326 | B1 | 11/2003 | EP | 1813203 A2 | 8/2007 |
| EP | 1374788 | A1 | 1/2004 | EP | 1813206 A1 | 8/2007 |
| EP | 0741996 | B1 | 2/2004 | EP | 1813207 A1 | 8/2007 |
| EP | 0814712 | B1 | 2/2004 | EP | 1813209 A1 | 8/2007 |
| EP | 1402837 | A1 | 3/2004 | EP | 1487359 B1 | 10/2007 |
| EP | 0705570 | B1 | 4/2004 | EP | 1599146 B1 | 10/2007 |
| EP | 0959784 | B1 | 4/2004 | EP | 1839596 A1 | 10/2007 |
| EP | 1407719 | A2 | 4/2004 | EP | 2110083 A2 | 10/2007 |
| EP | 1086713 | B1 | 5/2004 | EP | 1857057 A2 | 11/2007 |
| EP | 0996378 | B1 | 6/2004 | EP | 1402821 B1 | 12/2007 |
| EP | 1426012 | A1 | 6/2004 | EP | 1872727 A1 | 1/2008 |
| EP | 1442694 | A1 | 8/2004 | EP | 1897502 A1 | 3/2008 |
| EP | 0888749 | B1 | 9/2004 | EP | 1330201 B1 | 6/2008 |
| EP | 0959786 | B1 | 9/2004 | EP | 1702568 B1 | 7/2008 |
| EP | 1459695 | A1 | 9/2004 | EP | 1943957 A2 | 7/2008 |
| EP | 1473819 | A1 | 11/2004 | EP | 1943964 A1 | 7/2008 |
| EP | 1477119 | A1 | 11/2004 | EP | 1943976 A2 | 7/2008 |
| EP | 1479345 | A1 | 11/2004 | EP | 1593337 B1 | 8/2008 |
| EP | 1479347 | A1 | 11/2004 | EP | 1970014 A1 | 9/2008 |
| EP | 1479348 | A1 | 11/2004 | EP | 1980213 A2 | 10/2008 |
| EP | 0754437 | B2 | 12/2004 | EP | 1759645 B1 | 11/2008 |
| EP | 1025807 | B1 | 12/2004 | EP | 1990014 A2 | 11/2008 |
| EP | 1001710 | B1 | 1/2005 | EP | 1693008 B1 | 12/2008 |
| EP | 1520521 | A1 | 4/2005 | EP | 1759640 B1 | 12/2008 |
| EP | 1520525 | A1 | 4/2005 | EP | 2000102 A2 | 12/2008 |
| EP | 1522264 | A1 | 4/2005 | EP | 2008595 A2 | 12/2008 |
| EP | 1550408 | A1 | 7/2005 | EP | 1736104 B1 | 3/2009 |
| EP | 1557129 | A1 | 7/2005 | EP | 1749486 B1 | 3/2009 |
| EP | 1064883 | B1 | 8/2005 | EP | 2039316 A2 | 3/2009 |
| EP | 1067876 | B1 | 8/2005 | EP | 1721576 B1 | 4/2009 |
| EP | 0870473 | B1 | 9/2005 | EP | 1733686 B1 | 4/2009 |
| EP | 1157666 | B1 | 9/2005 | EP | 2044890 A1 | 4/2009 |
| EP | 0880338 | B1 | 10/2005 | EP | 1550413 B1 | 6/2009 |
| EP | 1158917 | B1 | 11/2005 | EP | 1745748 B1 | 8/2009 |
| EP | 1344498 | B1 | 11/2005 | EP | 2090237 A1 | 8/2009 |
| EP | 1330989 | B1 | 12/2005 | EP | 2090244 A2 | 8/2009 |
| EP | 0771176 | B2 | 1/2006 | EP | 2090245 A1 | 8/2009 |
| EP | 1621138 | A2 | 2/2006 | EP | 2090256 A2 | 8/2009 |
| EP | 1621139 | A2 | 2/2006 | EP | 2095777 A2 | 9/2009 |
| EP | 1621141 | A2 | 2/2006 | EP | 2110082 A1 | 10/2009 |
| EP | 1621145 | A2 | 2/2006 | EP | 1813208 BI | 11/2009 |
| EP | 1621151 | A2 | 2/2006 | EP | 2116195 A1 | 11/2009 |
| EP | 1034746 | B1 | 3/2006 | EP | 1607050 B1 | 12/2009 |
| EP | 1632191 | A2 | 3/2006 | EP | 1815804 B1 | 12/2009 |
| EP | 1520523 | A1 | 4/2006 | EP | 1566150 B1 | 4/2010 |
| EP | 1523942 | A2 | 4/2006 | EP | 1769754 B1 | 6/2010 |
| EP | 1065981 | B1 | 5/2006 | EP | 1535565 B1 | 10/2010 |
| EP | 1082944 | B1 | 5/2006 | EP | 1702570 B1 | 10/2010 |
| EP | 1652481 | A2 | 5/2006 | EP | 1785098 B1 | 10/2010 |
| EP | 1382303 | B1 | 6/2006 | EP | 2030578 B1 | 11/2010 |
| EP | 1253866 | B1 | 7/2006 | EP | 1627605 B1 | 12/2010 |
| EP | 1032318 | B1 | 8/2006 | EP | 1813205 B1 | 6/2011 |
| EP | 1045672 | B1 | 8/2006 | EP | 1785102 B1 | 1/2012 |
| EP | 1617768 | B1 | 8/2006 | FR | 999646 A | 2/1952 |
| EP | 1693015 | A2 | 8/2006 | FR | 1112936 A | 3/1956 |
| EP | 1400214 | B1 | 9/2006 | FR | 2598905 A1 | 11/1987 |
| EP | 1702567 | A2 | 9/2006 | FR | 2765794 A | 1/1999 |
| EP | 1129665 | B1 | 11/2006 | GB | 939929 A | 10/1963 |
| EP | 1400206 | B1 | 11/2006 | GB | 1210522 A | 10/1970 |
| EP | 1721568 | A1 | 11/2006 | GB | 1217159 A | 12/1970 |
| EP | 1256317 | B1 | 12/2006 | GB | 1339394 A | 12/1973 |
| EP | 1285633 | B1 | 12/2006 | GB | 2109241 A | 6/1983 |
| EP | 1728473 | A1 | 12/2006 | GB | 2272159 A | 5/1994 |
| EP | 1728475 | A2 | 12/2006 | GB | 2284242 A | 5/1995 |
| EP | 1479346 | B1 | 1/2007 | GB | 2336214 A | 10/1999 |
| EP | 1484024 | B1 | 1/2007 | GB | 2425903 A | 11/2006 |
| EP | 1754445 | A2 | 2/2007 | JP | 58500053 A | 1/1983 |
| EP | 1759812 | A1 | 3/2007 | JP | 61-98249 A | 5/1986 |
| EP | 1767163 | A1 | 3/2007 | JP | 63-203149 | 8/1988 |
| EP | 1769756 | A1 | 4/2007 | JP | 5-212039 A | 8/1993 |

| | | | | | | | |
|---|---|---|---|---|---|---|---|
| JP | 6007357 | A | 1/1994 | WO | WO 96/27337 | A1 | 9/1996 |
| JP | 8033641 | A | 2/1994 | WO | WO 96/31155 | A1 | 10/1996 |
| JP | 7051273 | A | 2/1996 | WO | WO 96/35464 | A1 | 11/1996 |
| JP | 8229050 | A | 9/1996 | WO | WO 96/39085 | A1 | 12/1996 |
| JP | 3-12126 | A | 1/1997 | WO | WO 96/39086 | A1 | 12/1996 |
| JP | 2000033071 | A | 2/2000 | WO | WO 96/39087 | A1 | 12/1996 |
| JP | 2000171730 | A | 6/2000 | WO | WO 96/39088 | A1 | 12/1996 |
| JP | 2000287987 | A | 10/2000 | WO | WO 96/39089 | A1 | 12/1996 |
| JP | 2000325303 | A | 11/2000 | WO | WO 97/00646 | A1 | 1/1997 |
| JP | 2001-514541 | A | 9/2001 | WO | WO 97/00647 | A1 | 1/1997 |
| JP | 2001286477 | A | 10/2001 | WO | WO 97/06582 | A1 | 2/1997 |
| JP | 2002143078 | A | 5/2002 | WO | WO 97/10763 | A1 | 3/1997 |
| JP | 2002369820 | A | 12/2002 | WO | WO 97/10764 | A1 | 3/1997 |
| JP | 2003-500153 | A | 1/2003 | WO | WO 97/11648 | A2 | 4/1997 |
| JP | 2004-344663 | | 12/2004 | WO | WO 97/11649 | A1 | 4/1997 |
| JP | 2005-028149 | A | 2/2005 | WO | WO 97/15237 | A1 | 5/1997 |
| JP | 2005505322 | T | 2/2005 | WO | WO 97/24073 | A1 | 7/1997 |
| JP | 2005103293 | A | 4/2005 | WO | WO 97/24993 | A1 | 7/1997 |
| JP | 2005131163 | A | 5/2005 | WO | WO 97/30644 | A1 | 8/1997 |
| JP | 2005131164 | A | 5/2005 | WO | WO 97/34533 | A1 | 9/1997 |
| JP | 2005131173 | A | 5/2005 | WO | WO 97/37598 | A1 | 10/1997 |
| JP | 2005131211 | A | 5/2005 | WO | WO 97/39688 | A2 | 10/1997 |
| JP | 2005131212 | A | 5/2005 | WO | WO 98/17180 | A1 | 4/1998 |
| JP | 2005137423 | A | 6/2005 | WO | WO 98/10153 | A1 | 7/1998 |
| JP | 2005152416 | A | 6/2005 | WO | WO 98/27880 | A1 | 7/1998 |
| JP | 2005-523105 | A | 8/2005 | WO | WO 98/47436 | A1 | 10/1998 |
| JP | 2005524474 | A | 8/2005 | WO | WO 99/03407 | A1 | 1/1999 |
| JP | 2006-281405 | A | 10/2006 | WO | WO 99/03408 | A1 | 1/1999 |
| RU | 2008830 | C1 | 3/1994 | WO | WO 99/03409 | A1 | 1/1999 |
| RU | 2187249 | C2 | 8/2002 | WO | WO 99/12483 | A1 | 3/1999 |
| RU | 2225170 | C2 | 3/2004 | WO | WO 99/12487 | A1 | 3/1999 |
| SU | 189517 | A | 1/1967 | WO | WO 99/12488 | A1 | 3/1999 |
| SU | 328636 | A | 9/1972 | WO | WO 99/15086 | A1 | 4/1999 |
| SU | 886900 | A1 | 12/1981 | WO | WO 99/15091 | A1 | 4/1999 |
| SU | 1009439 | A | 4/1983 | WO | WO 99/23933 | A2 | 5/1999 |
| SU | 1333319 | A2 | 8/1987 | WO | WO 99/23959 | A1 | 5/1999 |
| SU | 1377053 | A1 | 2/1988 | WO | WO 99/25261 | A1 | 5/1999 |
| SU | 1561964 | A1 | 5/1990 | WO | WO 99/29244 | A1 | 6/1999 |
| SU | 1722476 | | 3/1992 | WO | WO 99/34744 | A1 | 7/1999 |
| WO | WO 82/02824 | A1 | 9/1982 | WO | WO 99/45849 | A1 | 9/1999 |
| WO | WO 91/15157 | A1 | 10/1991 | WO | WO 99/48430 | A1 | 9/1999 |
| WO | WO 92/20295 | A1 | 11/1992 | WO | WO 99/51158 | A1 | 10/1999 |
| WO | WO 92/21300 | A1 | 12/1992 | WO | WO 00/24322 | A1 | 5/2000 |
| WO | WO 93/08755 | A1 | 5/1993 | WO | WO 00/24330 | A1 | 5/2000 |
| WO | WO 93/13718 | A1 | 7/1993 | WO | WO 00/41638 | A1 | 7/2000 |
| WO | WO 93/14690 | A1 | 8/1993 | WO | WO 00/48506 | A1 | 8/2000 |
| WO | WO 93/15648 | A1 | 8/1993 | WO | WO 00/53112 | A2 | 9/2000 |
| WO | WO 93/15850 | A1 | 8/1993 | WO | WO 00/54653 | A1 | 9/2000 |
| WO | WO 93/19681 | A1 | 10/1993 | WO | WO 00/57796 | A1 | 10/2000 |
| WO | WO 94/00060 | A1 | 1/1994 | WO | WO 00/64365 | A1 | 11/2000 |
| WO | WO 94/11057 | A1 | 5/1994 | WO | WO 00/72765 | A1 | 12/2000 |
| WO | WO 94/12108 | A1 | 6/1994 | WO | WO 00/72766 | A1 | 12/2000 |
| WO | WO 94/18893 | A1 | 9/1994 | WO | WO 01/03587 | A1 | 1/2001 |
| WO | WO 94/22378 | A1 | 10/1994 | WO | WO 01/05702 | A1 | 1/2001 |
| WO | WO 94/23659 | A1 | 10/1994 | WO | WO 01/10482 | A1 | 2/2001 |
| WO | WO 95/02369 | A1 | 1/1995 | WO | WO 01/35845 | A1 | 5/2001 |
| WO | WO 95/03743 | A1 | 2/1995 | WO | WO 01/62162 | A1 | 6/2001 |
| WO | WO 95/06817 | A1 | 3/1995 | WO | WO 01/62164 | A2 | 6/2001 |
| WO | WO 95/09576 | A1 | 4/1995 | WO | WO 01/54594 | A1 | 8/2001 |
| WO | WO 95/09577 | A1 | 4/1995 | WO | WO 01/58371 | A1 | 8/2001 |
| WO | WO 95/14436 | A1 | 6/1995 | WO | WO 01/62158 | A2 | 8/2001 |
| WO | WO 95/17855 | A1 | 7/1995 | WO | WO 01/62161 | A1 | 8/2001 |
| WO | WO 95/18383 | A1 | 7/1995 | WO | WO 01/62169 | A2 | 8/2001 |
| WO | WO 95/18572 | A1 | 7/1995 | WO | WO 01/78605 | A2 | 10/2001 |
| WO | WO 95/19739 | A1 | 7/1995 | WO | WO 01/91646 | A1 | 12/2001 |
| WO | WO 95/20360 | A1 | 8/1995 | WO | WO 02/07608 | A2 | 1/2002 |
| WO | WO 95/23557 | A1 | 9/1995 | WO | WO 02/07618 | A1 | 1/2002 |
| WO | WO 95/24865 | A1 | 9/1995 | WO | WO 02/17799 | A1 | 3/2002 |
| WO | WO 95/25471 | A3 | 9/1995 | WO | WO 02/19920 | A1 | 3/2002 |
| WO | WO 95/26562 | A1 | 10/1995 | WO | WO 02/19932 | A1 | 3/2002 |
| WO | WO 95/29639 | A1 | 11/1995 | WO | WO 02/30297 | A2 | 4/2002 |
| WO | WO 96/04858 | A1 | 2/1996 | WO | WO 02/32322 | A2 | 4/2002 |
| WO | WO 96/19151 | A1 | 6/1996 | WO | WO 02/36028 | A1 | 5/2002 |
| WO | WO 96/19152 | A1 | 6/1996 | WO | WO 02/43571 | A2 | 6/2002 |
| WO | WO 96/20652 | A1 | 7/1996 | WO | WO 02/058568 | A1 | 8/2002 |
| WO | WO 96/21119 | A1 | 7/1996 | WO | WO 02/060328 | A1 | 8/2002 |
| WO | WO 96/22055 | A1 | 7/1996 | WO | WO 02/067785 | A2 | 9/2002 |
| WO | WO 96/23448 | A1 | 8/1996 | WO | WO 02/098302 | A1 | 12/2002 |
| WO | WO 96/24301 | A1 | 8/1996 | WO | WO 03/000138 | A2 | 1/2003 |

| | | | |
|---|---|---|---|
| WO | WO 03/001320 A2 | 1/2003 |
| WO | WO 03/013363 A1 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/088845 A2 | 10/2003 |
| WO | WO 03/090630 A2 | 11/2003 |
| WO | WO 03/094745 A1 | 11/2003 |
| WO | WO 03/094746 A1 | 11/2003 |
| WO | WO 03/094747 A1 | 11/2003 |
| WO | WO 031094743 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/011037 A2 | 2/2004 |
| WO | WO 2004/019769 A1 | 3/2004 |
| WO | WO 2004/021868 A2 | 3/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A2 | 4/2004 |
| WO | WO 2004/032763 A2 | 4/2004 |
| WO | WO 2004/034675 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078050 A2 | 9/2004 |
| WO | WO 2004/078051 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/027014 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/131110 A2 | 11/2007 |
| WO | WO 2007/137304 A2 | 11/2007 |
| WO | WO 2007/142625 A2 | 12/2007 |
| WO | WO 2007/147439 A1 | 12/2007 |
| WO | WO 2008/021969 A2 | 2/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/070763 A1 | 6/2008 |
| WO | WO 2008/089404 A2 | 7/2008 |
| WO | WO 2008/109125 A1 | 9/2008 |
| WO | WO 2010/063795 A1 | 6/2010 |
| WO | WO 2012/044844 A2 | 4/2012 |

OTHER PUBLICATIONS

U.S. Appl. No. 12/031,556, filed Feb. 14, 2008.
U.S. Appl. No. 12/031,567, filed Feb. 14, 2008.
U.S. Appl. No. 12/031,573, filed Feb. 14, 2008.
U.S. Appl. No. 12/031,580, filed Feb. 14, 2008.
European Search Report, Application No. 09250391.1, dated Jul. 3, 2009 (8 pages).
Dicsclosed Anonymously, "Motor-Driven Surgical Stapler Improvements," Research Disclosure Database No. 526041, Published: Feb. 2008.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
The Sodem Aseptic Battery Transfer Kit, Sodem Systems, (2000), 3 pages.
"Biomedical Coatings," Fort Wayne Metals, Research Products Corporation, obtained online at www.fwmetals.com on Jun. 21, 2010 (1 page).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
Datasheet for Panasonic TK Relays Ultra Low Profile 2 A Polarized Relay, Copyright Matsushita Electric Works, Ltd. (Known of at least as early as Aug. 17, 2010), 5 pages.
ASTM procedure D2240-00, "Standard Test Method for Rubber Property-Durometer Hardness," (Published Aug. 2000).
ASTM procedure D2240-05. "Standard Test Method for Rubber-Durometer Hardness," (Published Apr. 2010).
U.S. Appl. No. 12/031,368, filed Feb. 14, 2008.
U.S. Appl. No. 13/118,241, filed May 27, 2011.
U.S. Appl. No. 13/488,903, filed Jun. 5. 2012.
U.S. Appl. No, 13/310,107, filed Dec. 2, 2011.
U.S. Appl. No. 13/369,561, filed Feb. 9, 2012.
U.S. Appl. No. 13/369,629, filed Feb. 9, 2012.
U.S. Appl. No. 13/372,195, filed Feb. 13, 2012.
U.S. Appl. No. 13/486,175, filed Jun. 1, 2012.
U.S. Appl. No. 13/480,263, filed May 24, 2012.
European Examination Report, Application No. 09250391.1, dated Feb. 10, 2010 (5 pages).

* cited by examiner

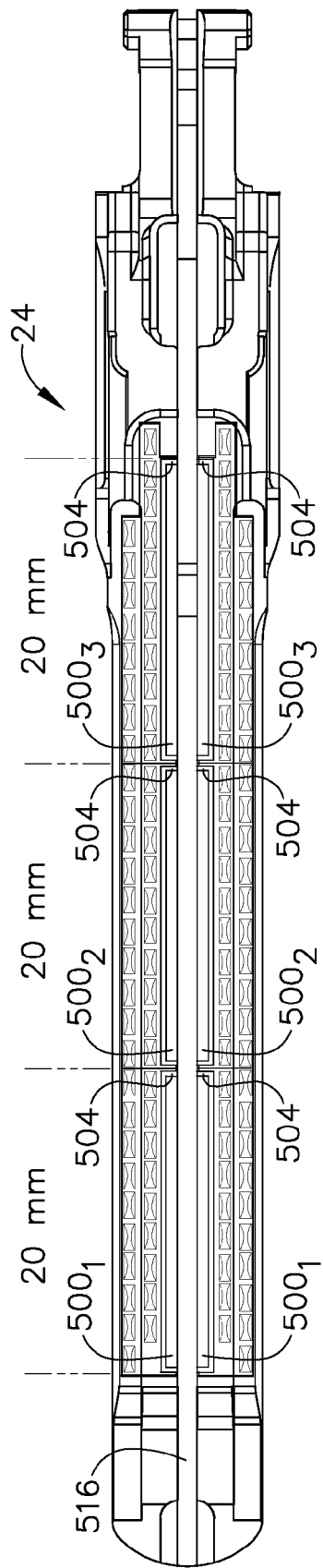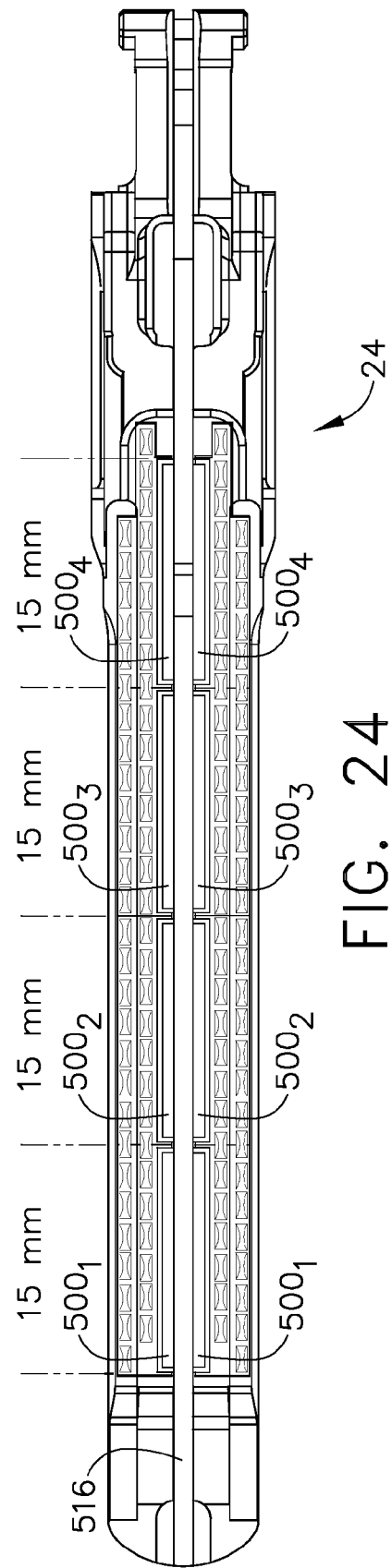

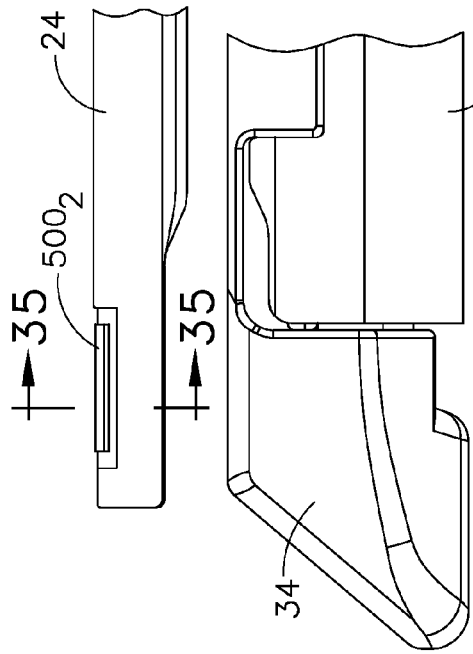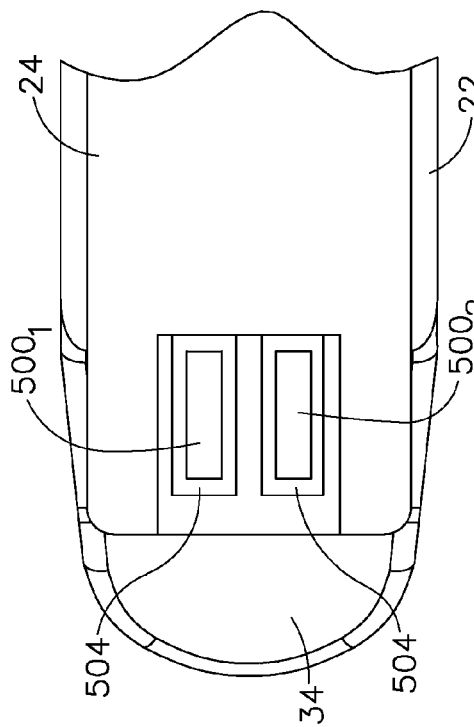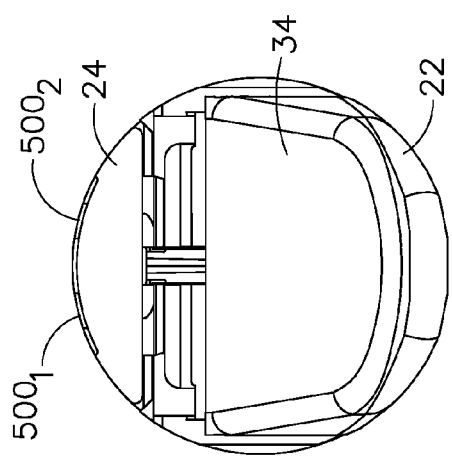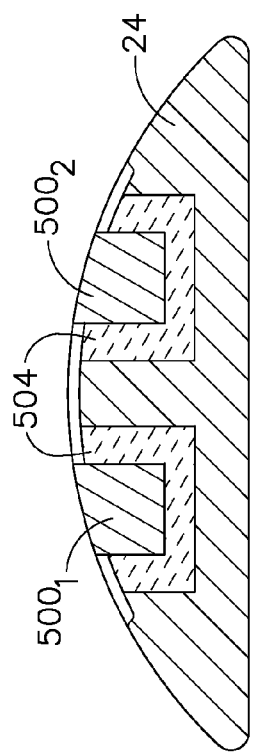
FIG. 34
FIG. 36
FIG. 33
FIG. 35

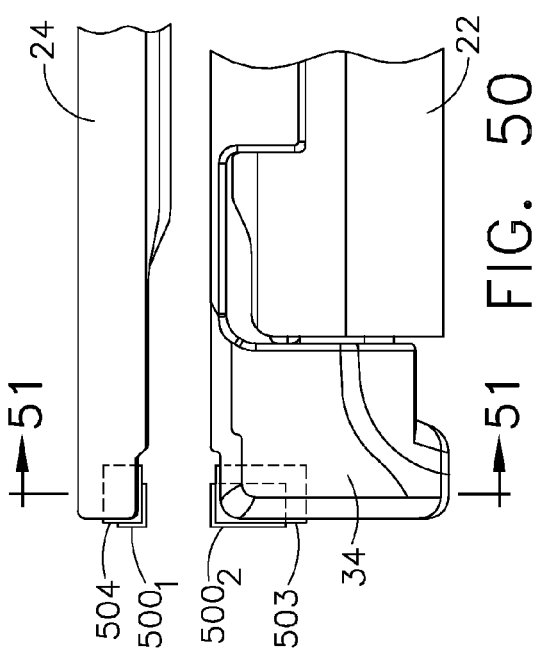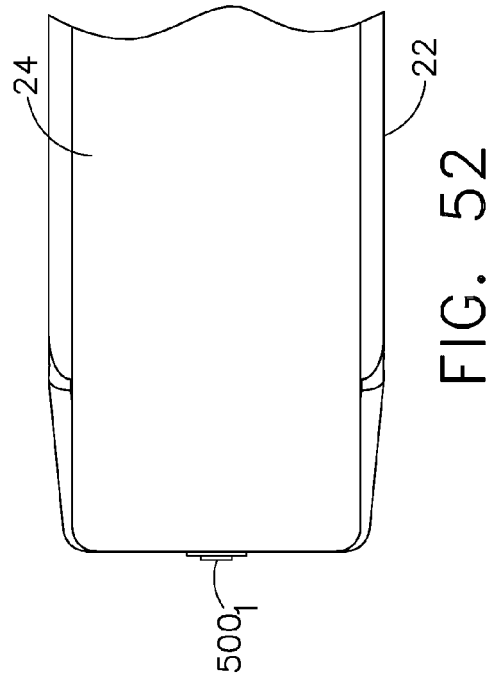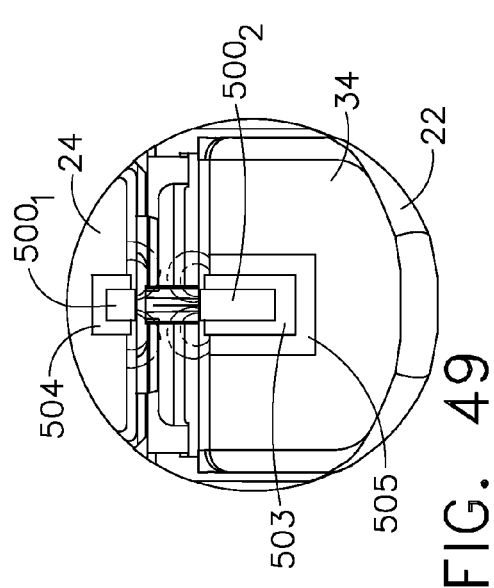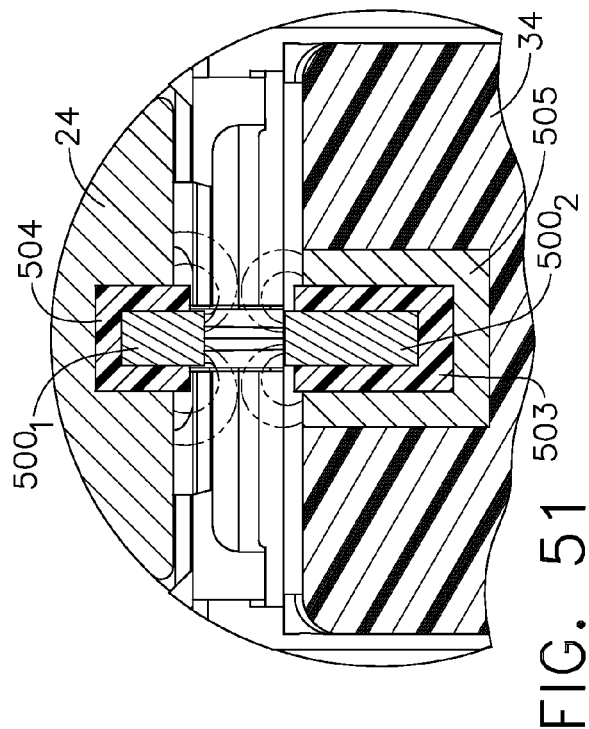

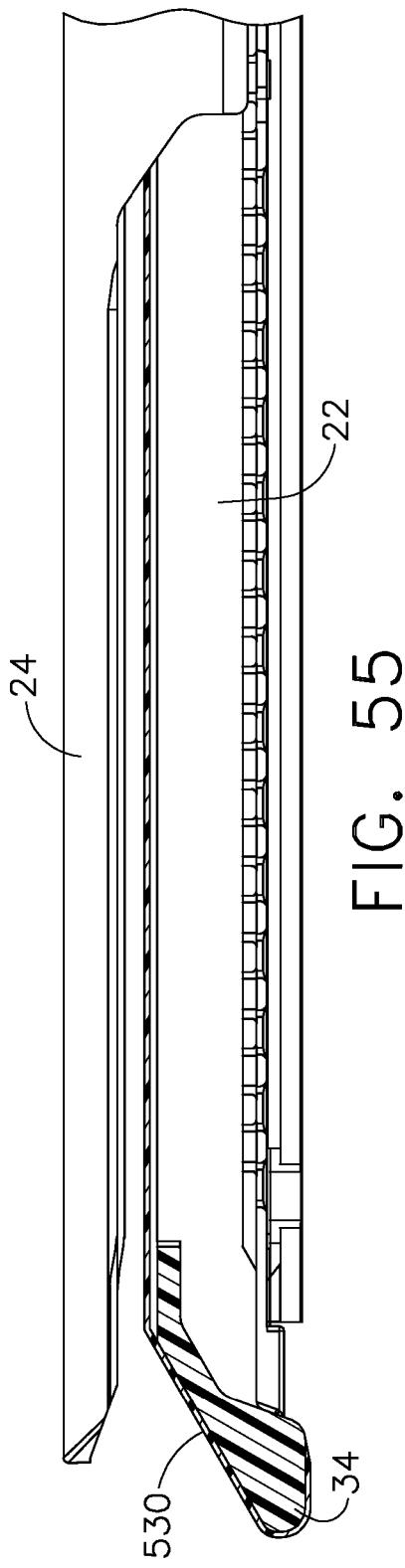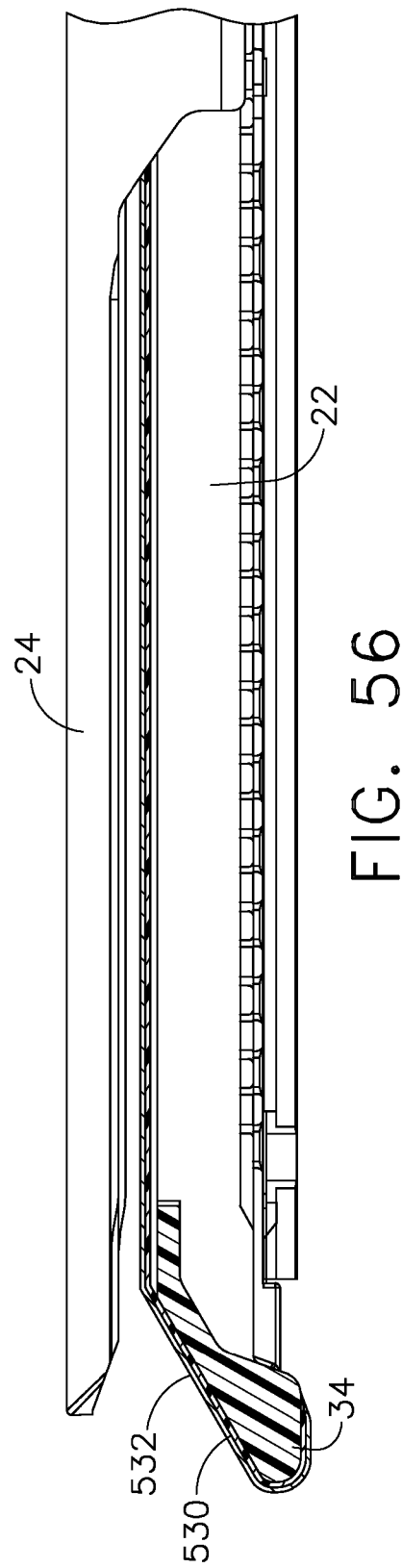

MOTORIZED SURGICAL CUTTING AND FASTENING INSTRUMENT HAVING A MAGNETIC DRIVE TRAIN TORQUE LIMITING DEVICE

CROSS-REFERENCE TO RELATED APPLICATIONS

The present application is related to and incorporates by reference the following concurrently filed applications:

Motorized Surgical Cutting and Fastening Instrument, U.S. patent application Ser. No. 12/031,556;

Motorized Surgical Cutting and Fastening Instrument Having Handle Based Power Source, U.S. patent application Ser. No. 12/031,567;

Surgical Cutting and Fastening Instrument Having RF Electrodes, U.S. patent application Ser. No. 12/031,573; and Motorized Cutting and Fastening Instrument Having Control Circuit for Optimizing Battery Usage, U.S. patent application Ser. No. 12/031,580.

BACKGROUND

Surgical staplers have been used in the prior art to simultaneously make a longitudinal incision in tissue and apply lines of staples on opposing sides of the incision. Such instruments commonly include a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. Such instruments typically include a plurality of reciprocating wedges that, when driven distally, pass through openings in the staple cartridge and engage drivers supporting the staples to effect the firing of the staples toward the anvil.

An example of a surgical stapler suitable for endoscopic applications is described in published U.S. patent application Pub. No. 2004/0232196 A1, entitled, "Surgical stapling instrument having separate distinct closing and firing systems," the disclosure of which is herein incorporated by reference. In use, a clinician is able to close the jaw members of the stapler upon tissue to position the tissue prior to firing. Once the clinician has determined that the jaw members are properly gripping tissue, the clinician can fire the surgical stapler, thereby severing and stapling the tissue. The simultaneous severing and stapling steps avoid complications that may arise when performing such actions sequentially with different surgical tools that respectively only sever or staple.

In addition, it is also known in the prior art to include electrodes in the end effector that can be used to emit/receive RF energy to form a hemostatic line along the cut line. U.S. Pat. No. 5,403,312, entitled "Electrosurgical hemostatic device" (hereinafter the "'312 patent"), which is incorporated herein by reference, discloses an electrosurgical instrument with an end effector that compresses tissue between one pole (or electrode) of a bipolar energy source on one interfacing surface, and a second pole (or electrode) on a second interfacing surface. The RF energy applied through the compressed tissue in the end effector, which cauterizes the tissue. The end effector described in the '312 patent also includes staples for stapling the tissue compressed in the end effector.

Motor-powered surgical cutting and fastening instruments, where the motor powers the cutting instrument, are also known in the prior art, such as described in published U.S. application Pub. No. 2007/0175962 A1, entitled "Motor-driven surgical cutting and fastening instrument with tactile position feedback," which is incorporated herein by reference.

SUMMARY

In one general aspect, embodiments of the present invention are directed to surgical cutting and fastening instruments. The instruments may be endoscopic instruments, such as linear endocutters or circular cutters, or laparoscopic instruments. The instruments may be comprised of staples and/or RF electrodes for fastening tissue clamped in the end effector.

Several embodiments disclosed herein are pertinent to cordless motor-powered instruments. The instruments may be powered by a power pack comprising a DC power source, such as one or more series-connected battery cells. A cell selection switch may control how many of the battery cells are being used to power the motor at a given time to control the power available to the motor. This allows the operator of the instrument to have greater control over both the speed and the power of the motor. In another embodiment, the instrument may comprise a power regulator, including, for example, a DC-to-DC converter, that regulates the voltage supplied to the motor. Further, the voltage set point for the power regulator could be set so that the voltage delivered from the power source is less than the voltage at which the power source delivers maximum power. That way, the power source (e.g., a number of series-connected battery cells) could operate on the "left" or increasing side of the power curve, so that increases in power would be available.

In addition, according to various embodiments, the power source may comprise secondary accumulator devices, such as rechargeable batteries or supercapacitors. Such secondary accumulator devices may be charged repeatably by replaceable batteries. A charge management circuit may control the charging of the secondary accumulator devices and provide various status signals, such as an alert, when the charging of the secondary accumulator devices is complete.

In other embodiment, a power pack comprising the secondary accumulator devices may be removable from the instrument and connectable to a remote charger base. The charger base may charge the secondary accumulator devices, such as from the AC electrical mains or a battery. The charger base may also comprise a processor and memory unit. Data stored in a memory of the removable power pack may be downloaded to the charger base, from which it may be uploaded for later use and analysis, such as by the user (e.g., physician), the manufacturer or distributor of the instrument, etc. The data may comprise operating parameters, such as charge cycle information, as well as ID values for various replaceable components of the instrument, such as the staple cartridge.

In addition, the instrument may comprise a torque-limiting device to limit the torque supplied by the motor, to limit thereby actuation forces that may damage components of the instrument. According to various embodiments, the torque-limiting devices may be an electromagnetic or permanent magnet, or mechanical clutch devices connected (either directly or indirectly) to the output pole of the motor.

In another general aspect, the present invention is directed to RF instruments (i.e., surgical cutting and fastening instruments with electrodes at the end effector for applying RF energy to the tissue held by the end effector) with new types of electrode configurations. In general, the new electrode configurations include combinations of smaller active electrodes and larger return electrodes. The smaller active electrodes are used to concentrate the therapeutic energy at the tissue, while the larger return electrodes preferentially are used to complete the circuit with minimal impact on that tissue interface. The return electrodes typically have greater mass and thereby are able to stay cooler during electrosurgical application.

In addition, the end effector, according to various embodiments, may comprise a number of co-linear, segmented active electrodes. The segmented electrodes could be energized synchronously or, more preferably, in sequence. Activating the segmented electrodes in sequence provides the advantages of (1) decreased instantaneous power requirements due to a smaller targeted area of tissue coagulation and (2) allowing other segments to fire if one is shorted out.

In addition, a number of mechanisms for activating the RF electrodes and for articulating the end effector are disclosed herein.

FIGURES

Various embodiments of the present invention are described herein by way of example in conjunction with the following figures, wherein.

Figure 57:
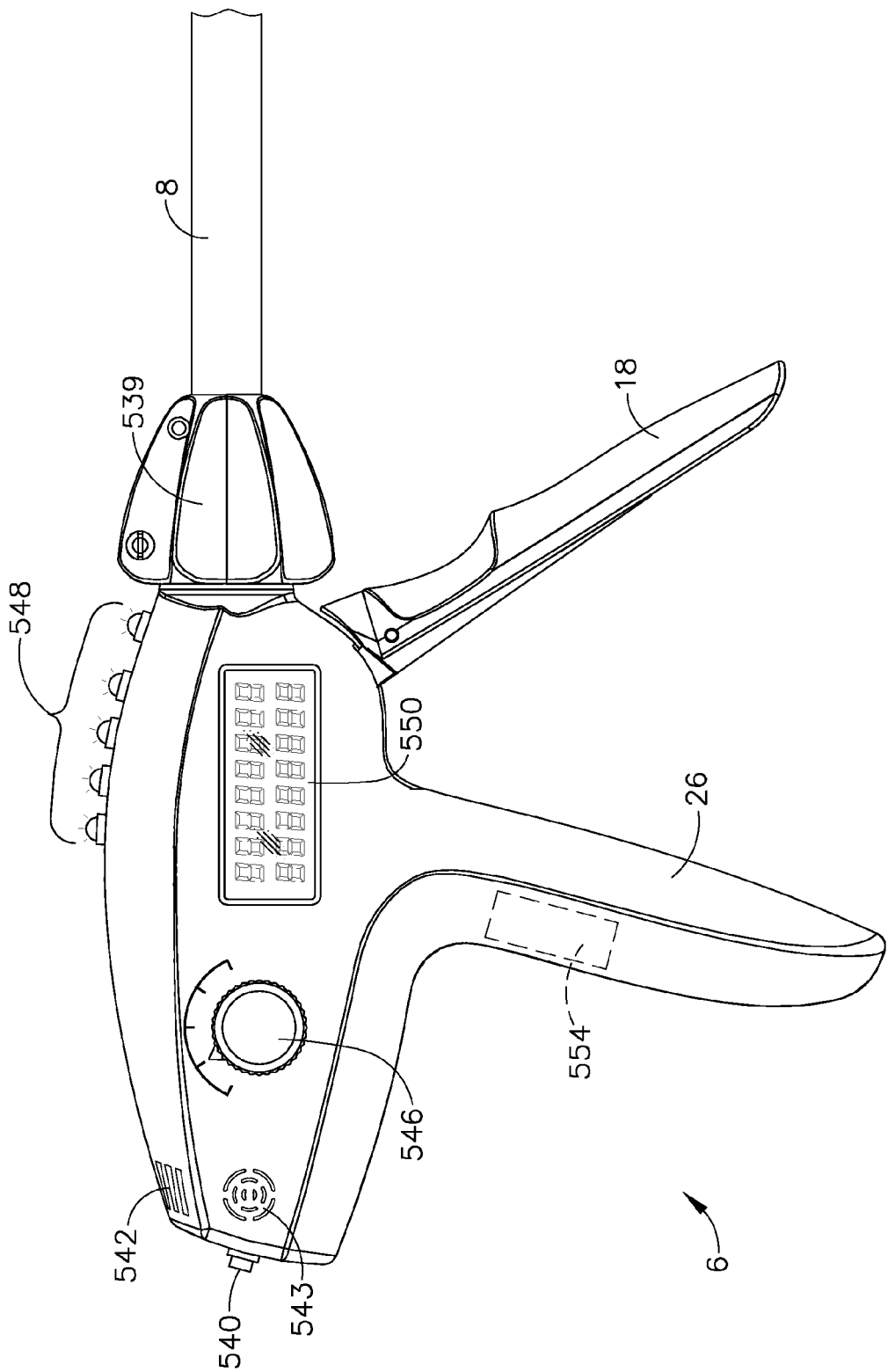
Figure 58:
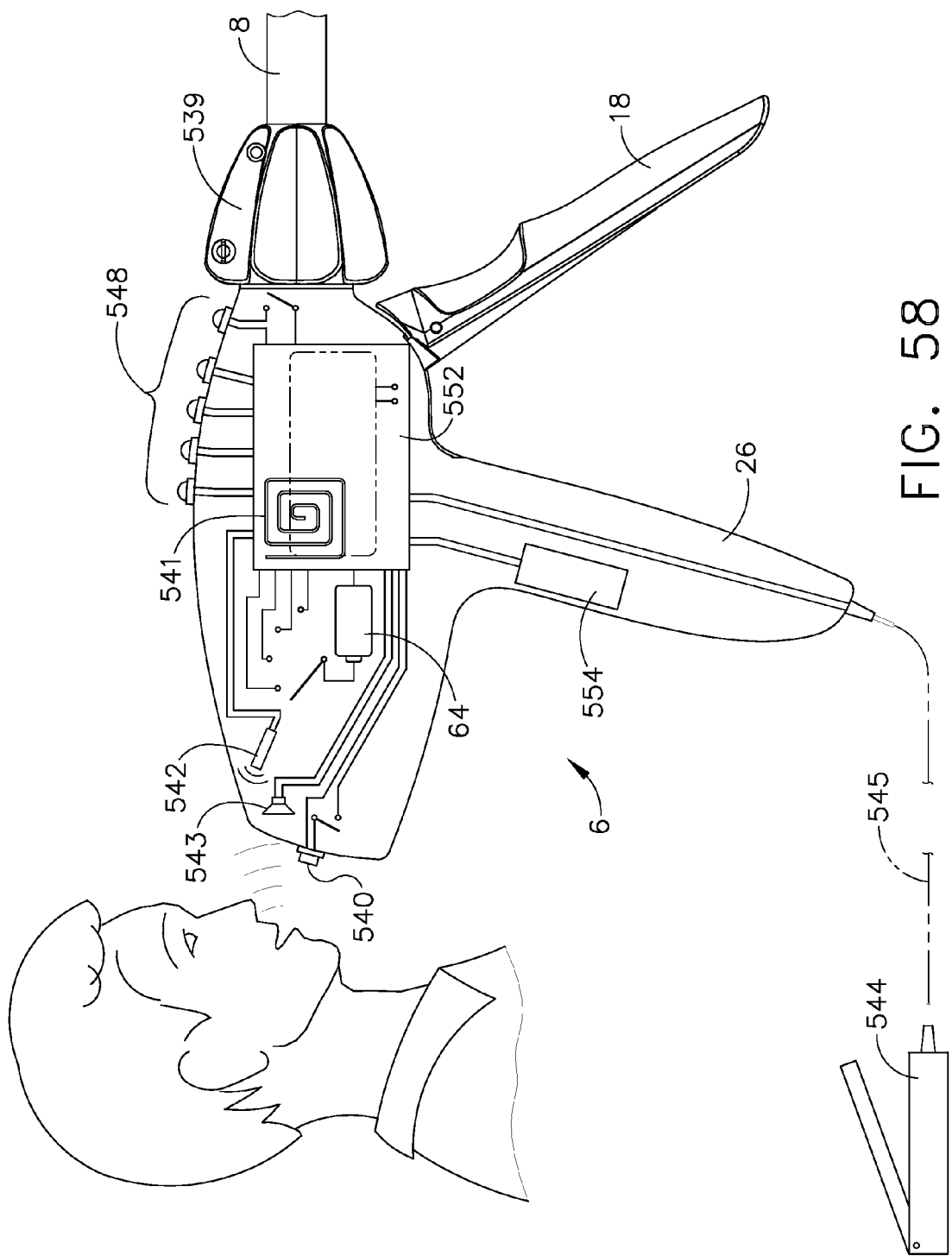
Figure 67:
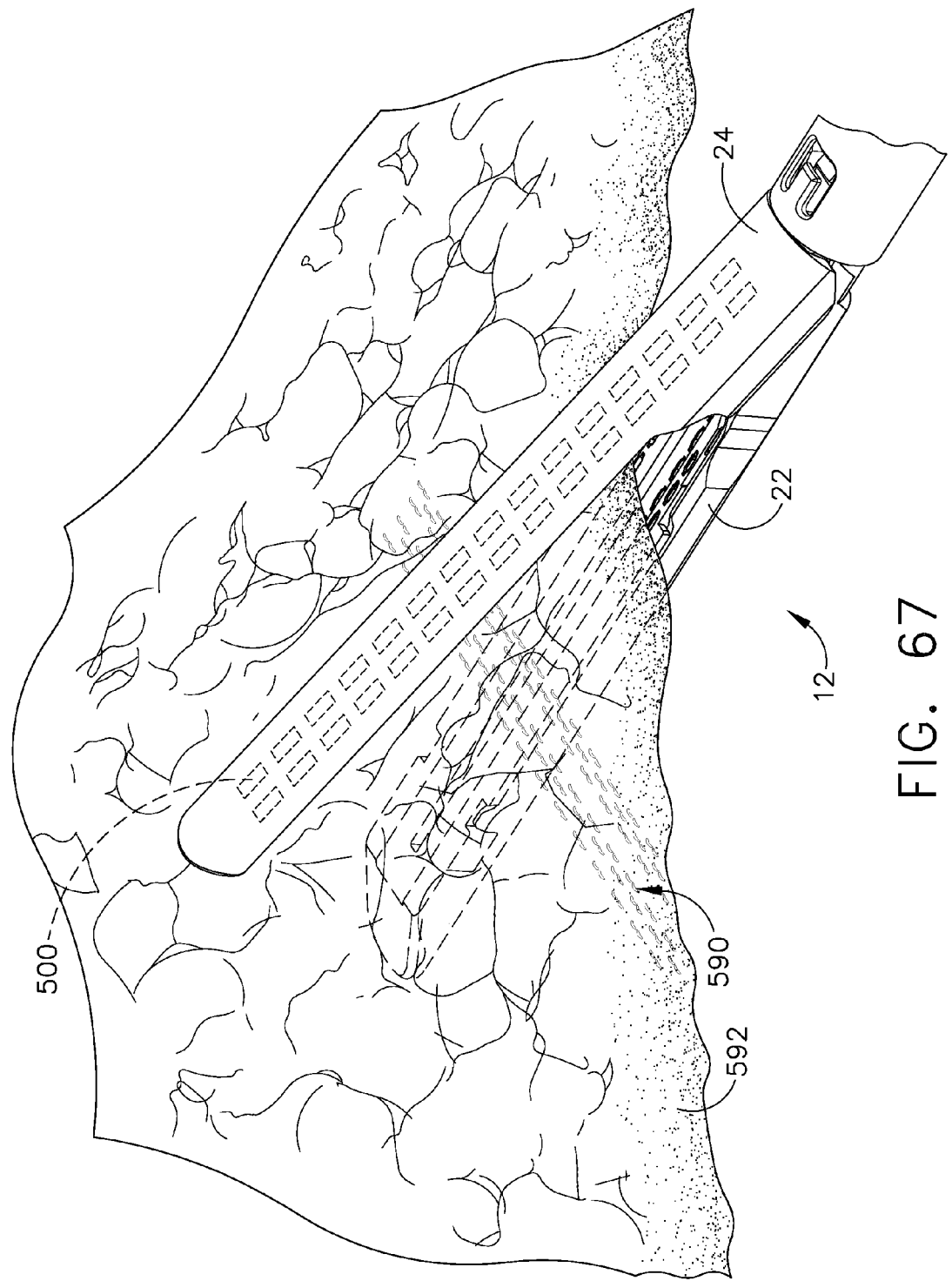
Figure 69:
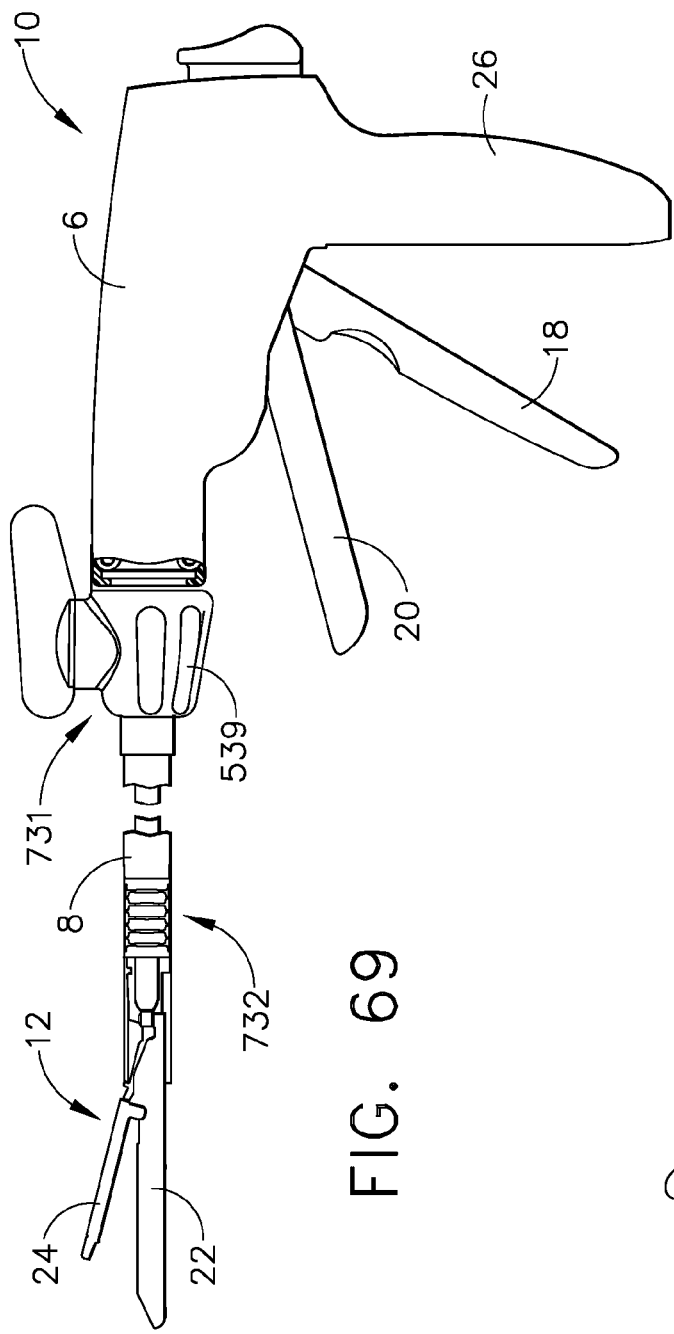
Figure 70:
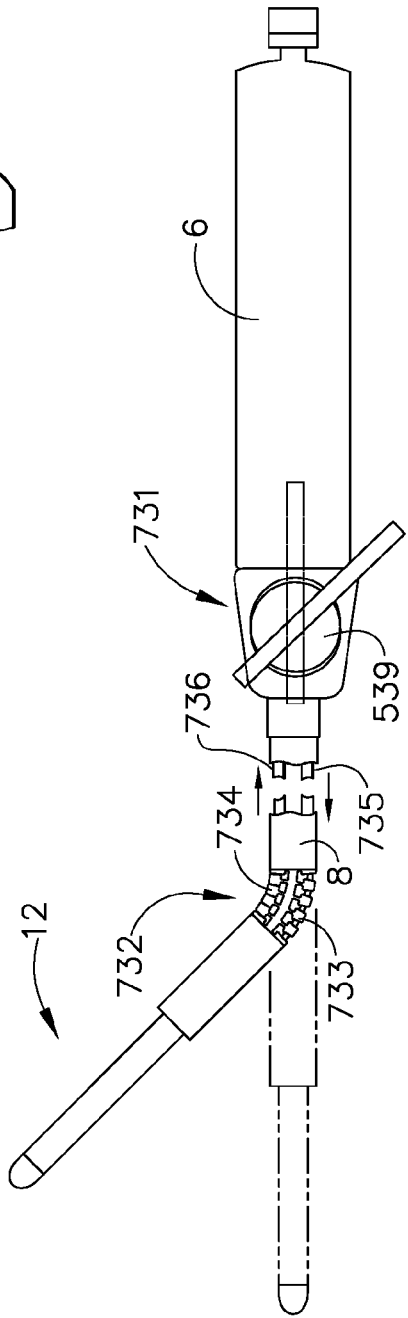

FIGS. 23-25, 27-28, and 59 are views of the lower surface of the anvil of the instrument according to various embodiments of the present invention;

FIGS. 26, 53, 54, and 68 are cross-sectional front views of the end effector according to various embodiments of the present invention;

FIGS. 29-32 show an embodiment of the end effector having RF electrodes according to various embodiments of the present invention;

FIGS. 33-36 show another embodiment of the end effector having RF electrodes according to various embodiments of the present invention;

FIGS. 37-40 show another embodiment of the end effector having RF electrodes according to various embodiments of the present invention;

FIGS. 41-44 show another embodiment of the end effector having RF electrodes according to various embodiments of the present invention;

FIGS. 45-48 show another embodiment of the end effector having RF electrodes according to various embodiments of the present invention;

FIGS. 49-52 show another embodiment of the end effector having RF electrodes according to various embodiments of the present invention;

FIGS. 55 and 56 show side views of the end effector according to various embodiments of the present invention;

FIG. 57 is a diagram of the handle of the instrument according to another embodiment of the present invention;

FIG. 58 is a cut-away view of the handle of the embodiment of FIG. 57 according to various embodiments of the present invention;

FIGS. 60-66 illustrate a multi-layer circuit board according to various embodiments of the present invention;

FIG. 67 is a diagram illustrating an end effector according to various embodiments of the present invention; and FIGS. 69 and 70 are diagram of an instrument comprising a flexible neck assembly according to various embodiments of the present invention.

DESCRIPTION

Figure 1:
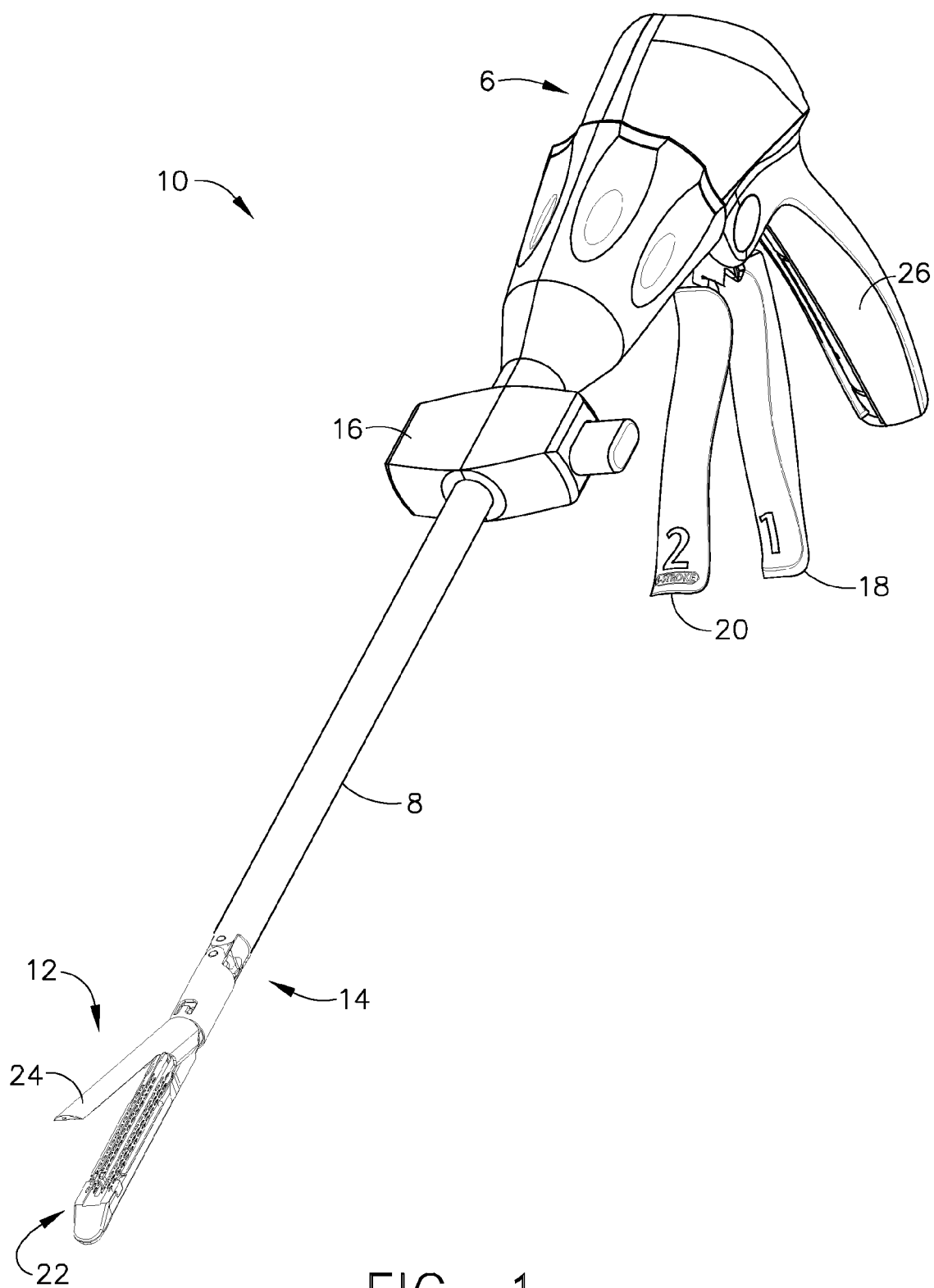
FIGS. 1 and 2 are perspective views of a surgical cutting and fastening instrument according to various embodiments of the present invention.
Figure 2:
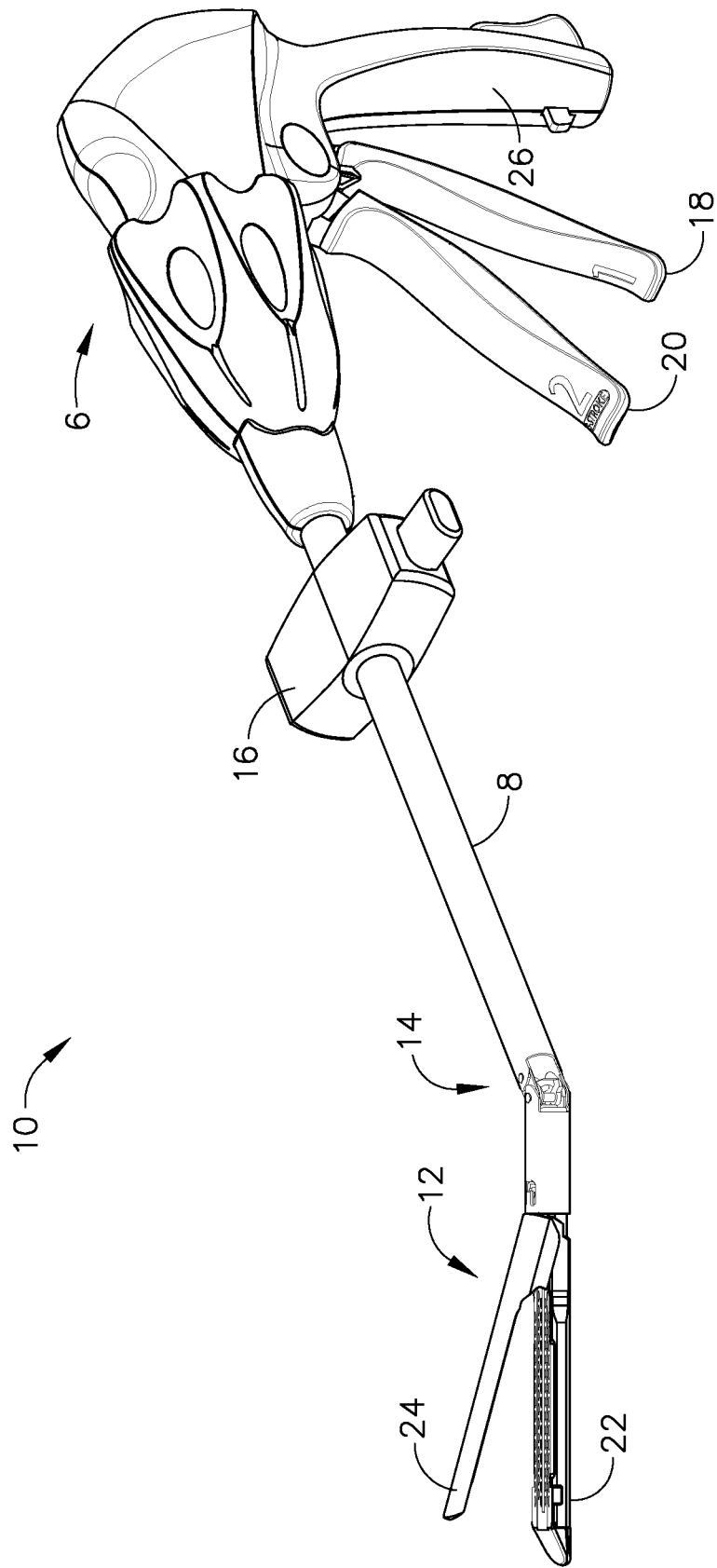

FIGS. 1 and 2 depict a surgical cutting and fastening instrument 10 according to various embodiments of the present invention. The illustrated embodiment is an endoscopic instrument and, in general, the embodiments of the instrument 10 described herein are endoscopic surgical cutting and fastening instruments. It should be noted, however, that according to other embodiments of the present invention, the instrument may be a non-endoscopic surgical cutting and fastening instrument, such as a laparoscopic instrument.

The surgical instrument 10 depicted in FIGS. 1 and 2 comprises a handle 6, a shaft 8, and an articulating end effector 12 pivotally connected to the shaft 8 at an articulation pivot 14. An articulation control 16 may be provided adjacent to the handle 6 to effect rotation of the end effector 12 about the articulation pivot 14. In the illustrated embodiment, the end effector 12 is configured to act as an endocutter for clamping, severing and stapling tissue, although, in other embodiments, different types of end effectors may be used, such as end effectors for other types of surgical devices, such as graspers, cutters, staplers, clip appliers, access devices, drug/gene therapy devices, ultrasound, RF or laser devices, etc. More details regarding RF devices may be found in the '312 patent.

The handle 6 of the instrument 10 may include a closure trigger 18 and a firing trigger 20 for actuating the end effector 12. It will be appreciated that instruments having end effectors directed to different surgical tasks may have different numbers or types of triggers or other suitable controls for operating the end effector 12. The end effector 12 is shown separated from the handle 6 by a preferably elongate shaft 8. In one embodiment, a clinician or operator of the instrument 10 may articulate the end effector 12 relative to the shaft 8 by utilizing the articulation control 16, as described in more detail in published U.S. patent application Pub. No. 2007/0158385 A1, entitled "Surgical Instrument Having An Articulating End Effector," by Geoffrey C. Hueil et al., which is incorporated herein by reference.

The end effector 12 includes in this example, among other things, a staple channel 22 and a pivotally translatable clamping member, such as an anvil 24, which are maintained at a spacing that assures effective stapling and severing of tissue clamped in the end effector 12. The handle 6 includes a pistol grip 26 towards which a closure trigger 18 is pivotally drawn by the clinician to cause clamping or closing of the anvil 24 toward the staple channel 22 of the end effector 12 to thereby clamp tissue positioned between the anvil 24 and channel 22. The firing trigger 20 is farther outboard of the closure trigger 18. Once the closure trigger 18 is locked in the closure position as further described below, the firing trigger 20 may rotate slightly toward the pistol grip 26 so that it can be reached by the operator using one hand. Then the operator may pivotally draw the firing trigger 20 toward the pistol grip 12 to cause the stapling and severing of clamped tissue in the end effector 12. In other embodiments, different types of clamping members besides the anvil 24 could be used, such as, for example, an opposing jaw, etc.

It will be appreciated that the terms "proximal" and "distal" are used herein with reference to a clinician gripping the handle 6 of an instrument 10. Thus, the end effector 12 is distal with respect to the more proximal handle 6. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

Figure 7:
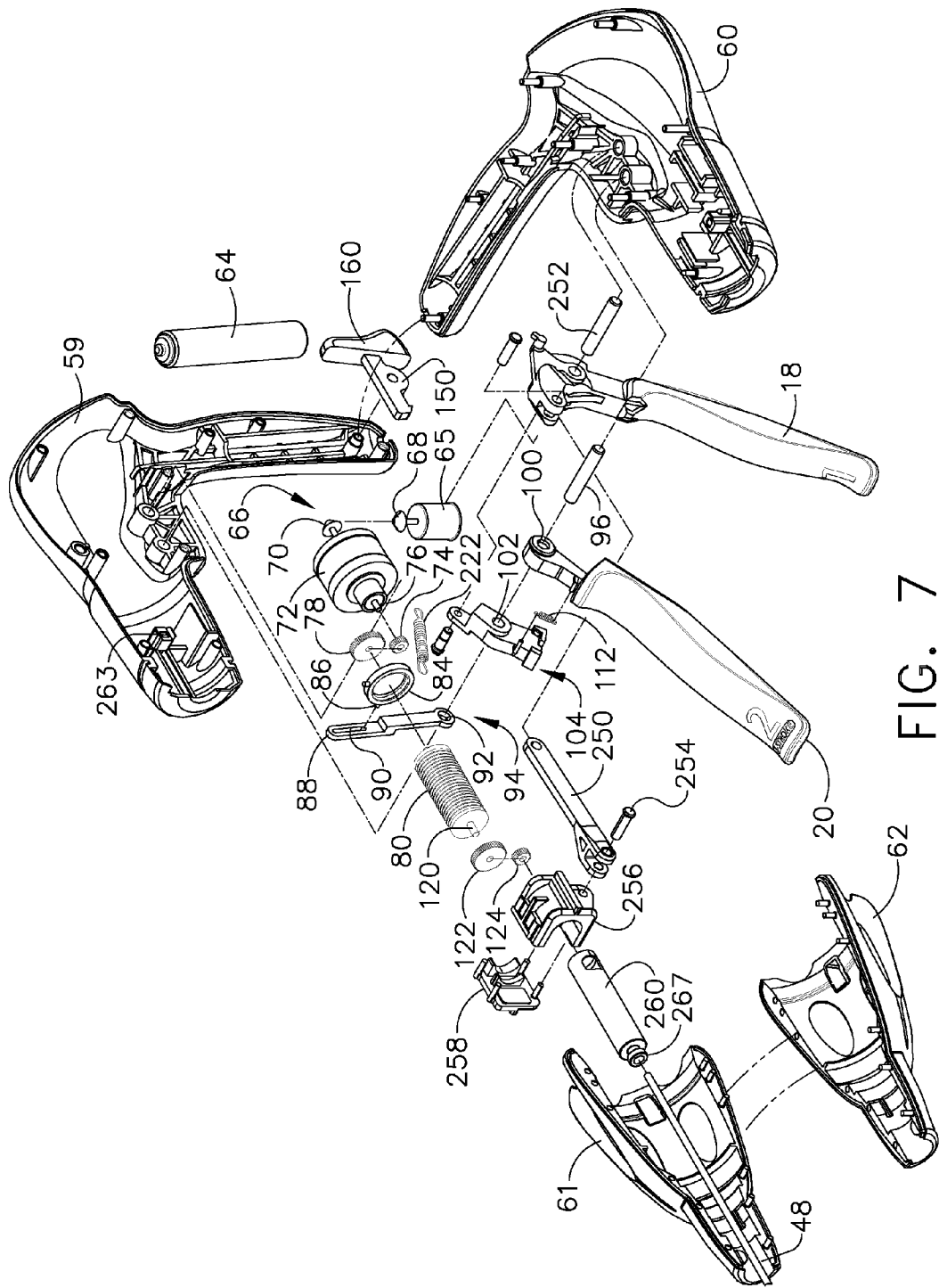
FIG. 7 is an exploded view of the handle of the instrument according to various embodiments of the present invention.

The closure trigger 18 may be actuated first. Once the clinician is satisfied with the positioning of the end effector 12, the clinician may draw back the closure trigger 18 to its fully closed, locked position proximate to the pistol grip 26. The firing trigger 20 may then be actuated. The firing trigger 20 returns to the open position (shown in FIGS. 1 and 2) when the clinician removes pressure, as described more fully below. A release button on the handle 6, when depressed may release the locked closure trigger 18. The release button may be implemented in various forms such as, for example, as a slide release button 160 shown in FIG. 7 or any of the mechanisms described in published U.S. Patent Application Publication No. 2007/0175955 A1, which is incorporated herein by reference.

Figure 3:
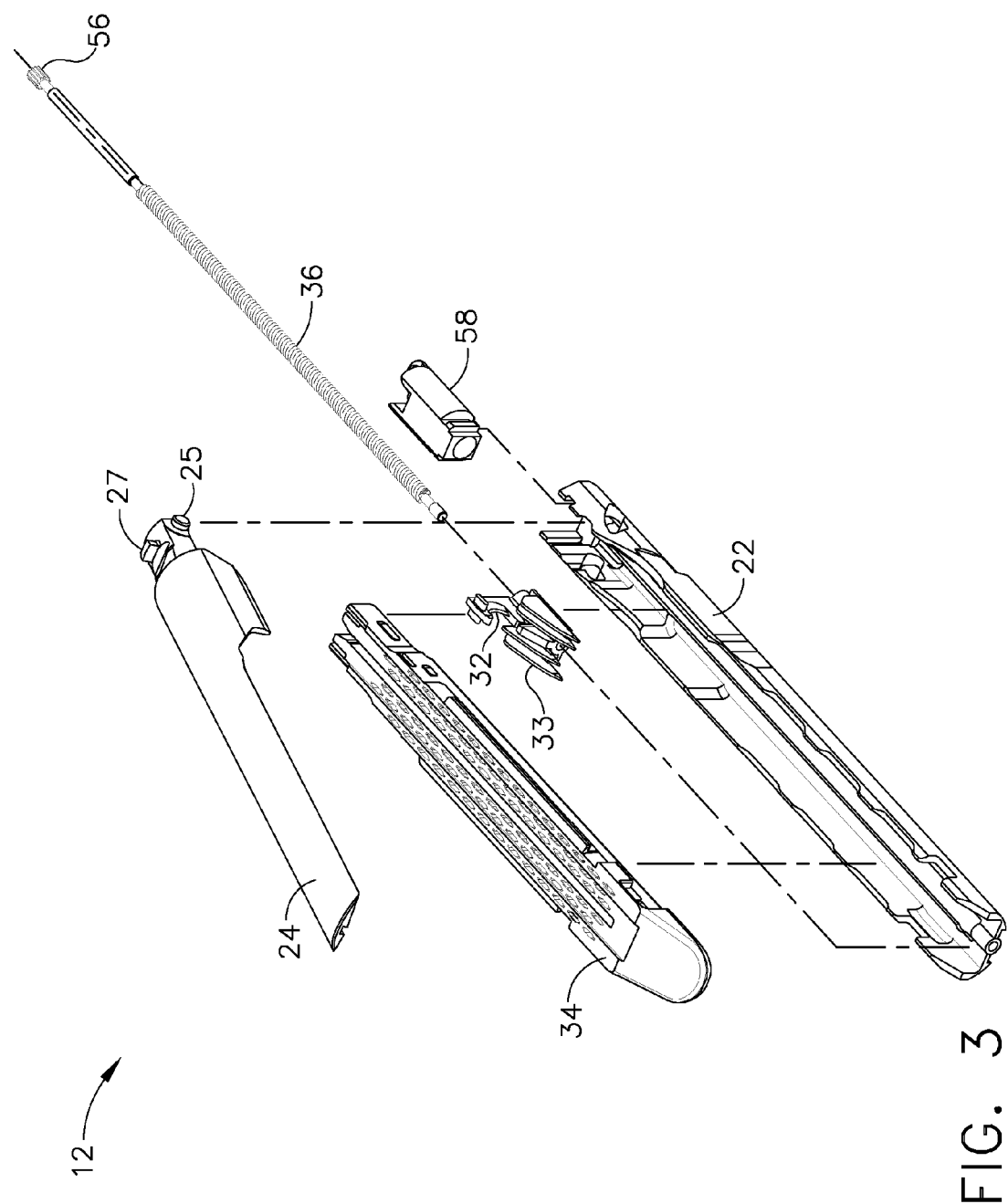
FIGS. 3-5 are exploded views of an end effector and shaft of the instrument according to various embodiments of the present invention.

FIG. 3 is an exploded view of the end effector 12 according to various embodiments. As shown in the illustrated embodiment, the end effector 12 may include, in addition to the previously mentioned channel 22 and anvil 24, a cutting instrument 32, a sled 33, a staple cartridge 34 that is removably seated in the channel 22, and a helical screw shaft 36. The cutting instrument 32 may be, for example, a knife. The anvil 24 may be pivotably opened and closed at a pivot point 25 connected to the proximate end of the channel 22. The anvil 24 may also include a tab 27 at its proximate end that is inserted into a component of the mechanical closure system (described further below) to open and close the anvil 24. When the closure trigger 18 is actuated, that is, drawn in by a user of the instrument 10, the anvil 24 may pivot about the pivot point 25 into the clamped or closed position. If clamping of the end effector 12 is satisfactory, the operator may actuate the firing trigger 20, which, as explained in more detail below, causes the knife 32 and sled 33 to travel longitudinally along the channel 22, thereby cutting tissue clamped within the end effector 12. The movement of the sled 33 along the channel 22 causes the staples of the staple cartridge 34 to be driven through the severed tissue and against the closed anvil 24, which turns the staples to fasten the severed tissue. In various embodiments, the sled 33 may be an integral component of the cartridge 34. U.S. Pat. No. 6,978,921, entitled "Surgical stapling instrument incorporating an E-beam firing mechanism," which is incorporated herein by reference, provides more details about such two-stroke cutting and fastening instruments. The sled 33 may be part of the cartridge 34, such that when the knife 32 retracts following the cutting operation, the sled 33 does not retract.

It should be noted that although the embodiments of the instrument 10 described herein employ an end effector 12 that staples the severed tissue, in other embodiments different techniques for fastening or sealing the severed tissue may be used. For example, end effectors that use RF energy or adhesives to fasten the severed tissue may also be used. U.S. Pat. No. 5,709,680 entitled "Electrosurgical Hemostatic Device" to Yates et al., and U.S. Pat. No. 5,688,270 entitled "Electrosurgical Hemostatic Device with Recessed and/or Offset Electrodes" to Yates et al., which are incorporated herein by reference, disclose an endoscopic cutting instrument that uses RF energy to seal the severed tissue. Published U.S. patent application Pub. No. 2007/0102453 A1 to Jerome R. Morgan, et al. and published U.S. patent application Pub. No. 2007/0102452 A1 to Frederick E. Shelton, IV, et al., which are also incorporated herein by reference, disclose endoscopic cutting instruments that use adhesives to fasten the severed tissue. Accordingly, although the description herein refers to cutting/stapling operations and the like below, it should be recognized that this is an exemplary embodiment and is not meant to be limiting. Other tissue-fastening techniques may also be used.

Figure 4:
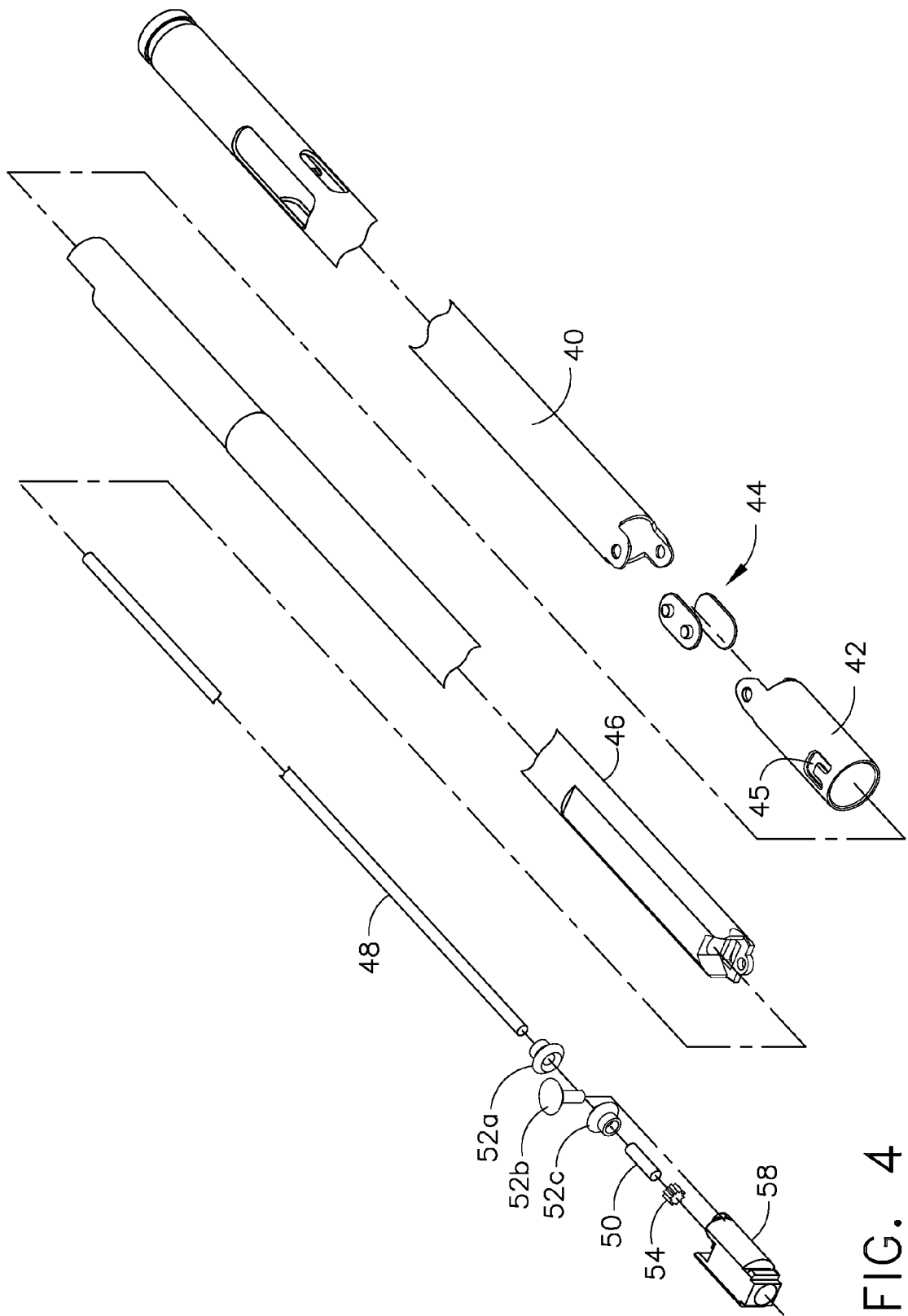
Figure 5:
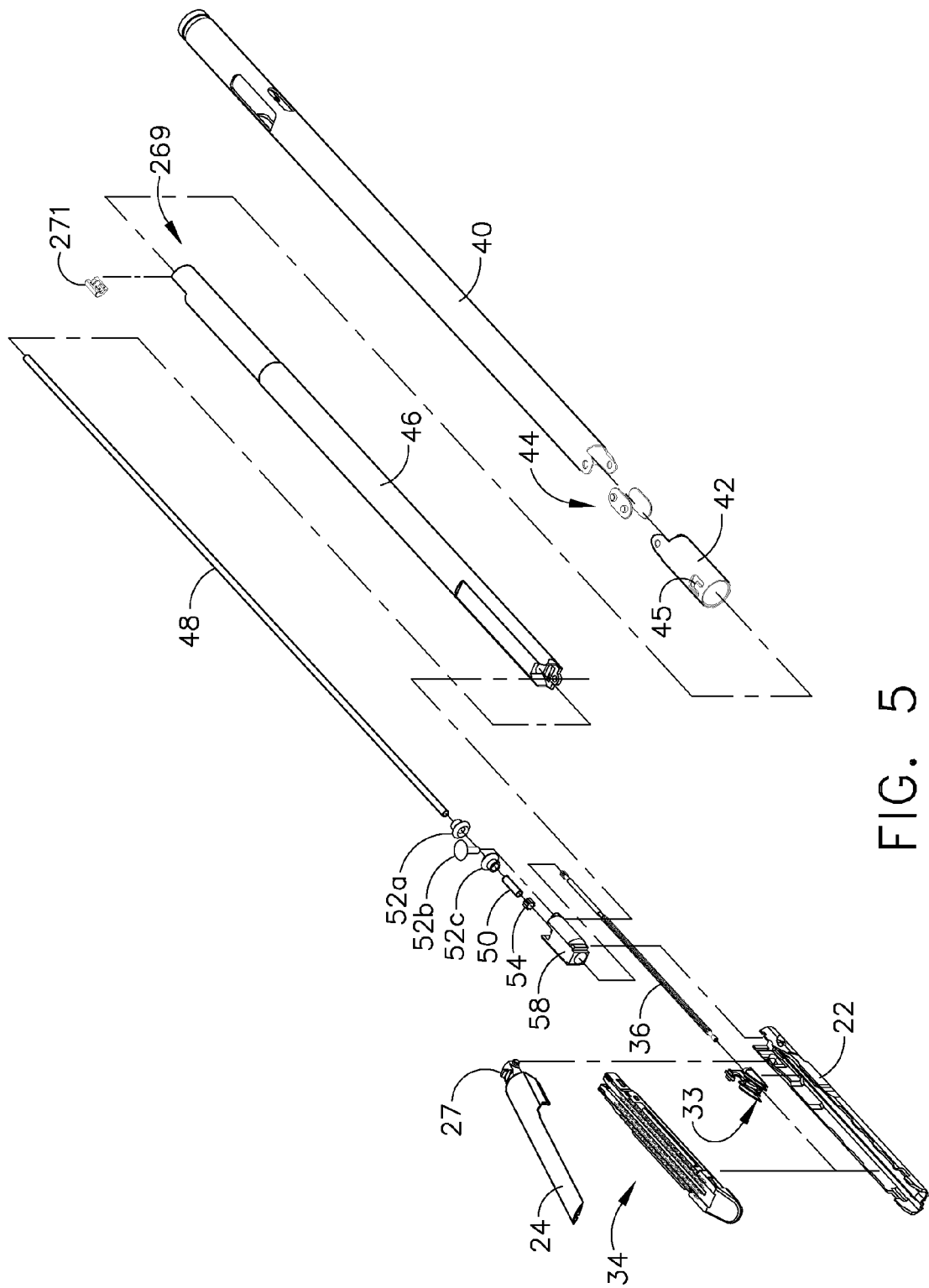
Figure 6:
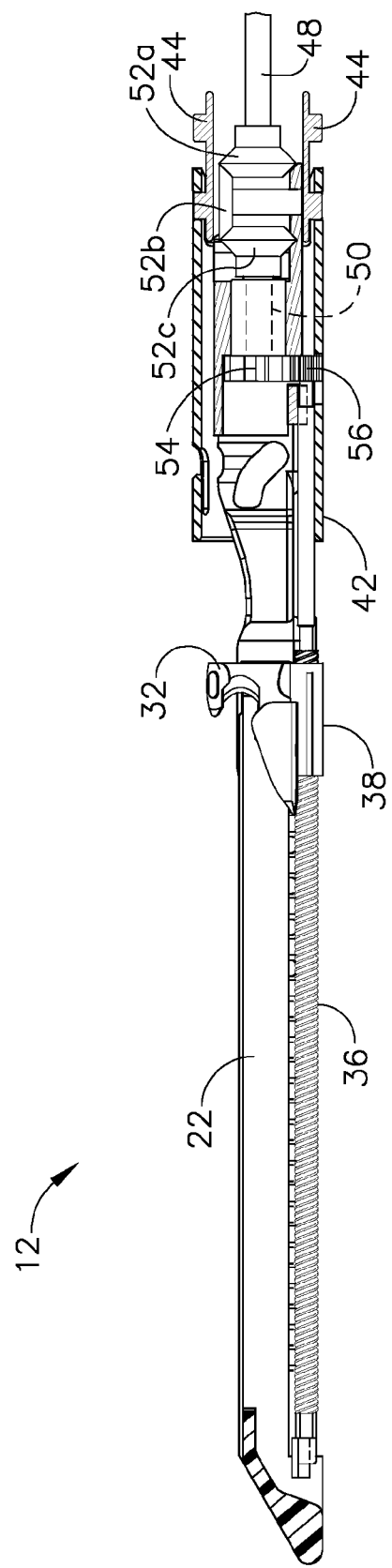
FIG. 6 is a side view of the end effector according to various embodiments of the present invention.

FIGS. 4 and 5 are exploded views and FIG. 6 is a side view of the end effector 12 and shaft 8 according to various embodiments. As shown in the illustrated embodiment, the shaft 8 may include a proximate closure tube 40 and a distal closure tube 42 pivotably linked by a pivot links 44. The distal closure tube 42 includes an opening 45 into which the tab 27 on the anvil 24 is inserted in order to open and close the anvil 24, as further described below. Disposed inside the closure tubes 40, 42 may be a proximate spine tube 46. Disposed inside the proximate spine tube 46 may be a main rotational (or proximate) drive shaft 48 that communicates with a secondary (or distal) drive shaft 50 via a bevel gear assembly 52. The secondary drive shaft 50 is connected to a drive gear 54 that engages a proximate drive gear 56 of the helical screw shaft 36. The vertical bevel gear 52b may sit and pivot in an opening 57 in the distal end of the proximate spine tube 46. A distal spine tube 58 may be used to enclose the secondary drive shaft 50 and the drive gears 54, 56. Collectively, the main drive shaft 48, the secondary drive shaft 50, and the articulation assembly (e.g., the bevel gear assembly 52a-c) are sometimes referred to herein as the "main drive shaft assembly."

A bearing 38, positioned at a distal end of the staple channel 22, receives the helical drive screw 36, allowing the helical drive screw 36 to freely rotate with respect to the channel 22. The helical screw shaft 36 may interface a threaded opening (not shown) of the knife 32 such that rotation of the shaft 36 causes the knife 32 to translate distally or proximately (depending on the direction of the rotation) through the staple channel 22. Accordingly, when the main drive shaft 48 is caused to rotate by actuation of the firing trigger 20 (as explained in more detail below), the bevel gear assembly 52a-c causes the secondary drive shaft 50 to rotate, which in turn, because of the engagement of the drive gears 54, 56, causes the helical screw shaft 36 to rotate, which causes the knife driving member 32 to travel longitudinally along the channel 22 to cut any tissue clamped within the end effector. The sled 33 may be made of, for example, plastic, and may have a sloped distal surface. As the sled 33 traverses the channel 22, the sloped forward surface may push up or drive the staples in the staple cartridge through the clamped tissue and against the anvil 24. The anvil 24 turns the staples, thereby stapling the severed tissue. When the knife 32 is retracted, the knife 32 and sled 33 may become disengaged, thereby leaving the sled 33 at the distal end of the channel 22.

FIGS. 7-10 illustrate an exemplary embodiment of a motor-driven endocutter. The illustrated embodiment provides user-feedback regarding the deployment and loading force of the cutting instrument in the end effector. In addition, the embodiment may use power provided by the user in retracting the firing trigger 20 to power the device (a so-called "power assist" mode). As shown in the illustrated embodiment, the handle 6 includes exterior lower side pieces 59, 60 and exterior upper side pieces 61, 62 that fit together to form, in general, the exterior of the handle 6. A battery 64, such as a Li ion battery, may be provided in the pistol grip portion 26 of the handle 6. The battery 64 powers a motor 65 disposed in an upper portion of the pistol grip portion 26 of the handle 6. According to various embodiments, a number of battery cells connected in series may be used to power the motor 65.

The motor 65 may be a DC brushed driving motor having a maximum rotation of approximately 25,000 RPM with no load. The motor 64 may drive a 90° bevel gear assembly 66 comprising a first bevel gear 68 and a second bevel gear 70. The bevel gear assembly 66 may drive a planetary gear assembly 72. The planetary gear assembly 72 may include a pinion gear 74 connected to a drive shaft 76. The pinion gear 74 may drive a mating ring gear 78 that drives a helical gear drum 80 via a drive shaft 82. A ring 84 may be threaded on the helical gear drum 80. Thus, when the motor 65 rotates, the ring 84 is caused to travel along the helical gear drum 80 by means of the interposed bevel gear assembly 66, planetary gear assembly 72, and ring gear 78.

The handle 6 may also include a run motor sensor 110 in communication with the firing trigger 20 to detect when the firing trigger 20 has been drawn in (or "closed") toward the pistol grip portion 26 of the handle 6 by the operator to thereby actuate the cutting/stapling operation by the end effector 12. The sensor 110 may be a proportional sensor such as, for example, a rheostat, or variable resistor. When the firing trigger 20 is drawn in, the sensor 110 detects the movement, and sends an electrical signal indicative of the voltage (or power) to be supplied to the motor 65. When the sensor 110 is a variable resistor or the like, the rotation of the motor 65 may be generally proportional to the amount of movement of the firing trigger 20. That is, if the operator only draws or closes the firing trigger 20 in a little bit, the rotation of the motor 65 is relatively low. When the firing trigger 20 is fully drawn in (or in the fully closed position), the rotation of the motor 65 is at its maximum. In other words, the harder the user pulls on the firing trigger 20, the more voltage is applied to the motor 65, causing greater rates of rotation.

The handle 6 may include a middle handle piece 104 adjacent to the upper portion of the firing trigger 20. The handle 6 also may comprise a bias spring 112 connected between posts on the middle handle piece 104 and the firing trigger 20. The bias spring 112 may bias the firing trigger 20 to its fully open position. In that way, when the operator releases the firing trigger 20, the bias spring 112 will pull the firing trigger 20 to its open position, thereby removing actuation of the sensor 110, thereby stopping rotation of the motor 65. Moreover, by virtue of the bias spring 112, any time a user closes the firing trigger 20, the user will experience resistance to the closing operation, thereby providing the user with feedback as to the amount of rotation exerted by the motor 65. Further, the operator could stop retracting the firing trigger 20 to thereby remove force from the sensor 100, to thereby stop the motor 65. As such, the user may stop the deployment of the end effector 12, thereby providing a measure of control of the cutting/fastening operation to the operator.

The distal end of the helical gear drum 80 includes a distal drive shaft 120 that drives a ring gear 122, which mates with a pinion gear 124. The pinion gear 124 is connected to the main drive shaft 48 of the main drive shaft assembly. In that way, rotation of the motor 65 causes the main drive shaft assembly to rotate, which causes actuation of the end effector 12, as described above.

The ring 84 threaded on the helical gear drum 80 may include a post 86 that is disposed within a slot 88 of a slotted arm 90. The slotted arm 90 has an opening 92 its opposite end 94 that receives a pivot pin 96 that is connected between the handle exterior side pieces 59, 60. The pivot pin 96 is also disposed through an opening 100 in the firing trigger 20 and an opening 102 in the middle handle piece 104.

In addition, the handle 6 may include a reverse motor (or end-of-stroke sensor) 130 and a stop motor (or beginning-of-stroke) sensor 142. In various embodiments, the reverse motor sensor 130 may be a limit switch located at the distal end of the helical gear drum 80 such that the ring 84 threaded on the helical gear drum 80 contacts and trips the reverse motor sensor 130 when the ring 84 reaches the distal end of the helical gear drum 80. The reverse motor sensor 130, when activated, sends a signal to the motor 65 to reverse its rotation direction, thereby withdrawing the knife 32 of the end effector 12 following the cutting operation. The stop motor sensor 142 may be, for example, a normally-closed limit switch. In various embodiments, it may be located at the proximate end of the helical gear drum 80 so that the ring 84 trips the switch 142 when the ring 84 reaches the proximate end of the helical gear drum 80.

In operation, when an operator of the instrument 10 pulls back the firing trigger 20, the sensor 110 detects the deployment of the firing trigger 20 and sends a signal to the motor 65 to cause forward rotation of the motor 65 at, for example, a rate proportional to how hard the operator pulls back the firing trigger 20. The forward rotation of the motor 65 in turn causes the ring gear 78 at the distal end of the planetary gear assembly 72 to rotate, thereby causing the helical gear drum 80 to rotate, causing the ring 84 threaded on the helical gear drum 80 to travel distally along the helical gear drum 80. The rotation of the helical gear drum 80 also drives the main drive shaft assembly as described above, which in turn causes deployment of the knife 32 in the end effector 12. That is, the knife 32 and sled 33 are caused to traverse the channel 22 longitudinally, thereby cutting tissue clamped in the end effector 12. Also, the stapling operation of the end effector 12 is caused to happen in embodiments where a stapling-type end effector is used.

By the time the cutting/stapling operation of the end effector 12 is complete, the ring 84 on the helical gear drum 80 will have reached the distal end of the helical gear drum 80, thereby causing the reverse motor sensor 130 to be tripped, which sends a signal to the motor 65 to cause the motor 65 to reverse its rotation. This in turn causes the knife 32 to retract, and also causes the ring 84 on the helical gear drum 80 to move back to the proximate end of the helical gear drum 80.

Figure 8:
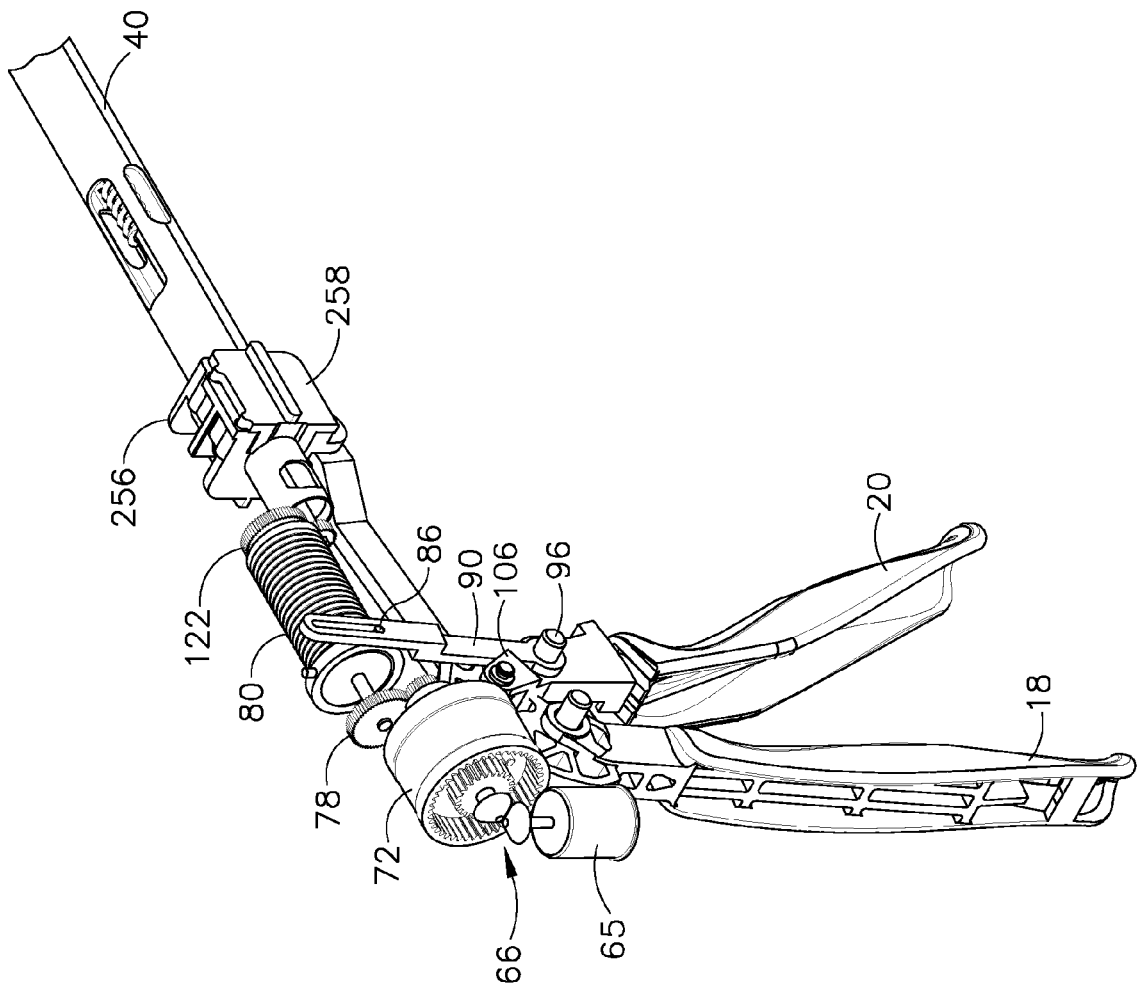
FIGS. 8 and 9 are partial perspective views of the handle according to various embodiments of the present invention.
Figure 9:
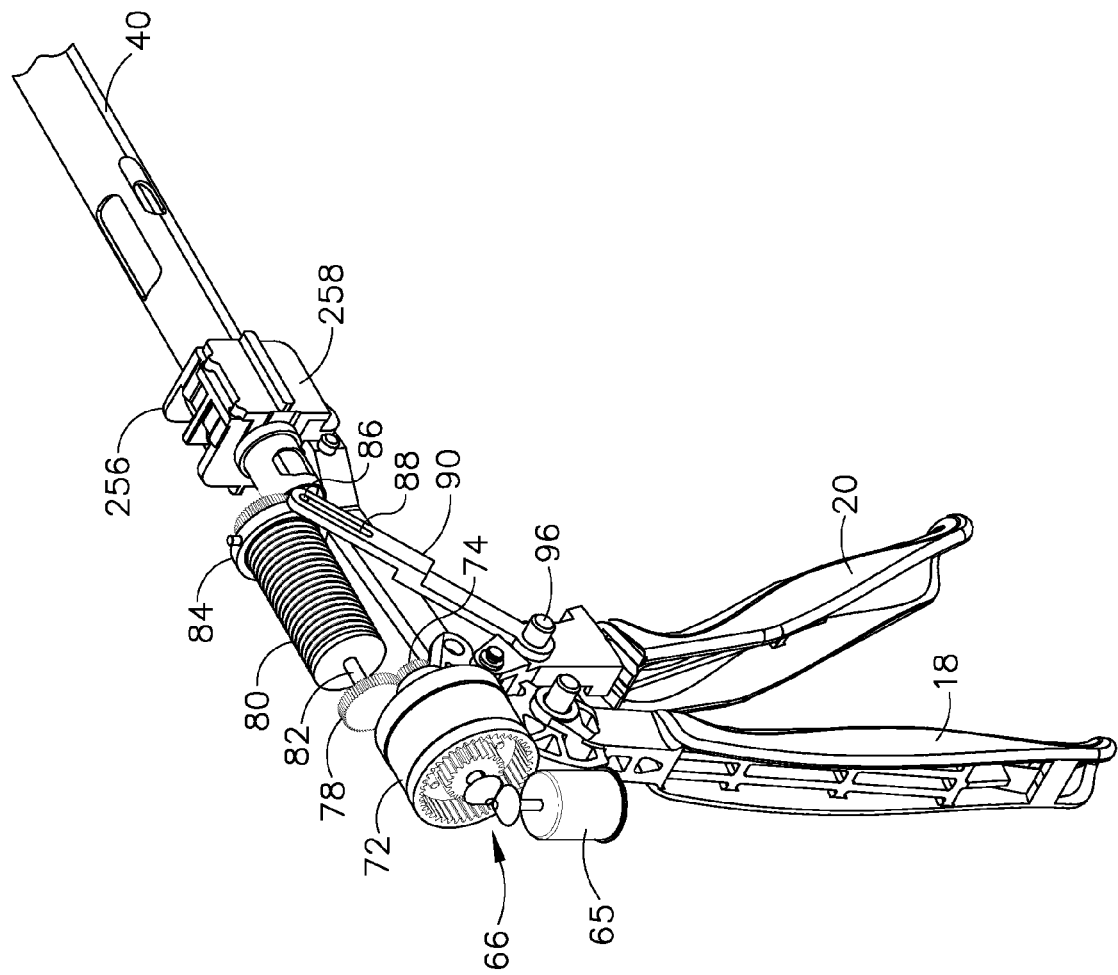
Figure 10:
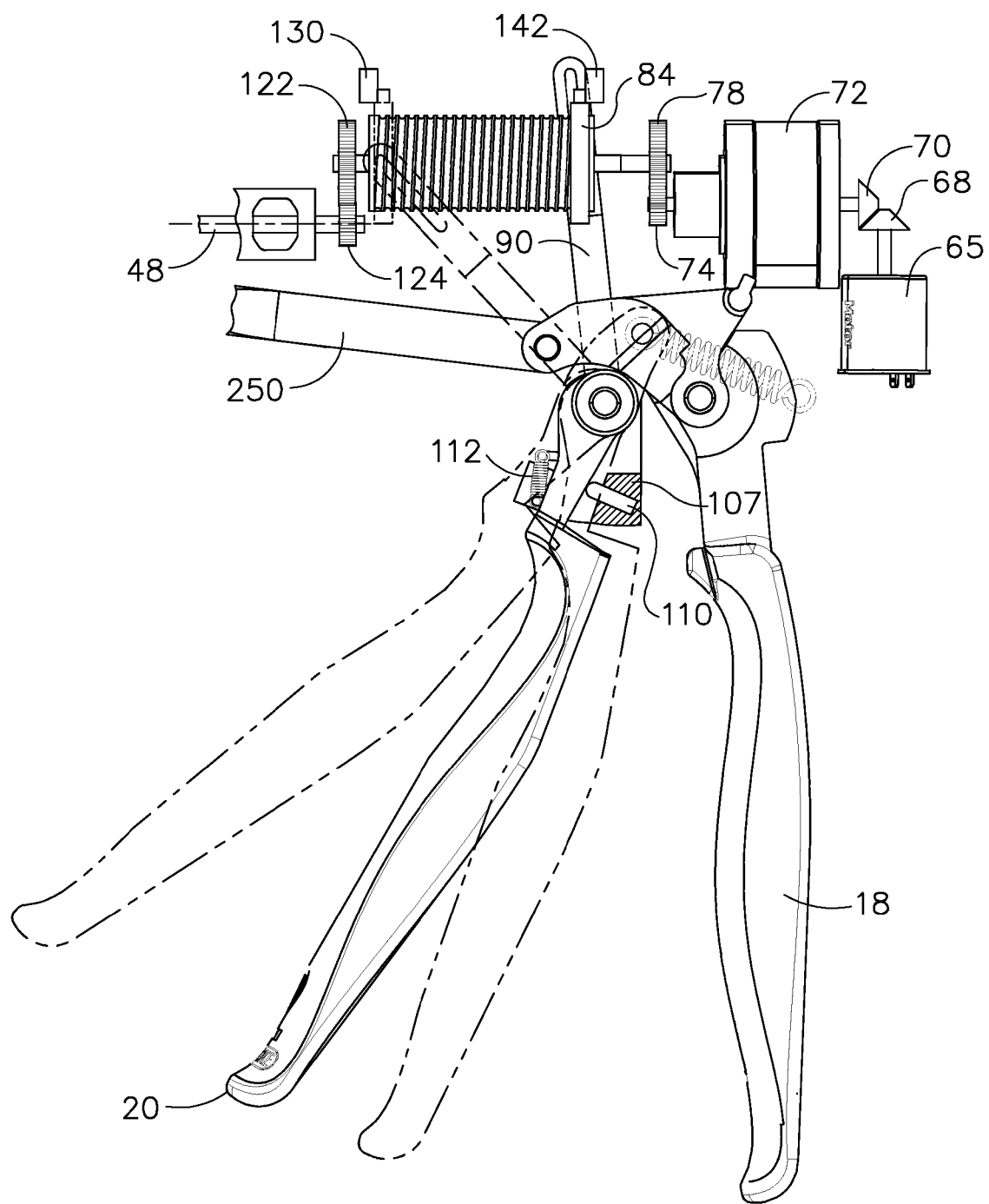
FIG. 10 is a side view of the handle according to various embodiments of the present invention.

The middle handle piece 104 includes a backside shoulder 106 that engages the slotted arm 90 as best shown in FIGS. 8 and 9. The middle handle piece 104 also has a forward motion stop 107 that engages the firing trigger 20. The movement of the slotted arm 90 is controlled, as explained above, by rotation of the motor 65. When the slotted arm 90 rotates CCW as the ring 84 travels from the proximate end of the helical gear drum 80 to the distal end, the middle handle piece 104 will be free to rotate CCW. Thus, as the user draws in the firing trigger 20, the firing trigger 20 will engage the forward motion stop 107 of the middle handle piece 104, causing the middle handle piece 104 to rotate CCW. Due to the backside shoulder 106 engaging the slotted arm 90, however, the middle handle piece 104 will only be able to rotate CCW as far as the slotted arm 90 permits. In that way, if the motor 65 should stop rotating for some reason, the slotted arm 90 will stop rotating, and the user will not be able to further draw in the firing trigger 20 because the middle handle piece 104 will not be free to rotate CCW due to the slotted arm 90.

Components of an exemplary closure system for closing (or clamping) the anvil 24 of the end effector 12 by retracting the closure trigger 18 are also shown in FIGS. 7-10. In the illustrated embodiment, the closure system includes a yoke 250 connected to the closure trigger 18 by a pin 251 that is inserted through aligned openings in both the closure trigger 18 and the yoke 250. A pivot pin 252, about which the closure trigger 18 pivots, is inserted through another opening in the closure trigger 18 which is offset from where the pin 251 is inserted through the closure trigger 18. Thus, retraction of the closure trigger 18 causes the upper part of the closure trigger 18, to which the yoke 250 is attached via the pin 251, to rotate CCW. The distal end of the yoke 250 is connected, via a pin 254, to a first closure bracket 256. The first closure bracket 256 connects to a second closure bracket 258. Collectively, the closure brackets 256, 258 define an opening in which the proximate end of the proximate closure tube 40 (see FIG. 4) is seated and held such that longitudinal movement of the closure brackets 256, 258 causes longitudinal motion by the proximate closure tube 40. The instrument 10 also includes a closure rod 260 disposed inside the proximate closure tube 40. The closure rod 260 may include a window 261 into which a post 263 on one of the handle exterior pieces, such as exterior lower side piece 59 in the illustrated embodiment, is disposed to fixedly connect the closure rod 260 to the handle 6. In that way, the proximate closure tube 40 is capable of moving longitudinally relative to the closure rod 260. The closure rod 260 may also include a distal collar 267 that fits into a cavity 269 in proximate spine tube 46 and is retained therein by a cap 271 (see FIG. 4).

In operation, when the yoke 250 rotates due to retraction of the closure trigger 18, the closure brackets 256, 258 cause the proximate closure tube 40 to move distally (i.e., away from the handle end of the instrument 10), which causes the distal closure tube 42 to move distally, which causes the anvil 24 to rotate about the pivot point 25 into the clamped or closed position. When the closure trigger 18 is unlocked from the locked position, the proximate closure tube 40 is caused to slide proximately, which causes the distal closure tube 42 to slide proximately, which, by virtue of the tab 27 being inserted in the window 45 of the distal closure tube 42, causes the anvil 24 to pivot about the pivot point 25 into the open or unclamped position. In that way, by retracting and locking the closure trigger 18, an operator may clamp tissue between the anvil 24 and channel 22, and may unclamp the tissue following the cutting/stapling operation by unlocking the closure trigger 20 from the locked position.

Figure 11:
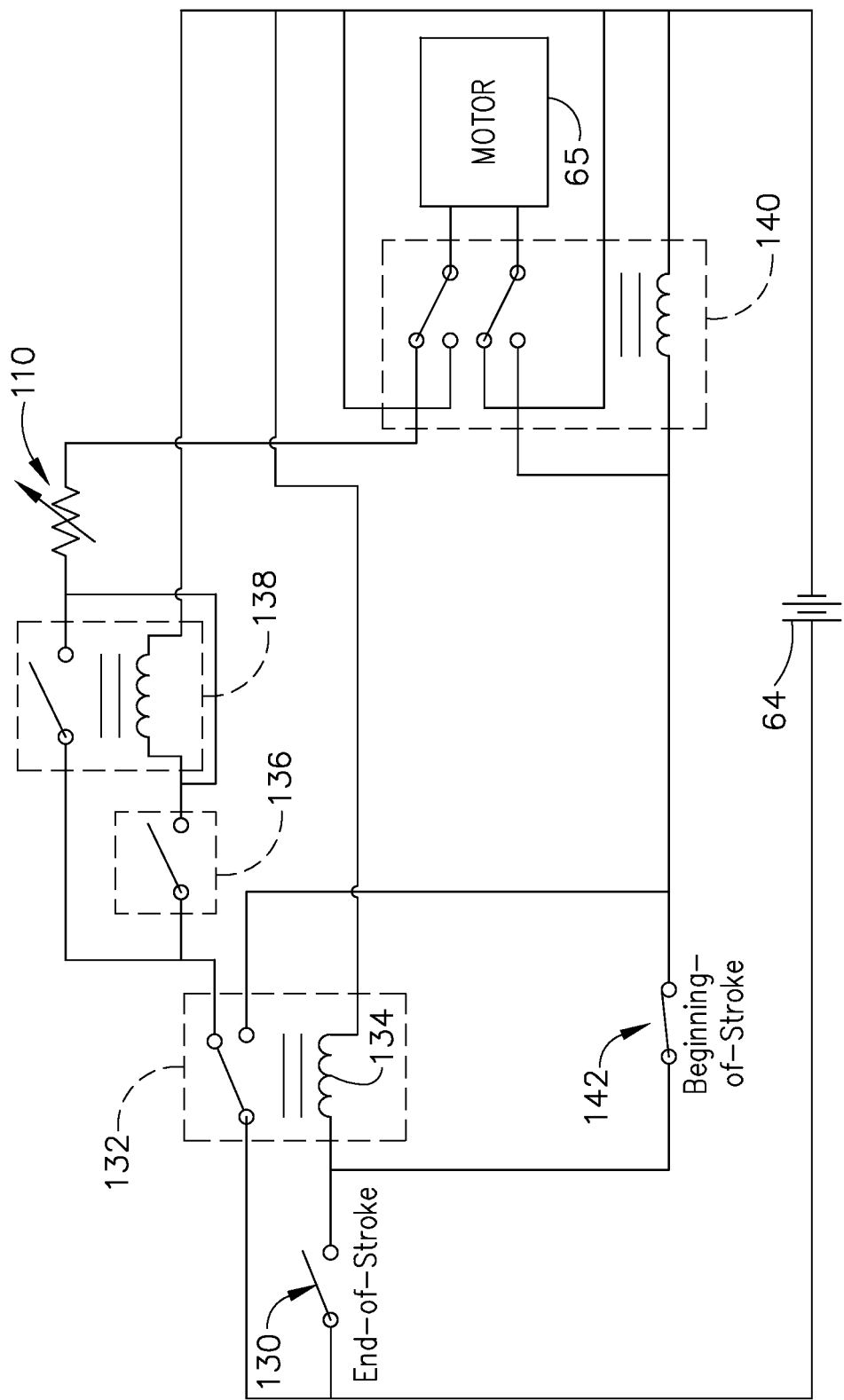
FIG. 11 is a schematic diagram of a circuit used in the instrument according to various embodiments of the present invention.

FIG. 11 is a schematic diagram of an electrical circuit of the instrument 10 according to various embodiments of the present invention. When an operator initially pulls in the firing trigger 20 after locking the closure trigger 18, the sensor 110 is activated, allowing current to flow there through. If the normally-open reverse motor sensor switch 130 is open (meaning the end of the end effector stroke has not been reached), current will flow to a single pole, double throw relay 132. Since the reverse motor sensor switch 130 is not closed, the inductor 134 of the relay 132 will not be energized, so the relay 132 will be in its non-energized state. The circuit also includes a cartridge lockout sensor 136. If the end effector 12 includes a staple cartridge 34, the sensor 136 will be in the closed state, allowing current to flow. Otherwise, if the end effector 12 does not include a staple cartridge 34, the sensor 136 will be open, thereby preventing the battery 64 from powering the motor 65.

When the staple cartridge 34 is present, the sensor 136 is closed, which energizes a single pole, single throw relay 138. When the relay 138 is energized, current flows through the relay 136, through the variable resistor sensor 110, and to the motor 65 via a double pole, double throw relay 140, thereby powering the motor 65, and allowing it to rotate in the forward direction. When the end effector 12 reaches the end of its stroke, the reverse motor sensor 130 will be activated, thereby closing the switch 130 and energizing the relay 134. This causes the relay 134 to assume its energized state (not shown in FIG. 13), which causes current to bypass the cartridge lockout sensor 136 and variable resistor 110, and instead causes current to flow to both the normally-closed double pole, double throw relay 142 and back to the motor 65, but in a manner, via the relay 140, that causes the motor 65 to reverse its rotational direction. Because the stop motor sensor switch 142 is normally closed, current will flow back to the relay 134 to keep it closed until the switch 142 opens. When the knife 32 is fully retracted, the stop motor sensor switch 142 is activated, causing the switch 142 to open, thereby removing power from the motor 65.

In other embodiments, rather than a proportional-type sensor 110, an on-off type sensor could be used. In such embodiments, the rate of rotation of the motor 65 would not be proportional to the force applied by the operator. Rather, the motor 65 would generally rotate at a constant rate. But the operator would still experience force feedback because the firing trigger 20 is geared into the gear drive train.

Additional configurations for motorized surgical instruments are disclosed in published U.S. application Pub. No. 2007/0175962 A1, entitled "Motor-driven surgical cutting and fastening instrument with tactile position feedback," which is incorporated herein by reference.

Figure 12:
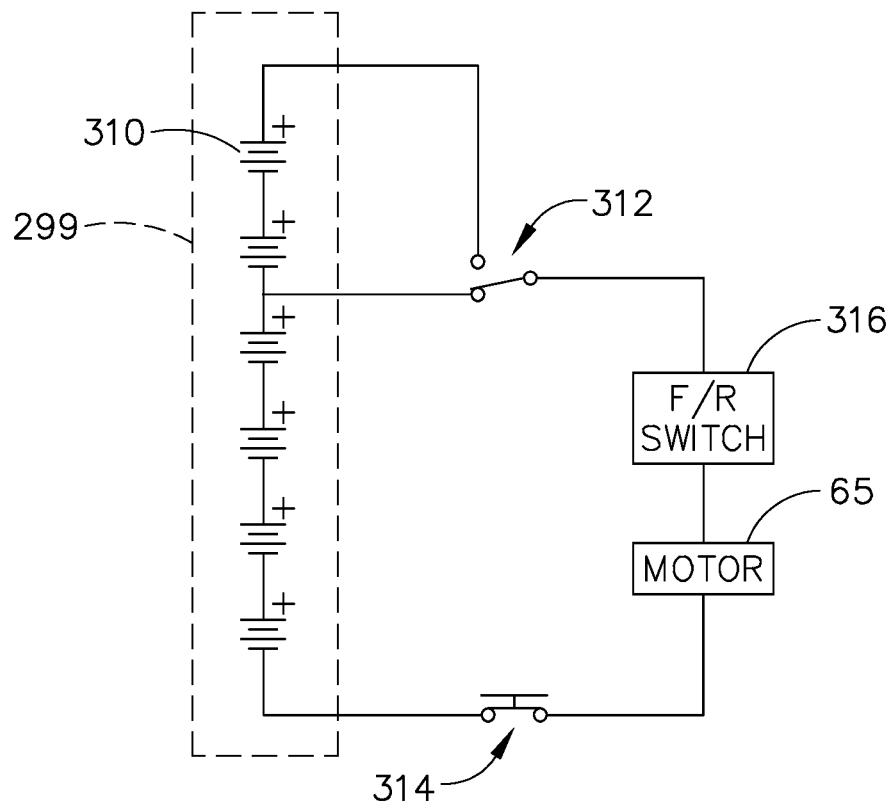
FIGS. 12-14 and 17 are schematic diagrams of circuits used to power the motor of the instrument according to various embodiments of the present invention.

In a motorized surgical instrument, such as one of the motorized endoscopic instruments described above or in a motorized circular cutter instrument, the motor may be powered by a number of battery cells connected in series. Further, it may be desirable in certain circumstances to power the motor with some fraction of the total number of battery cells. For example, as shown in FIG. 12, the motor 65 may be powered by a power pack 299 comprising six (6) battery cells 310 connected in series. The battery cells 310 may be, for example, 3-volt lithium battery cells, such as CR 123A battery cells, although in other embodiments, different types of battery cells could be used (including battery cells with different voltage levels and/or different chemistries). If six 3-volt battery cells 310 were connected in series to power the motor 65, the total voltage available to power the motor 65 would be 18 volts. The battery cells 310 may comprise rechargeable or non-rechargeable battery cells.

In such an embodiment, under the heaviest loads, the input voltage to the motor 65 may sag to about nine to ten volts. At this operating condition, the power pack 299 is delivering maximum power to the motor 65. Accordingly, as shown in FIG. 12, the circuit may include a switch 312 that selectively allows the motor 65 to be powered by either (1) all of the battery cells 310 or (2) a fraction of the battery cells 310. As shown in FIG. 12, by proper selection, the switch 312 may allow the motor 65 to be powered by all six battery cells or four of the battery cells. That way, the switch 312 could be used to power the motor 65 with either 18 volts (when using all six battery cells 310) or 12 volts (such using four of the second battery cells). In various embodiments, the design choice for the number of battery cells in the fraction that is used to power the motor 65 may be based on the voltage required by the motor 65 when operating at maximum output for the heaviest loads.

The switch 312 may be, for example, an electromechanical switch, such as a micro switch. In other embodiments, the switch 312 may be implemented with a solid-state switch, such as transistor. A second switch 314, such as a push button switch, may be used to control whether power is applied to the motor 65 at all. Also, a forward/reverse switch 316 may be used to control whether the motor 65 rotates in the forward direction or the reverse direction. The forward/reverse switch 316 may be implemented with a double pole—double throw switch, such as the relay 140 shown in FIG. 11.

In operation, the user of the instrument 10 could select the desired power level by using some sort of switch control, such as a position-dependent switch (not shown), such as a toggle switch, a mechanical lever switch, or a cam, which controls the position of the switch 312. Then the user may activate the second switch 314 to connect the selected battery cells 310 to the motor 65. In addition, the circuit shown in FIG. 12 could be used to power the motor of other types of motorized surgical instruments, such as circular cutters and/or laparoscopic instruments. More details regarding circular cutters may be found in published U.S. patent applications Pub. No. 2006/0047307 A1 and Pub. No. 2007/0262116 A1, which are incorporated herein by reference.

Figure 13:
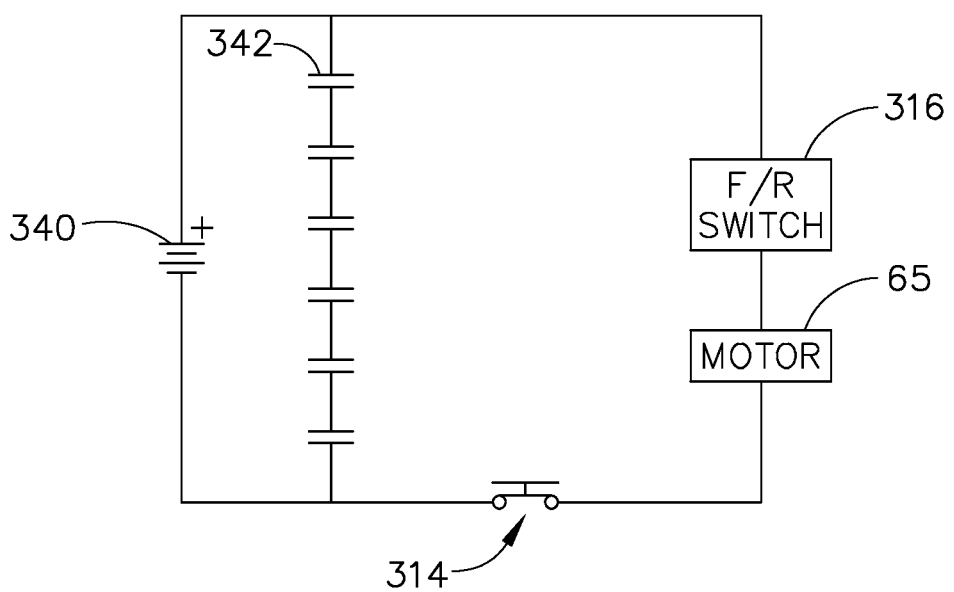

In other embodiments, as shown in FIG. 13, a primary power source 340, such as a battery cell, such as a CR2 or CR123A battery cell, may be used to charge a number of secondary accumulator devices 342. The primary power source 340 may comprise one or a number of series-connected battery cells, which are preferably replaceable in the illustrated embodiment. The secondary accumulator devices 342 may comprise, for example, rechargeable battery cells and/or supercapacitors (also known as "ultracapacitors" or "electrochemical double layer capacitors" (EDLC)). Supercapacitors are electrochemical capacitors that have an unusually high energy density when compared to common electrolytic capacitors, typically on the order of thousands of times greater than a high-capacity electrolytic capacitor.

The primary power source 340 may charge the secondary accumulator devices 342. Once sufficiently charged, the primary power source 340 may be removed and the secondary accumulator devices 342 may be used to power the motor 65 during a procedure or operation. The accumulating devices 342 may take about fifteen to thirty minutes to charge in various circumstances. Supercapacitors have the characteristic they can charge and discharge extremely rapidly in comparison to conventional batteries. In addition, whereas batteries are good for only a limited number of charge/discharge cycles, supercapacitors can often be charged/discharged repeatedly, sometimes for tens of millions of cycles. For embodiments using supercapacitors as the secondary accumulator devices 342, the supercapacitors may comprise carbon nanotubes, conductive polymers (e.g., polyacenes), or carbon aerogels.

Figure 14:
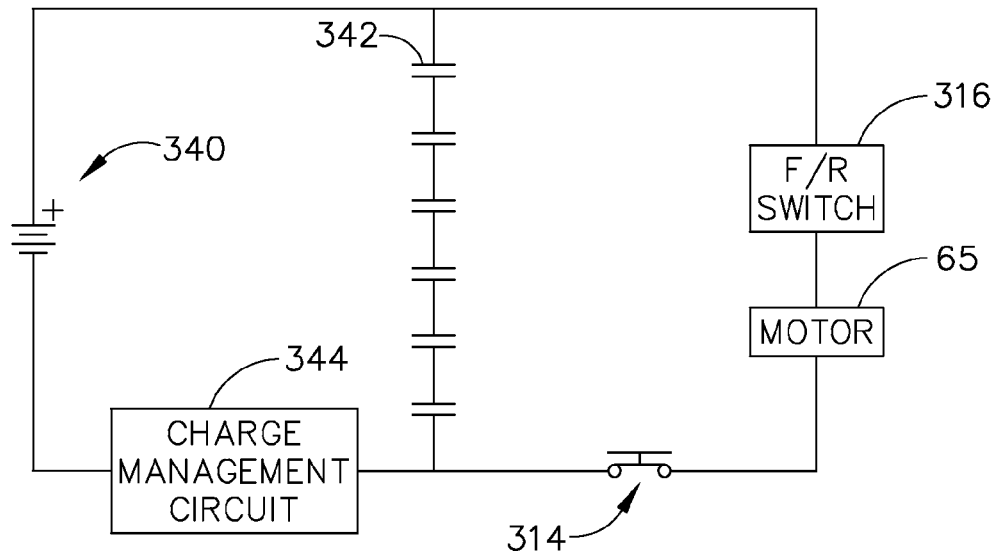

As shown in FIG. 14, a charge management circuit 344 could be employed to determine when the secondary accumulator devices 342 are sufficiently charged. The charge management circuit 344 may include an indicator, such as one or more LEDs, an LCD display, etc., that is activated to alert a user of the instrument 10 when the secondary accumulator devices 342 are sufficiently charged.

The primary power source 340, the secondary accumulator devices 342, and the charge management circuit 344 may be part of a power pack in the pistol grip portion 26 of the handle 6 of the instrument 10, or in another part of the instrument 10. The power pack may be removable from the pistol grip portion 26, in which case, when the instrument 10 is to be used for surgery, the power pack may be inserted aseptically into the pistol grip portion 26 (or other position in the instrument according to other embodiments) by, for example, a circulating nurse assisting in the surgery. After insertion of the power pack, the nurse could put the replaceable primary power source 340 in the power pack to charge up the secondary accumulator devices 342 a certain time period prior to use of the instrument 10, such as thirty minutes. When the secondary accumulator devices 342 are charged, the charge management circuit 344 may indicate that the power pack is ready for use. At this point, the replaceable primary power source 340 may be removed. During the operation, the user of the instrument 10 may then activate the motor 65, such as by activating the switch 314, whereby the secondary accumulator devices 342 power the motor 65. Thus, instead of having a number of disposable batteries to power the motor 65, one disposable battery (as the primary power source 340) could be used in such an embodiment, and the secondary accumulator devices 342 could be reusable. In alternative embodiments, however, it should be noted that the secondary accumulator devices 342 could be non-rechargeable and/or non-reusable. The secondary accumulators 342 may be used with the cell selection switch 312 described above in connection with FIG. 12.

The charge management circuit 344 may also include indicators (e.g., LEDs or LCD display) that indicate how much charge remains in the secondary accumulator devices 342. That way, the surgeon (or other user of the instrument 10) can see how much charge remains through the course of the procedure involving the instrument 10.

Figure 15:
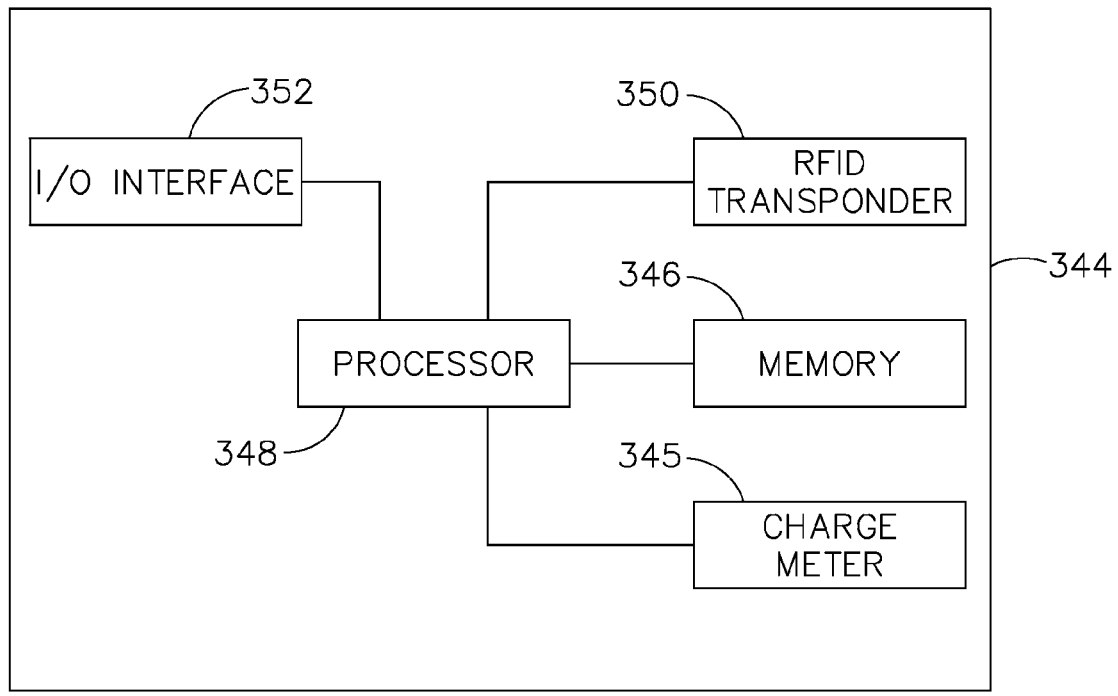
FIG. 15 is a block diagram illustrating a charge management circuit according to various embodiments of the present invention.

The charge management circuit 344, as shown in FIG. 15, may comprise a charge meter 345 for measuring the charge across the secondary accumulators 342. The charge management circuit 344 also may comprise a non-volatile memory 346, such as flash or ROM memory, and one or more processors 348. The processor(s) 348 may be connected to the memory 346 to control the memory. In addition, the processor(s) 348 may be connected to the charge meter 345 to read the readings of and otherwise control the charge meter 345. Additionally, the processor(s) 348 may control the LEDs or other output devices of the charge management circuit 344. The processor(s) 348 can store parameters of the instrument 10 in the memory 346. The parameters may include operating parameters of the instrument that are sensed by various sensors that may be installed or employed in the instrument 10, such as, for example, the number of firings, the levels of forces involved, the distance of the compression gap between the opposing jaws of the end effector 12, the amount of articulation, etc. Additionally, the parameters stored in the memory 346 may comprise ID values for various components of the instrument 10 that the charge management circuit 344 may read and store. The components having such IDs may be replaceable components, such as the staple cartridge 34. The IDs may be for example, RFIDs that the charge management circuit 344 reads via a RFID transponder 350. The RFID transponder 350 may read RFIDs from components of the instrument, such as the staple cartridge 34, that include RFID tags. The ID values may be read, stored in the memory 346, and compared by the processor 348 to a list of acceptable ID values stored in the memory 346 or another store associated with the charge management circuit, to determine, for example, if the removable/replaceable component associated with the read ID value is authentic and/or proper. According to various embodiments, if the processor 348 determines that the removable/replaceable component associated with the read ID value is not authentic, the charge management circuit 344 may prevent use of the power pack by the instrument 10, such as by opening a switch (not shown) that would prevent power from the power pack being delivered to the motor 65. According to various embodiments, various parameters that the processor 348 may evaluate to determine whether the component is authentic and/or proper include: date code; component model/type; manufacturer; regional information; and previous error codes.

The charge management circuit 344 may also comprise an i/o interface 352 for communicating with another device, such as described below. That way, the parameters stored in the memory 346 may be downloaded to another device. The i/o interface 352 may be, for example, a wired or wireless interface.

Figure 16:
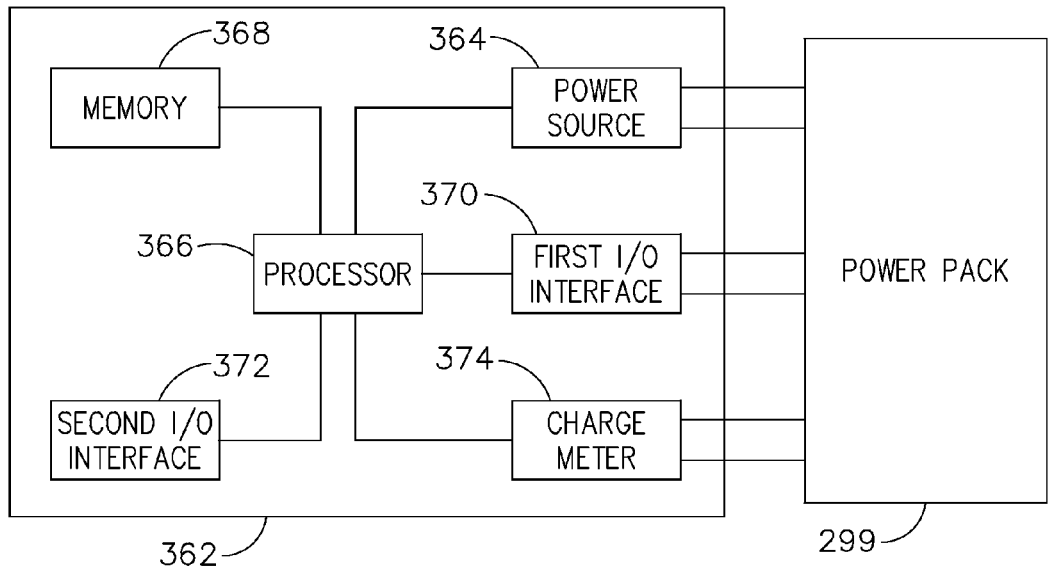
FIG. 16 is a block diagram illustrating a charger base according to various embodiments of the present invention.

As mentioned before, the power pack may comprise the secondary accumulators 342, the charge management circuit 344, and/or the f/r switch 316. According to various embodiments, as shown in FIG. 16, the power pack 299 could be connected to a charger base 362, which may, among other things, charge the secondary accumulators 342 in the power pack. The charger base 362 could be connected to the power pack 299 by connecting aseptically the charger base 362 to the power pack 299 while the power pack is installed in the instrument 10. In other embodiments where the power pack is removable, the charger base 362 could be connected to the power pack 299 by removing the power pack 299 from the instrument 10 and connecting it to the charger base 362. For such embodiments, after the charger base 362 sufficiently charges the secondary accumulators 342, the power pack 299 may be aseptically installed in the instrument 10.

As shown in FIG. 16, the charger base 362 may comprise a power source 364 for charging the secondary accumulators 342. The power source 364 of the charger base 362 may be, for example, a battery (or a number of series-connected batteries), or an AC/DC converter that converters AC power, such as from electrical power mains, to DC, or any other suitable power source for charging the secondary accumulators 342. The charger base 362 may also comprise indicator devices, such as LEDs, a LCD display, etc., to show the charge status of the secondary accumulators 342.

In addition, as shown in FIG. 16, the charger base 362 may comprise one or more processors 366, one or more memory units 368, and i/o interfaces 370, 372. Through the first i/o interface 370, the charger base 362 may communicate with the power pack 299 (via the power pack's i/o interface 352). That way, for example, data stored in the memory 346 of the power pack 299 may be downloaded to the memory 368 of the charger base 362. In that way, the processor 366 can evaluate the ID values for the removable/replaceable components, downloaded from the charge management circuit 344, to determine the authenticity and suitability of the components. The operating parameters downloaded from the charge management circuit 344 may also stored in the memory 368, and then may then be downloaded to another computer device via the second i/o interface 372 for evaluation and analysis, such as by the hospital system in which the operation involving the instrument 10 is performed, by the office of the surgeon, by the distributor of the instrument, by the manufacturer of the instrument, etc.

The charger base 362 may also comprise a charge meter 374 for measuring the charge across the secondary accumulators 342. The charge meter 374 may be in communication with the processor(s) 366, so that the processor(s) 366 can determine in real-time the suitability of the power pack 299 for use to ensure high performance.

Figure 17:
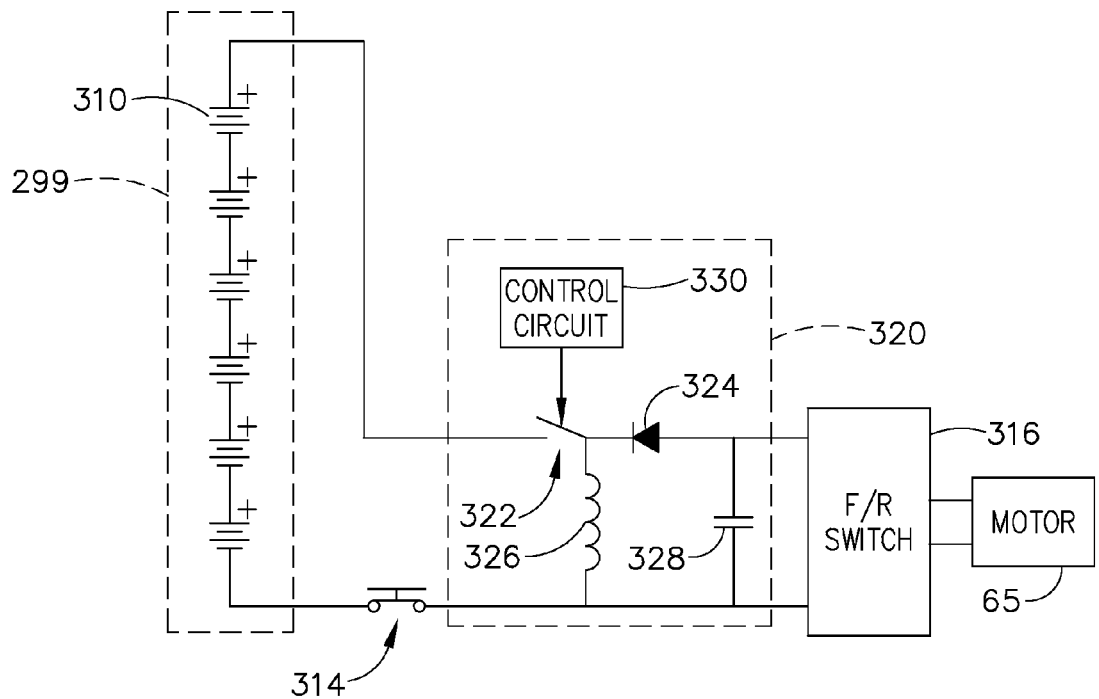

In another embodiment, as shown in FIG. 17, the battery circuit may comprise a power regulator 320 to control the power supplied by the power savers 310 to the motor 65. The power regulator 320 may also be part of the power pack 299, or it may be a separate component. As mentioned above, the motor 65 may be a brushed DC motor. The speed of brushed DC motors generally is proportional to the applied input voltage. The power regulator 320 may provide a highly regulated output voltage to the motor 65 so that the motor 65 will operate at a constant (or substantially constant) speed. According to various embodiments, the power regulator 320 may comprise a switch-mode power converter, such as a buck-boost converter, as shown in the example of FIG. 17. Such a buck-boost converter 320 may comprise a power switch 322, such as a FET, a rectifier 32, an inductor 326, and a capacitor 328. When the power switch 322 is on, the input voltage source (e.g., the power sources 310) is directly connected to the inductor 326, which stores energy in this state. In this state, the capacitor 328 supplies energy to the output load (e.g., the motor 65). When the power switch 320 is in the off state, the inductor 326 is connected to the output load (e.g., the motor 65) and the capacitor 328, so energy is transferred from the inductor 326 to the capacitor 328 and the load 65. A control circuit 330 may control the power switch 322. The control circuit 330 may employ digital and/or analog control loops. In addition, in other embodiments, the control circuit 330 may receive control information from a master controller (not shown) via a communication link, such as a serial or parallel digital data bus. The voltage set point for the output of the power regulator 320 may be set, for example, to one-half of the open circuit voltage, at which point the maximum power available from the source is available.

In other embodiments, different power converter topologies may be employed, including linear or switch-mode power converters. Other switch-mode topologies that may be employed include a flyback, forward, buck, boost, and SEPIC. The set point voltage for the power regulator 320 could be changed depending on how many of the battery cells are being used to power the motor 65. Additionally, the power regulator 320 could be used with the secondary accumulator devices 342 shown in FIG. 13. Further, the forward-reverse switch 316 could be incorporated into the power regulator 320, although it is shown separately in FIG. 17.

Figure 18:
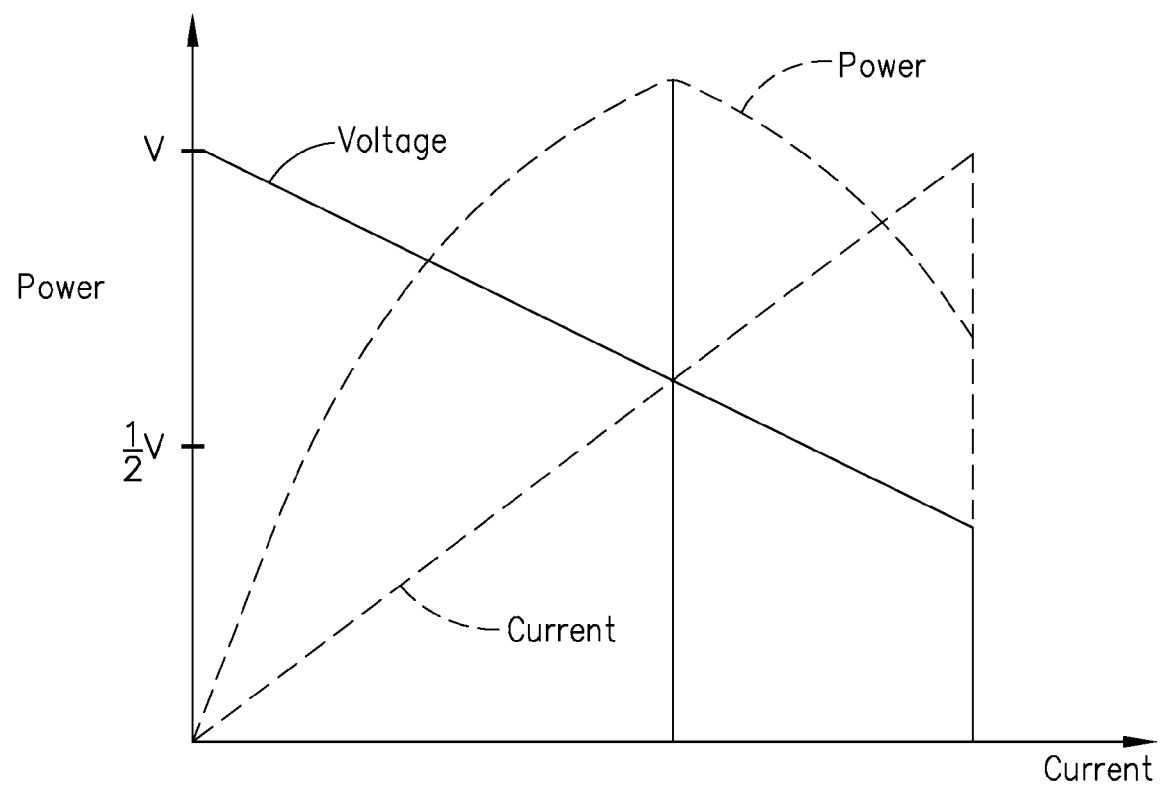
FIG. 18 illustrates a typical power curve of a battery.

Batteries can typically be modeled as an ideal voltage source and a source resistance. For an ideal model, when the source and load resistance are matched, maximum power is transferred to the load. FIG. 18 shows a typical power curve for a battery. When the battery circuit is open, the voltage across the battery is high (at its open circuit value) and the current drawn from the battery is zero. The power delivered from the battery is zero also. As more current is drawn from the battery, the voltage across the battery decreases. The power delivered by the battery is the product of the current and the voltage. The power reaches its peak around at a voltage level that is less than the open circuit voltage. As shown in FIG. 18, with most battery chemistries there is a sharp drop in the voltage/power at higher current because of the chemistry or positive temperature coefficient (PTC), or because of a battery protection device.

Particularly for embodiments using a battery (or batteries) to power the motor 65 during a procedure, the control circuit 330 can monitor the output voltage and control the set point of the regulator 320 so that the battery operates on the "left" or power-increasing side of the power curve. If the battery reaches the peak power level, the control circuit 330 can change (e.g., lower) the set point of the regulator so that less total power is being demanded from the battery. The motor 65 would then slow down. In this way, the demand from the power pack would rarely if ever exceed the peak available power so that a power-starving situation during a procedure could be avoided.

In addition, according to other embodiments, the power drawn from the battery may be optimized in such a way that the chemical reactions within the battery cells would have time to recover, to thereby optimize the current and power available from the battery. In pulsed loads, batteries typically provide more power at the beginning of the pulse that toward the end of the pulse. This is due to several factors, including: (1) the PTC may be changing its resistance during the pulse; (2) the temperature of the battery may be changing; and (3) the electrochemical reaction rate is changing due to electrolyte at the cathode being depleted and the rate of diffusion of the fresh electrolyte limits the reaction rate. According to various embodiments, the control circuit 330 may control the converter 320 so that it draws a lower current from the battery to allow the battery to recover before it is pulsed again.

According to other embodiments, the instrument 10 may comprise a clutch-type torque-limiting device. The clutch-type torque-limiting device may be located, for example, between the motor 65 and the bevel gear 68, between the bevel gear 70 and the planetary gear assembly 72, or on the output shaft of the planetary gear assembly 72. According to various embodiments, the torque-limiting device may use an electromagnetic or permanent magnetic clutch.

Figure 20:
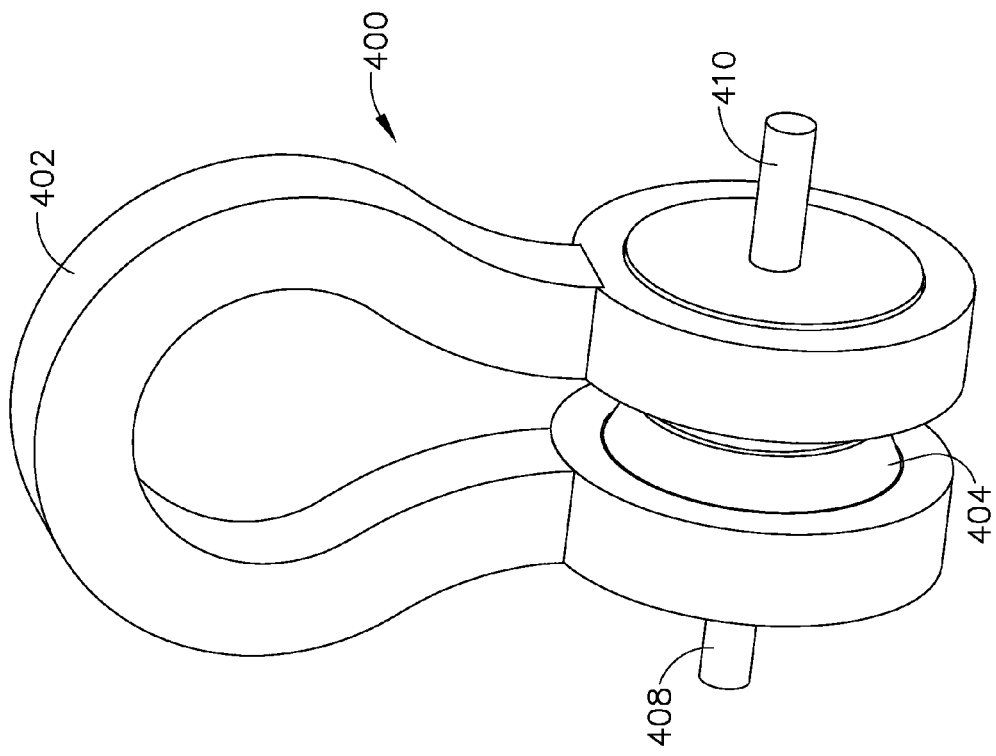
FIGS. 19-22 illustrate embodiments of an electromagnetic, clutch-type torque-limiting device according to various embodiments of the present invention.
Figure 19:
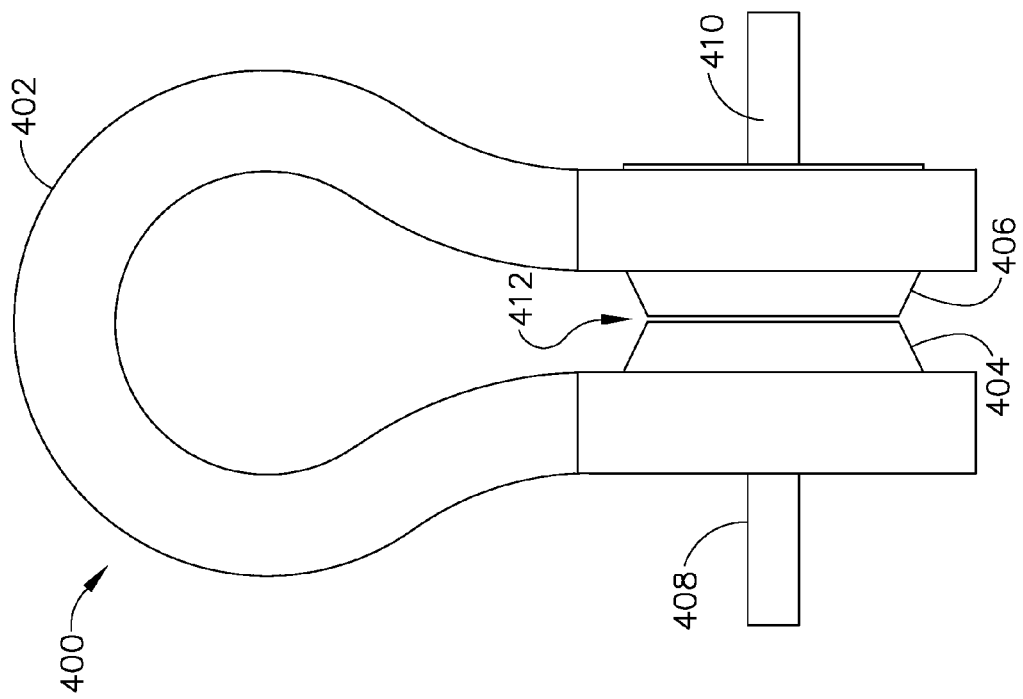
Figure 22:
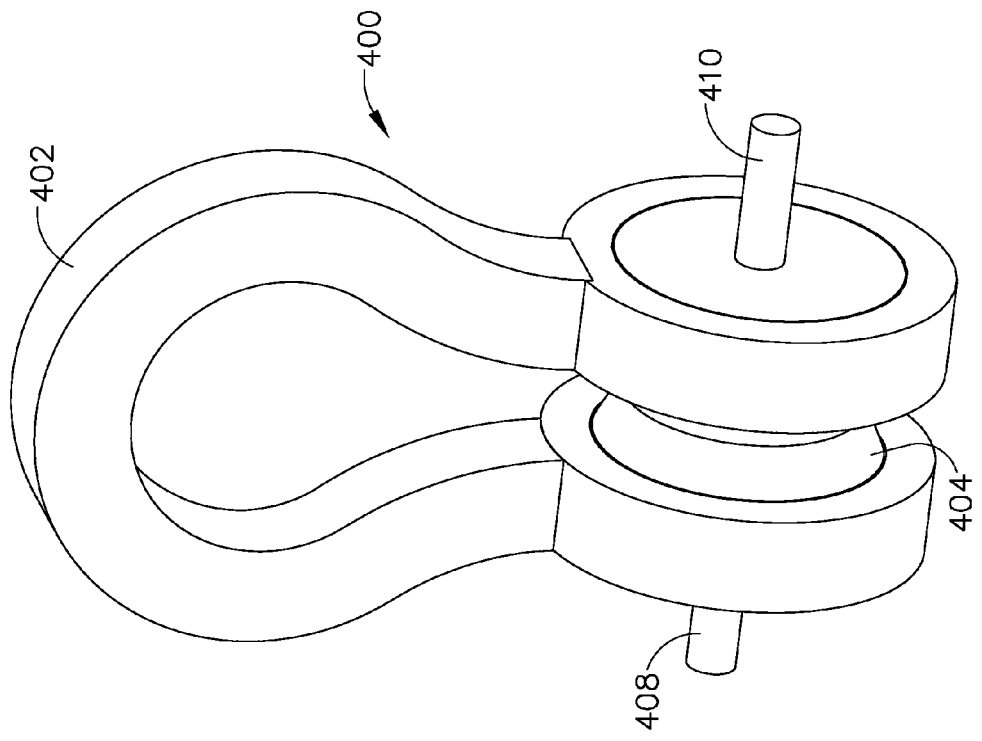
Figure 21:
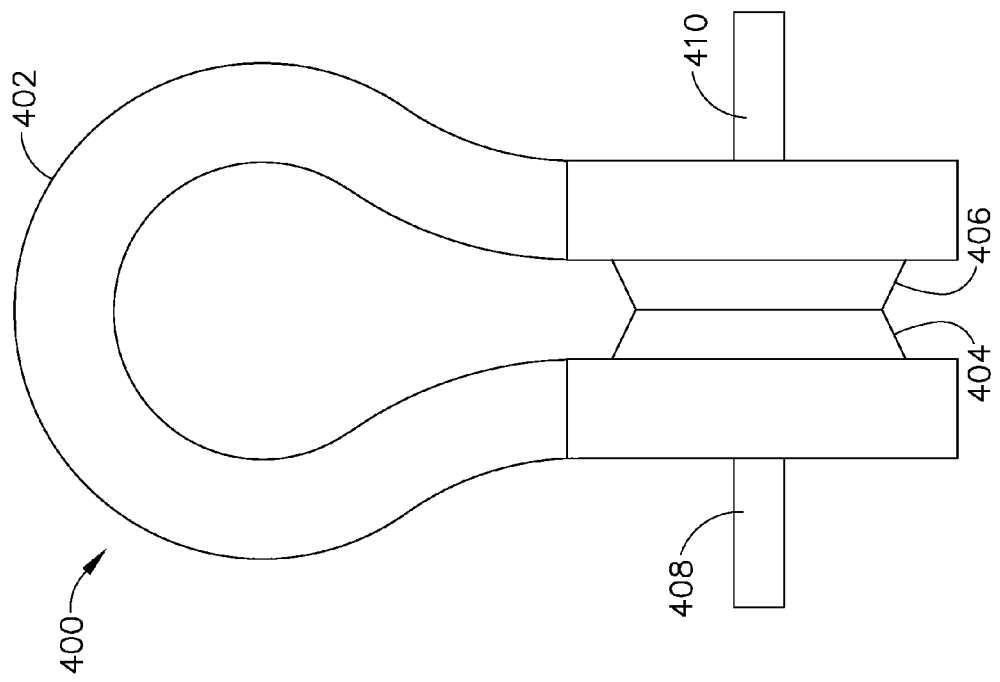

FIGS. 19 to 22 show a sample electromagnetic clutch 400 that could be used in the instrument 10 according to various embodiments. The clutch 400 may comprise a horseshoe-shaped stator 402 having magnetic disks 404, 406 at each end. The first disk 404 may be connected to an axially movable, rotatable pole piece 408, such as the output pole of the motor 65. The second magnetic disk 406 may be connected to an axially stationary, rotatable pole piece 410, such as an input pole to a gear box of the instrument 10. In the views of FIGS. 19 and 20, the first pole piece 408 is axially pulled away from the second pole piece 410 by a clearance 412 such that the magnetic disks 404, 406 are not engaged. A wire coil (not shown), which may be wrapped around the stator 402 may be used to create the electromagnetic flux needed to actuate the clutch 400. When the coil conducts an electrical current, the resulting magnetic flux may cause the two magnetic disks 404, 406 to attract, causing the first pole piece 408 to move axially toward the second pole piece 410, thereby causing the two magnetic disks 404, 406 to become engaged, as shown in FIGS. 21 and 22, such that the two pole pieces 408, 410 will rotate together until the torque exceeds the friction torque generated between the faces of magnetic disks 404 and 406.

The attractive force between the two disks 404, 406 and the corresponding torque capacity of the clutch 400 could be controlled by controlling the diameter of the disks 404, 406, the coefficient of friction between the contacting faces of magnetic disks 404 and 406, and by using magnetic materials for the disks 404, 406 that saturate at a known and controllable flux density. Therefore, even if there was an operating condition where more current was passed through the coil, the magnetic material of the disks 404, 406 would not generate a greater attractive force and subsequent limiting torque.

Utilization of such a clutch has many additional potential benefits. Being electrically controlled, the clutch 400 could be quickly deactivated by removing current from the wire to limit the amount of heat generated within the clutch 400 and within the motor 65. By disconnecting the motor from the rest of the drive train, via the clutch 400, most of the stored inertial energy in the drive train would be disconnected, limiting shock if the output were to be blocked suddenly. In addition, by being electrically controlled, some limited slipping could be designed-in to aid in reducing shocks when restarting the drive train under load. Further, because the magnetic saturation properties of one or more of the components (e.g., the magnetic disks 404, 406) within the clutch could be used to control the torque limit instead of coil current, the clutch 400 would be less sensitive to changes in system voltage. The torque limit in such embodiments would be primarily a function of the physical dimensions of the components of the clutch (e.g., the magnetic disks 404, 406) and would not require voltage regulators or other external components for proper operation.

In another embodiment, rather than using an electromagnetic clutch, the torque-limiting device may comprise a permanent magnet (not shown). The permanent magnet may be connected, for example, to the first, axially-movable, pole piece 408, and attract the axially-fixed second pole piece 410, or vice versa. In such embodiments, one of the disks 404, 406 could be made of a permanent magnet and the other one of a magnetic material like iron. In a slight variation, the stator 402 could be made in the form of a permanent magnet, causing the magnetic disks 404 and 406 to be attracted to each other. Because of the permanent magnet, the two disks 404, 406 would be engaged always. Using a permanent magnet would not provide as accurate as torque control as the electromagnetic clutch configuration described above, but it would have the advantages of: (1) not requiring controls or control logic to control the current through the coil; (2) being more compact that the electromagnetic clutch configuration; and (3) simplifying design of the instrument 10.

As mentioned previously, the end effector 12 may emit RF energy to coagulate tissue clamped in the end effector. The RF energy may be transmitted between electrodes in the end effector 12. A RF source (not shown), comprising, for example, an oscillator and an amplifier, among other components, which may supply the RF energy to the electrode, may be located in the instrument itself, such as in the handle 6 for a cordless instrument 10, or the RF source may be external to the instrument 10. The RF source may be activated as described further below.

According to various embodiments, the end effector 12 may comprise multiple sections (or segments) of electrodes. For example, as shown in the example of FIG. 23, the lower surface of the anvil 24 (i.e., the surface facing the staple cartridge 34) may comprise three co-linear RF segments. In this example, each segment has the same length (e.g., 20 mm), although in other embodiments there may be more or fewer segments, and the segments may have different lengths. In the example of FIG. 23, there are three pairs of active or "anode" terminals or electrodes 500 lined up longitudinally along each side of the channel length on the lower surface of the anvil 24. In particular, in the illustrated embodiment there is a pair of distal electrodes $500_1$, a pair of middle electrodes $500_2$, and a pair of proximate electrodes $500_3$ on each side of the knife channel 516. The metallic outer portion or channel 22 of the end effector 12 or the metallic anvil 24 may serve as the counter-electrode (or cathode) for each of the three upper active electrodes (or anodes) 500. The upper electrodes 500 may be coupled to the RF source. When energized, RF energy may propagate between the upper electrodes 500 and the counter electrode, coagulating tissue clamped between the electrodes.

The electrodes 500 may be energized simultaneously or in various orders, such as sequentially. For embodiments where the electrodes 500 are energized according to a sequence, the sequence may be automatic (controlled, for example, by a controller (not shown) in communication with the RF source)

or by selection by the user. For example, the proximate electrodes $500_3$ could be energized first; then the middle electrodes $500_2$; then the distal electrodes $500_1$. That way, the operator (e.g., the operating surgeon) can selectively coagulate areas of the staple line. The electrodes in such an embodiment could be controlled by a multiplexer and/or a multiple output generator, as described further below. That way, the tissue under each electrode 500 could be treated individually according to the coagulation needs. Each electrode in the pair may be connected to the RF source so that they are energized at the same time. That is, for the distal pair of active electrodes $500_1$, each, being on opposite sides of the knife channel, may be energized by the RF source at the same time. Same for the middle pair of electrodes $500_2$ and the proximate pair of electrodes $500_3$, although, in an embodiment where the electrode pairs are energized in sequence, the distal pair is not energized at the same time as the middle and proximate pairs, and so on.

Further, various electrical parameters, such as impedance, delivered power or energy, etc., could be monitored and the output to particular electrodes 500 could be modified to produce the most desirable tissue effect. Additionally, another advantage is in the case of a metal staple or other electrically conductive object left from a previous instrument firing or surgical procedure that may cause a short of the electrodes. Such a short situation could be detected by the generator and/or multiplexer, and the energy could be modulated in a manner appropriate for the short circuit.

In addition, energizing the electrodes 500 in sequence reduces the instantaneous power required from the RF source in comparison to a design that would has one set of electrodes as long as the combined length of the three segmented electrodes 500 shown in FIG. 23. For example, for electrode configurations as shown in the '312 patent, it has been demonstrated that it would require fifty to one-hundred watts to coagulate successfully forty-five mm lines on either side of the cut line. By using smaller active electrodes (e.g., the upper electrodes 500) that have less surface area than the larger return electrodes (e.g., the metallic anvil 24), the smaller active electrodes 500 can concentrate the therapeutic energy at the tissue while the larger, return electrode is used to complete the circuit with minimal impact on the tissue interface. In addition, the return electrode preferably has greater mass and thereby is able to stay cooler during electrosurgical application.

The electrodes 500 may be surrounded by an electrically insulating material 504, which may comprise a ceramic material.

FIG. 24 shows another embodiment having segmented RF electrodes. In the embodiment shown in FIG. 24, there are four co-linear segmented electrodes $500_{1-4}$ of equal length (15 mm in this example). Like the embodiment of FIG. 23, the electrodes 500 of FIG. 24 could be energized simultaneously or sequentially.

Figure 25:
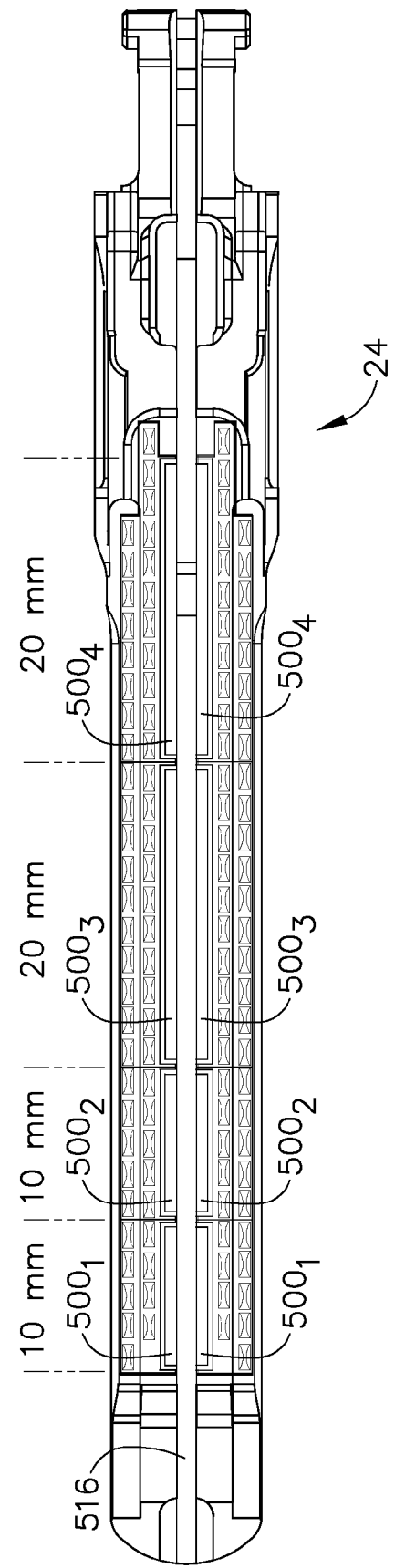

FIG. 25 shows yet another embodiment, in which the segmented electrodes have different lengths. In the illustrated embodiment, there are four co-linear segmented electrodes, but the most distal electrodes $500_1$, $500_2$ are 10 mm in length, and the two proximate electrodes $500_3$, $500_4$ are 20 mm in length. Having short distal electrodes may provide the advantage of concentrating the therapeutic energy, as mentioned above.

Figure 59:
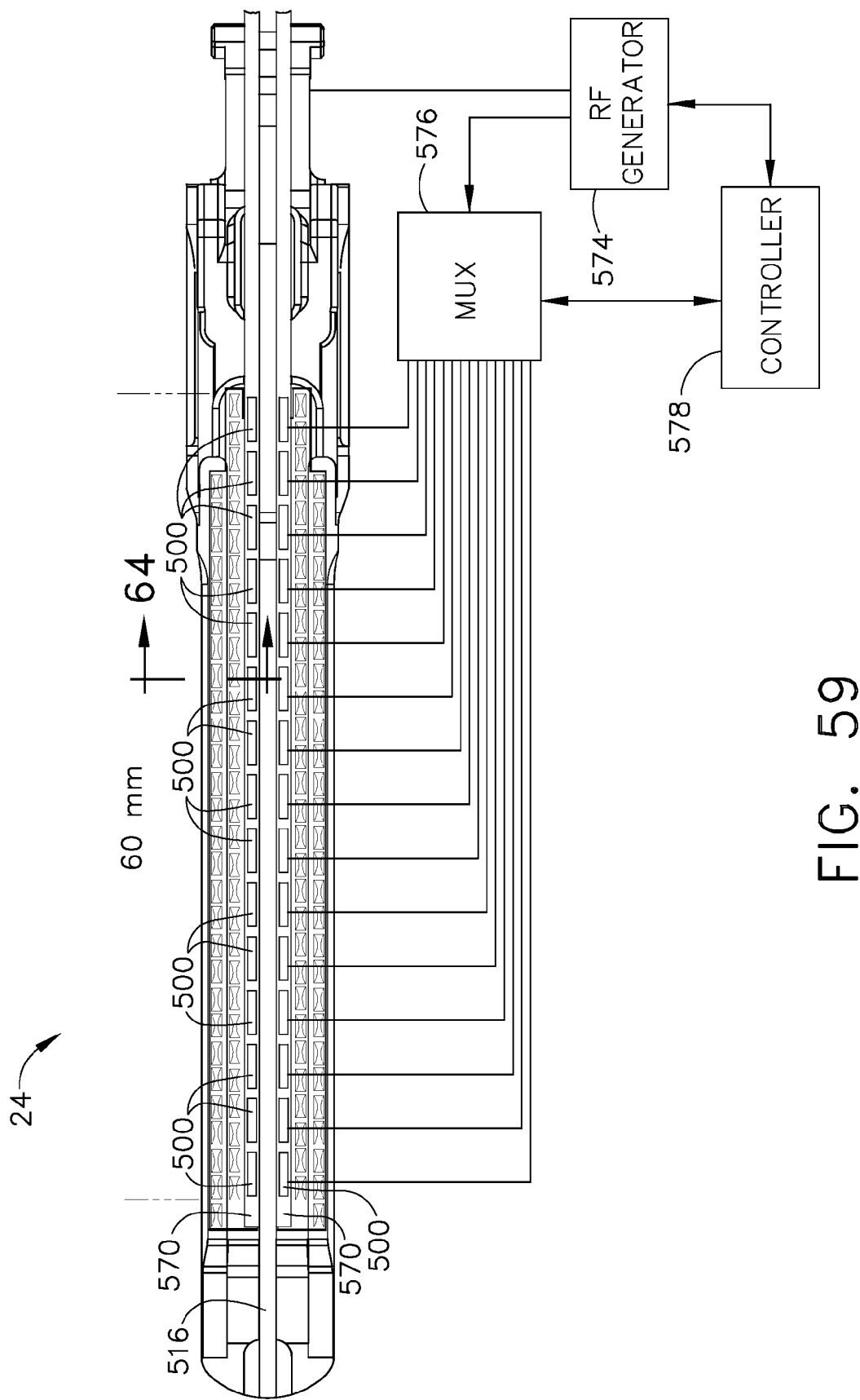

FIG. 59 shows an embodiment having fifteen pairs of segmented RF electrodes 500 on a circuit board 570, or other type of suitable substrate, on the lower surface of the anvil 24 (i.e., the surface facing the channel 22). The various electrode pairs are energized by the RF source (or generator) 574. The multiplexer 576 may distribute the RF energy to the various electrode pairs as desired under the control of a controller 578. According to various embodiments, the RF source 574, the multiplexer 576, and the controller 578 may be located in the handle 6 of the instrument.

Figure 60:
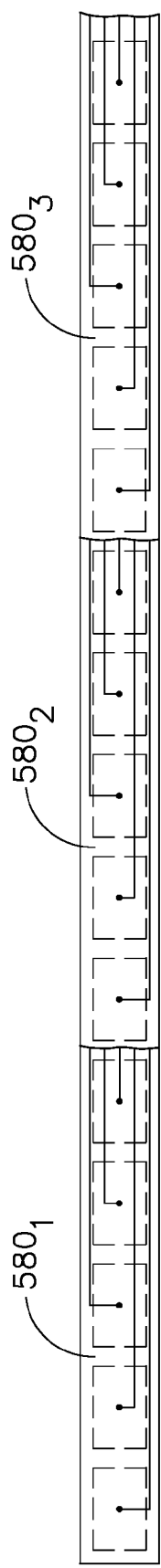
Figure 61:
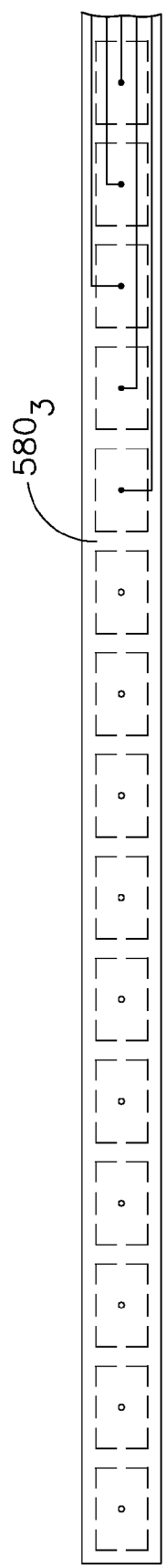
Figure 62:
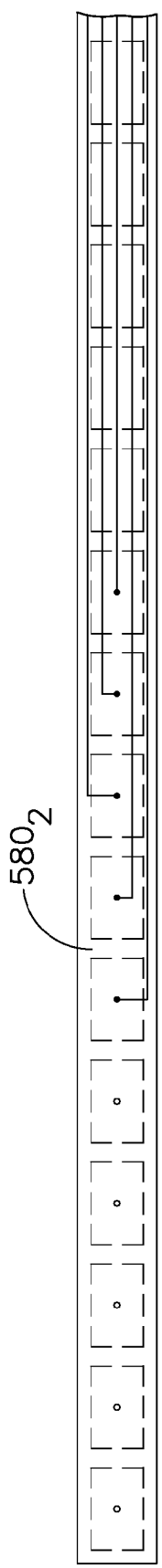
Figure 63:
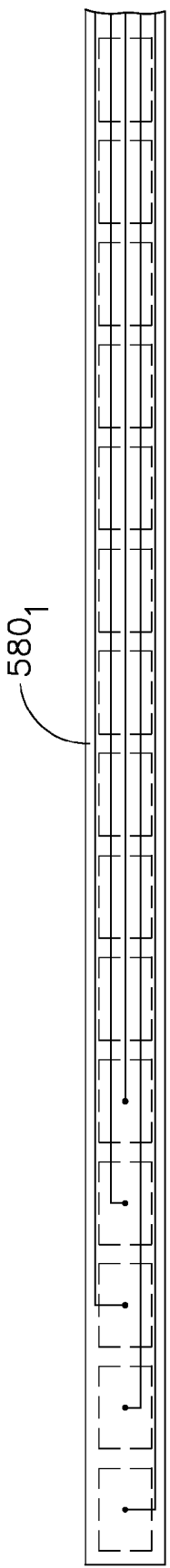

In such an embodiment, the circuit board 570 may comprise multiple layers that provide electrical connections between the multiplexer 576 and the various electrode pairs. For example, as shown in FIGS. 60 to 63, the circuit board may comprise three layers $580_{1-3}$, each layer 580 providing connections to five of the electrode pairs. For example, the upper most layer $580_3$ may provide connections to the most proximate five electrode pairs, as shown in FIGS. 60 and 61; the middle layer $580_2$ may provide connections to the middle five electrode pairs, as shown in FIGS. 60 and 62; and the lowest layer $580_1$ may provide connections to the most distal five electrode pairs, as shown in FIGS. 60 and 63.

Figure 64:
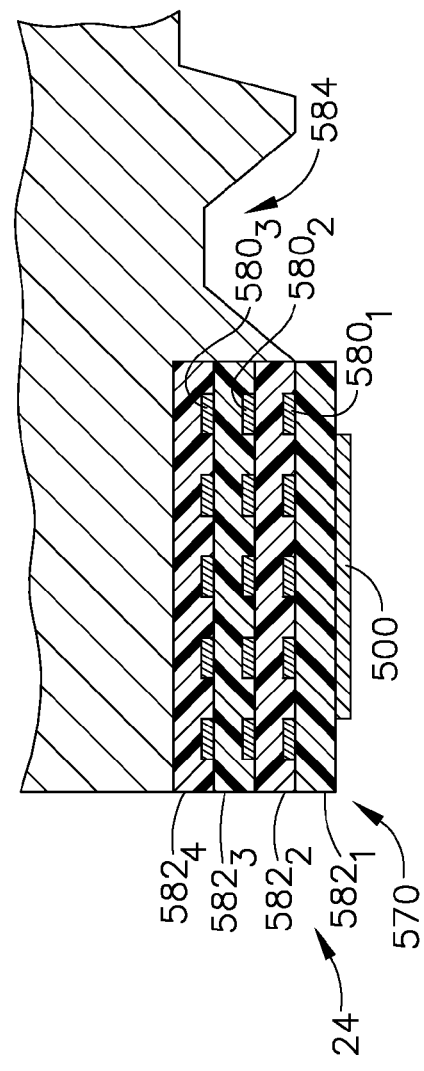
Figure 65:
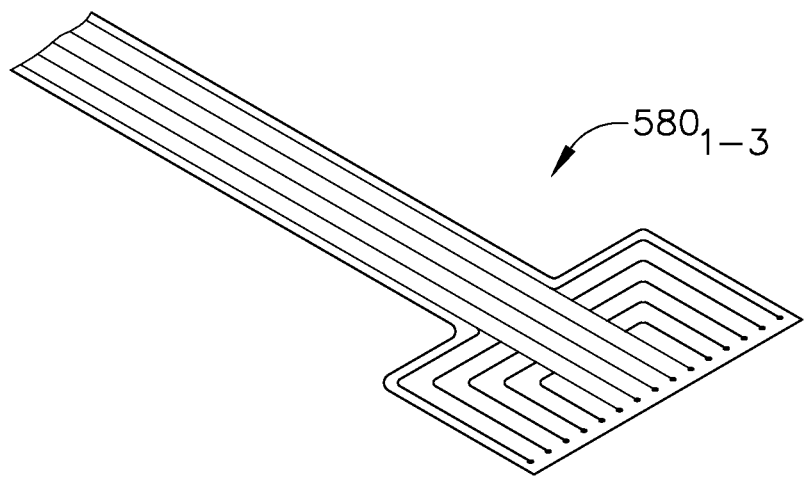
Figure 66:
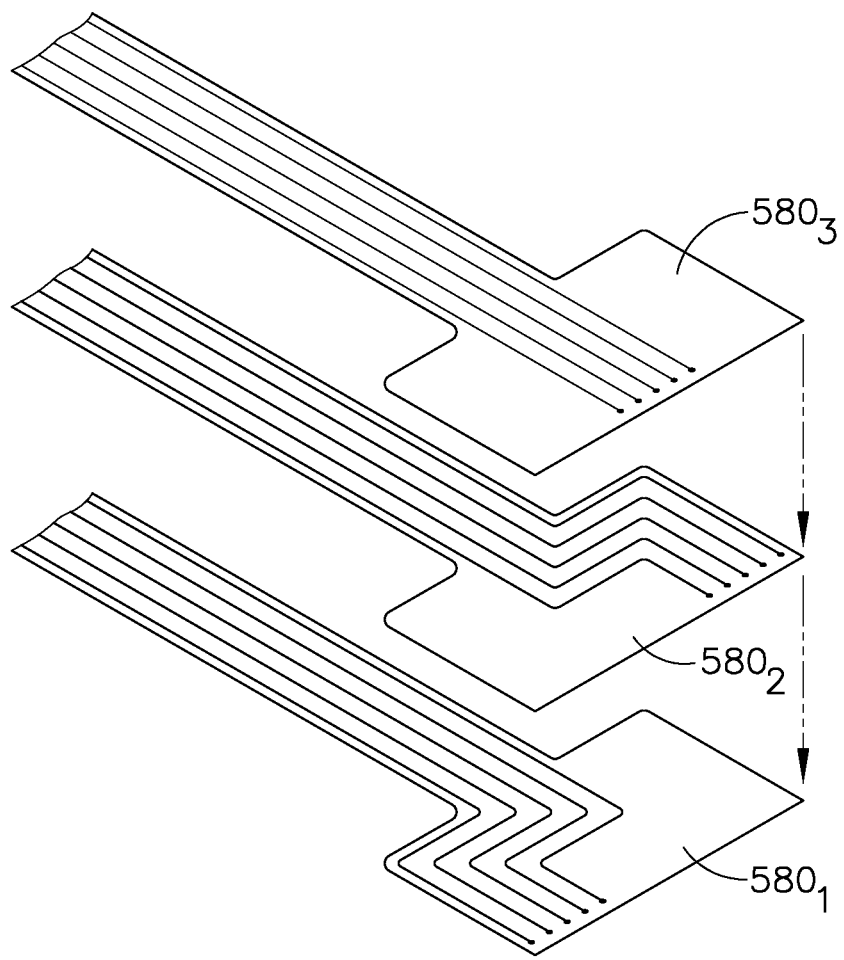

FIG. 64 shows a cross-sectional end view of the anvil 24 according to such an embodiment. The circuit board 570, adjacent to the staple pockets 584, comprises three conducting layers $580_{1-3}$, having insulating layers $582_{1-4}$ therebetween. FIGS. 65 and 66 show how the various layers $580_{1-3}$ may be stacked to connect back to the multiplexer 576 in the handle.

An advantage of having so many RF electrodes in the end effector 12, as shown in FIG. 67, is that, in the case of a metal staple line 590 or other electrically conductive object left in the tissue 592 from a previous instrument firing or surgical procedure that may cause a short of the electrodes, such a short situation could be detected by the generator and multiplexer, and the energy could be modulated in a manner appropriate for the short circuit.

Figure 27:
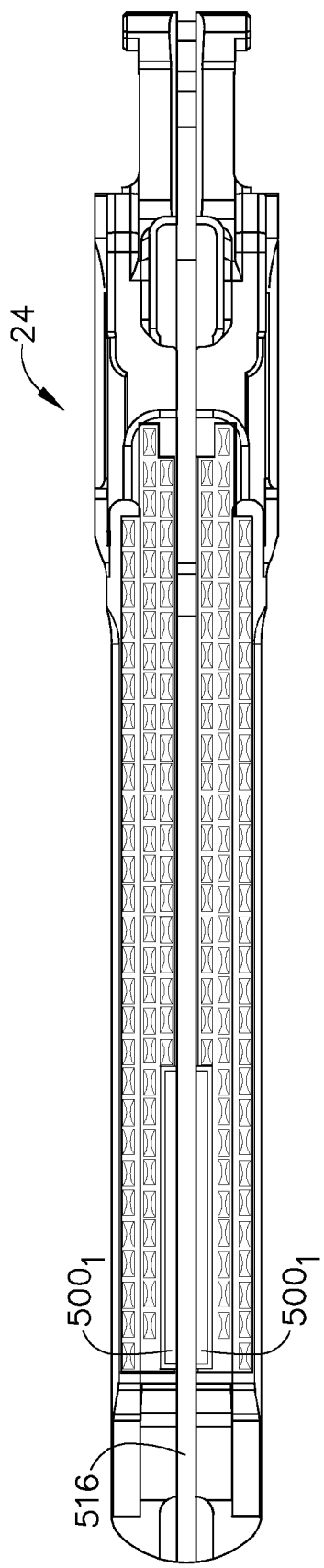

FIG. 27 shows another end effector 12 with RF electrodes. In this embodiment, the end effector 12 only comprises distal electrodes $500_1$, with the metallic anvil 24 serving as the return electrode. The distal electrodes $500_1$ do not span the entire length of the anvil 24, but only a fraction of the length. In the illustrated embodiment, distal electrodes $500_1$ are only approximately 20 mm in length along a 60 mm anvil, so that the distal electrodes $500_1$ only cover approximately the most distal ⅓ of the anvil length. In other embodiments, the distal electrodes $500_1$ could cover the most distal 1/10 to ½ of the anvil length. Such embodiments could be used for spot coagulation, as described in U.S. Pat. No. 5,599,350, which is incorporated herein by reference.

Figure 28:
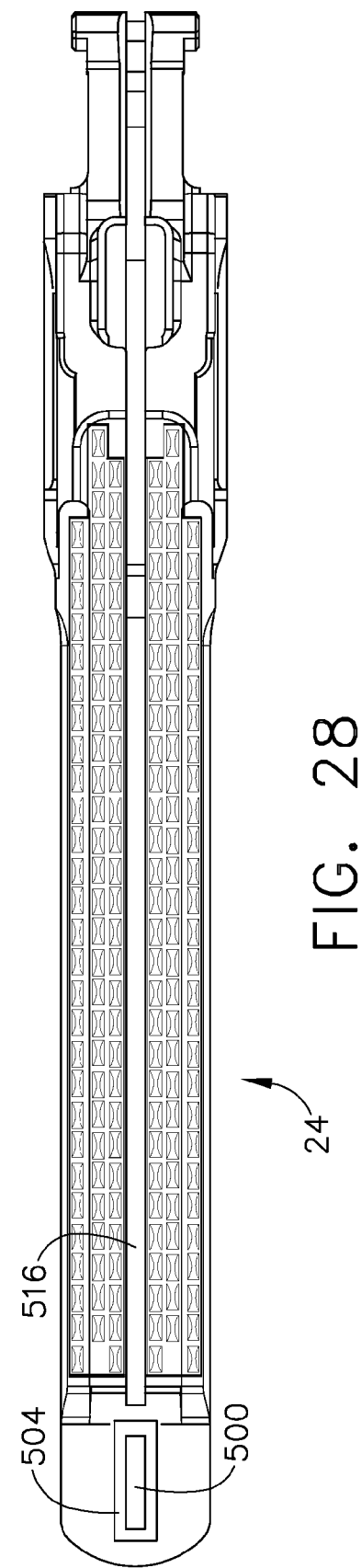

FIG. 28 shows yet another embodiment of the end effector 12 with RF electrodes. In this embodiment, an active electrode 500 is positioned at the distal tip of the anvil 24, insulated by the anvil 24 by an electrically non-conductive insulator 504, which may be made of ceramic material. Such an embodiment may be used for spot coagulation.

Figure 29:
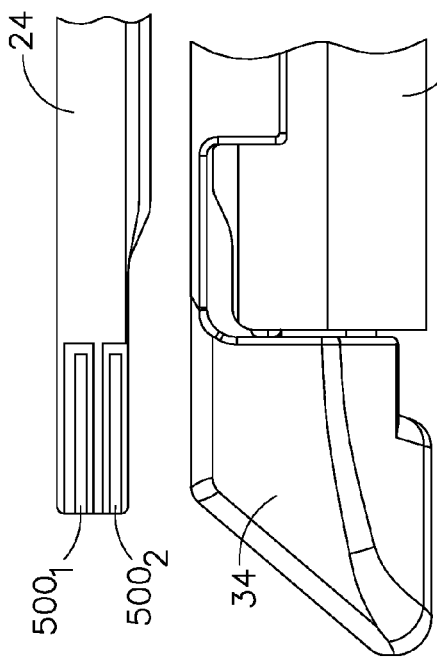
Figure 30:
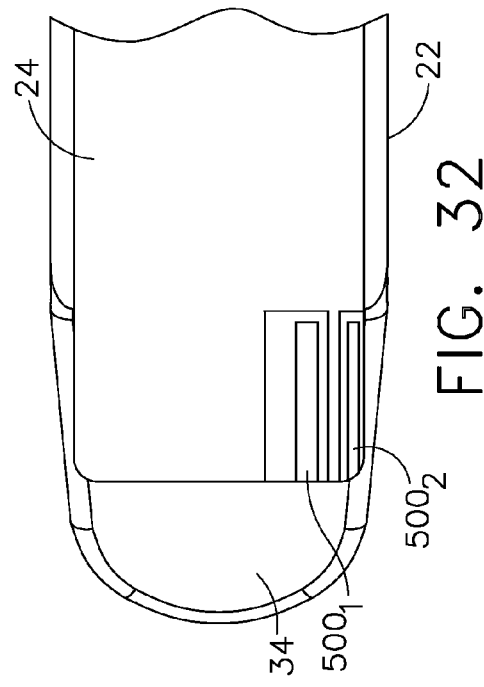
Figure 31:
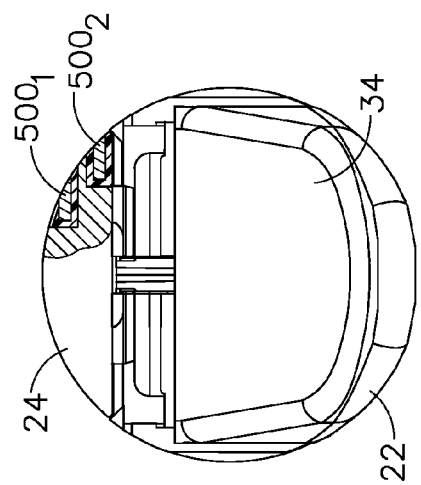
Figure 32:
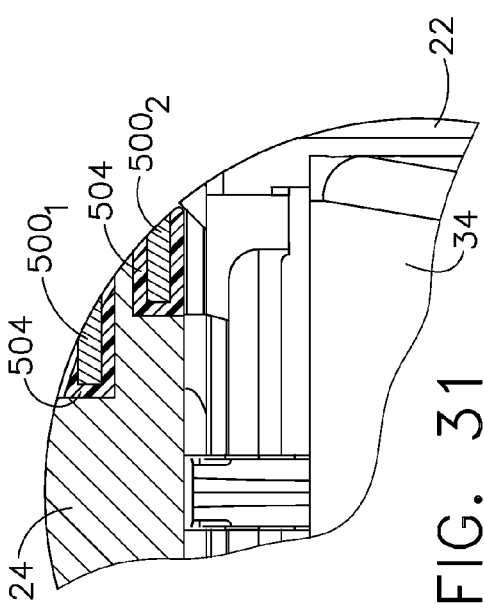
Figure 37:
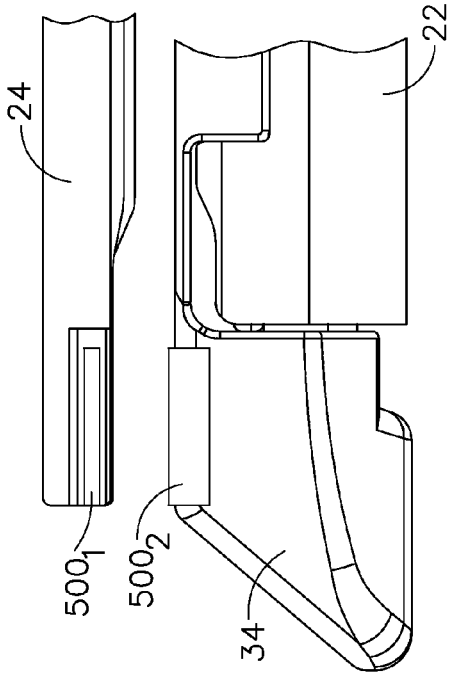
Figure 38:
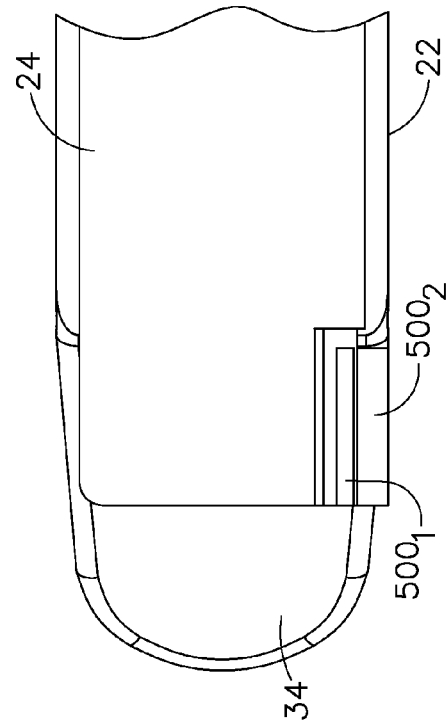
Figure 39:
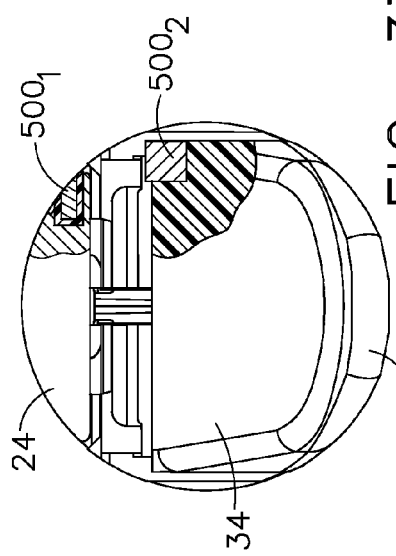
Figure 40:
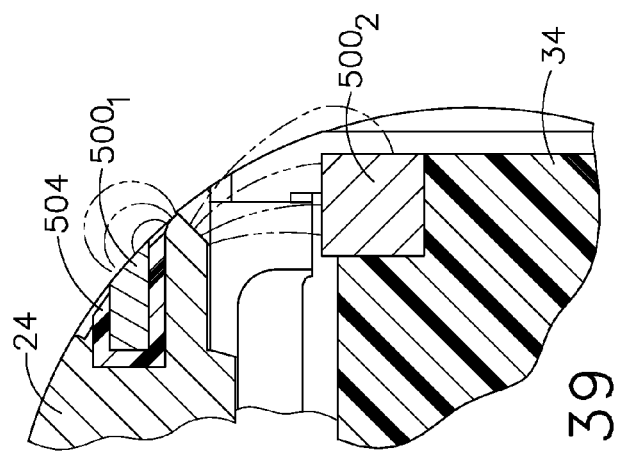
Figure 42:
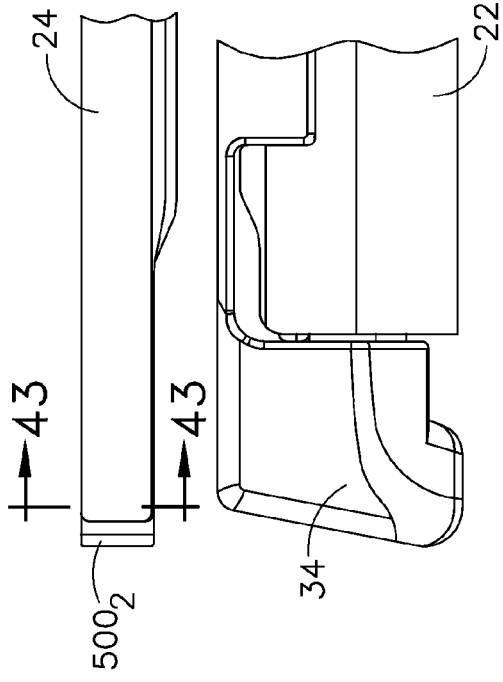
Figure 44:
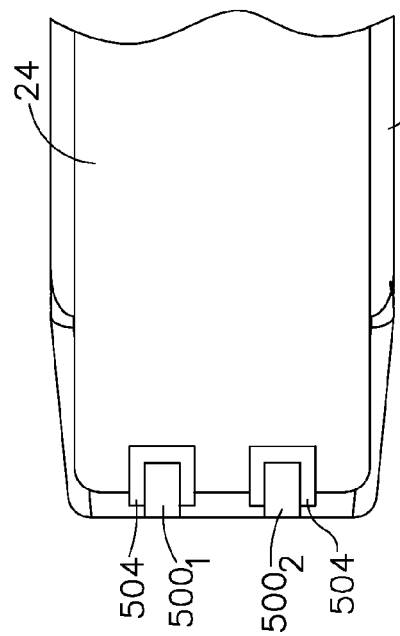
Figure 41:
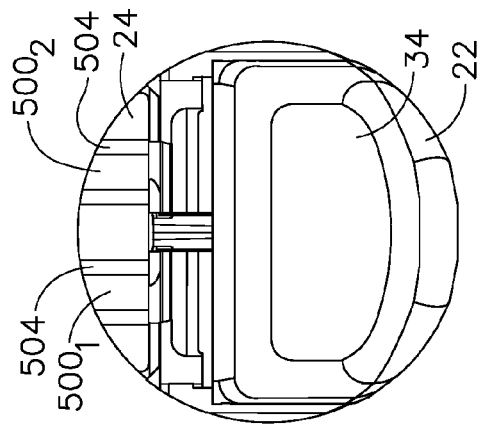
Figure 43:
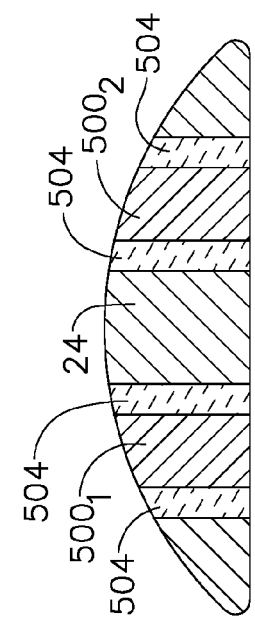
Figure 46:
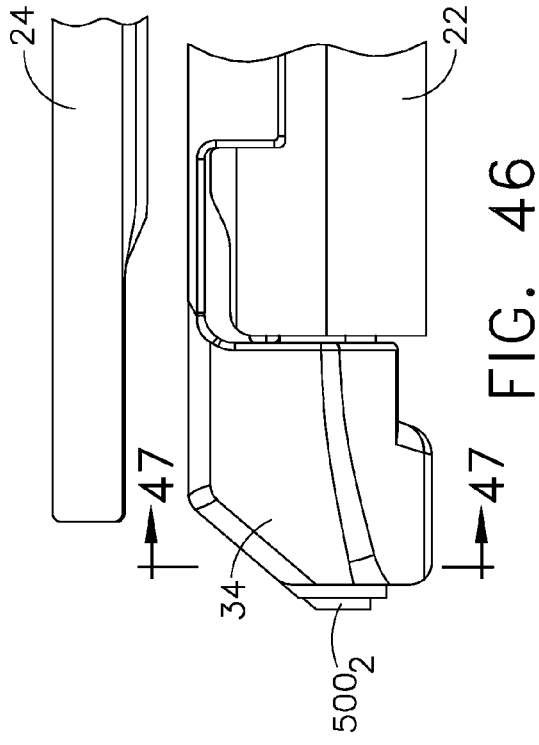
Figure 48:
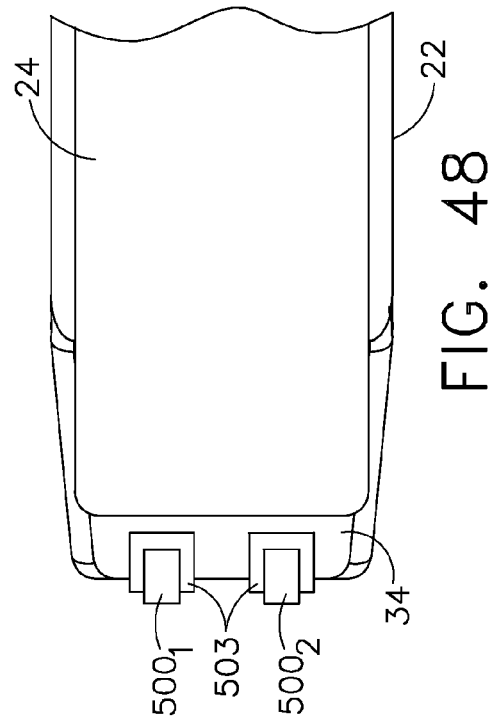
Figure 45:
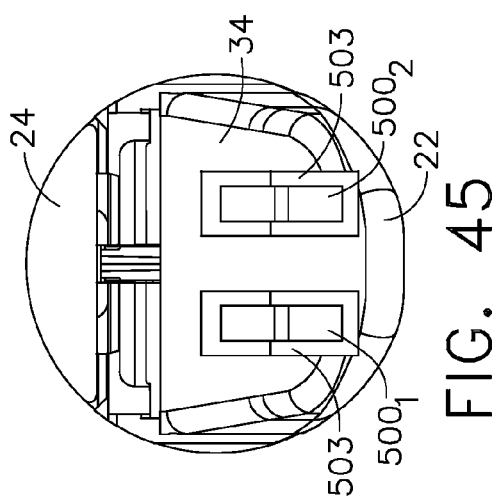
Figure 47:
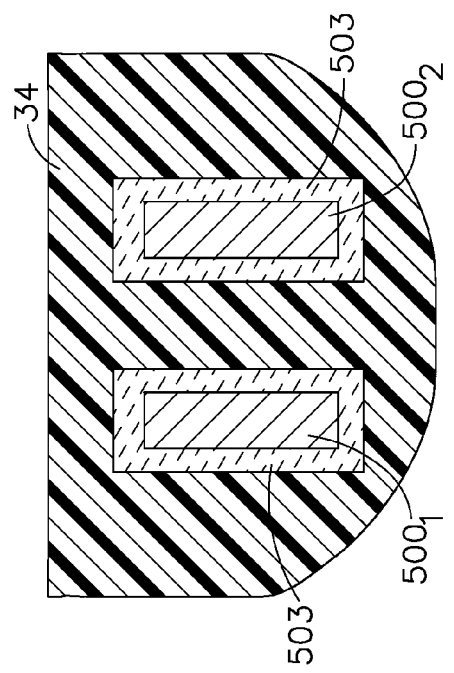

FIGS. 29 to 32 illustrate other embodiments of the end effector 12 that may be useful for spot coagulation. In these embodiments, the anvil 24 comprises a pair of electrodes $500_1$, $500_2$ at the distal end of the anvil 24 and along a lateral side of the anvil 24. FIG. 29 is front-end view of the anvil 24 according to such an embodiment, FIG. 30 is a side view, FIG. 31 is an enlarged fragmentary front-end view, and FIG. 32 is a top view. In such an embodiment, the metallic anvil 24 may act as the return electrode. The active electrodes $500_1$, $500_2$ may be insulated from the anvil 24 by electrically non-conductive insulators 504, which may comprise ceramic material.

FIGS. 33 to 36 show an embodiment where the anvil 24 comprises two distal electrodes $500_1$, $500_2$ located at the top, center of the anvil 24. Again, the metallic anvil 24 may act as the return electrode, and the active electrodes $500_1$, $500_2$ may be insulated from the anvil 24 by electrically non-conductive insulators 504.

FIGS. 37 to 40 show an embodiment where one active electrode $500_1$ (e.g., the active electrode) is positioned on the anvil 24, and another active electrode $500_2$ is positioned on the lower jaw 22, and preferably on the cartridge 34. The metallic anvil 24 may serve as the return electrode. The anvil electrode $500_1$ is insulated from the anvil 24 by an insulator 504. The electrode $500_2$, being positioned in the cartridge 34, which is preferably made from a non-conductive material such as plastic, is insulated from the metallic channel 22 by the cartridge 34.

FIGS. 41 to 44 show an embodiment where the anvil 24 has two active electrodes $500_1$, $500_2$ at the very most distal end of the anvil 24 that extend completely from the upper surface of the anvil 24 to the lower surface. Again, the metallic anvil 24 may act as the return electrode, and the active electrodes $500_1$, $500_2$ may be insulated from the anvil 24 by electrically non-conductive insulators 504.

FIGS. 45 to 48 show an embodiment where the cartridge 34 has two active electrodes $500_1$, $500_2$ at the very most distal end of the staple cartridge 34. In such an embodiment, the metallic anvil 24 or the metallic channel 22 may act as the return electrode. In this illustrated embodiment, the electrodes $500_1$, $500_2$ are connected to insulator inserts 503, but in other embodiments, the insulator inserts 503 could be omitted and the plastic cartridge 34 may serve as the insulator for the electrodes $500_1$, $500_2$.

FIGS. 49 to 52 show an embodiment having one active electrode $500_1$ at the very most distal end of the anvil 24 and another active electrode $500_2$ at the very most distal end of the cartridge 34. Again, in such an embodiment, the metallic anvil 24 or the metallic channel 22 may act as the return electrode. In this illustrated embodiment, the electrode $500_2$ is connected to insulator inserts 503, 505, but in other embodiments, the insulator inserts 503, 505 could be omitted and the plastic cartridge 34 may serve as the insulator for the electrode $500_2$.

FIG. 57 is a side view and FIG. 58 is a cross-sectional side of the handle 6 according to other embodiments of the present invention. The illustrated embodiment only includes one trigger, the closure trigger 18. Activation of the knife, staple drivers, and/or RF electrodes in this embodiment may be achieved through means other than a separate firing trigger. For example, as shown in FIG. 57, actuation of the knife, staple drivers, and/or RF electrodes may be activated by a push-button switch 540 or other type of switch that is in a position that is convenient for the operator. In FIG. 57, the switch 540 is shown at the most proximate portion of the handle 6. In another embodiment, the switch may be positioned near the distal end of the handle 6 so that pulling of the nozzle 539 activates the switch to cause actuation of the instrument. In such an embodiment, a switch (not shown) may be placed under or near the nozzle 539 so that movement of the nozzles toggles the switch.

Alternatively, actuation of the knife, staple drivers, and/or RF electrodes may be activated by voice or other sound commands detected by a microphone 542. In other embodiments, the handle 6 may comprise a RF or sonic transceiver 541, which may receive and/or transmit RF or sonic signals to activate the instrument. Also, as shown in FIG. 58, a foot pedal or switch 544 could be used to active the instrument 10. The foot pedal 544 may be connected to the handle 6 by a cord 545. Also, the handle 6 may comprise a dial control 546 or some other suitable control device for controlling actuation of the segmented RF electrodes (see, for example, FIGS. 23 and 24). Using such a control device 546, the operator may serially activate the various pairs of RF electrodes 500 in the end effector 12.

The instrument 10 shown in FIGS. 57 and 58 also includes many feedback systems for the user. As mentioned above, the instrument 10 may comprise the speaker 543 for audibleizing commands or instructions to the operator. In addition, the handle 6 may comprise visual indicators 548, such as LEDs or other light sources that provide visual feedback regarding actuation of the various segmented RF electrodes. For example, each of the visual indicators 548 could correspond to one of the segmented RF electrode pairs. The corresponding visual indicator 548 may be activated when the segmented RF electrode pair is activated. In addition, the handle 6 may comprise an alphanumeric display 550, which may be an LED or LCD display, for example. The display 550 may be connected to a circuit board 552 inside the handle 6. The handle 6 may also comprise a vibrator 554 in the pistol grip portion 26 that may provide vibrational feedback to the operator. For example, the vibrator 554 could vibrate each time that one of the segmented pairs of the RF electrodes in the end effector 12 is activated.

Figure 26:
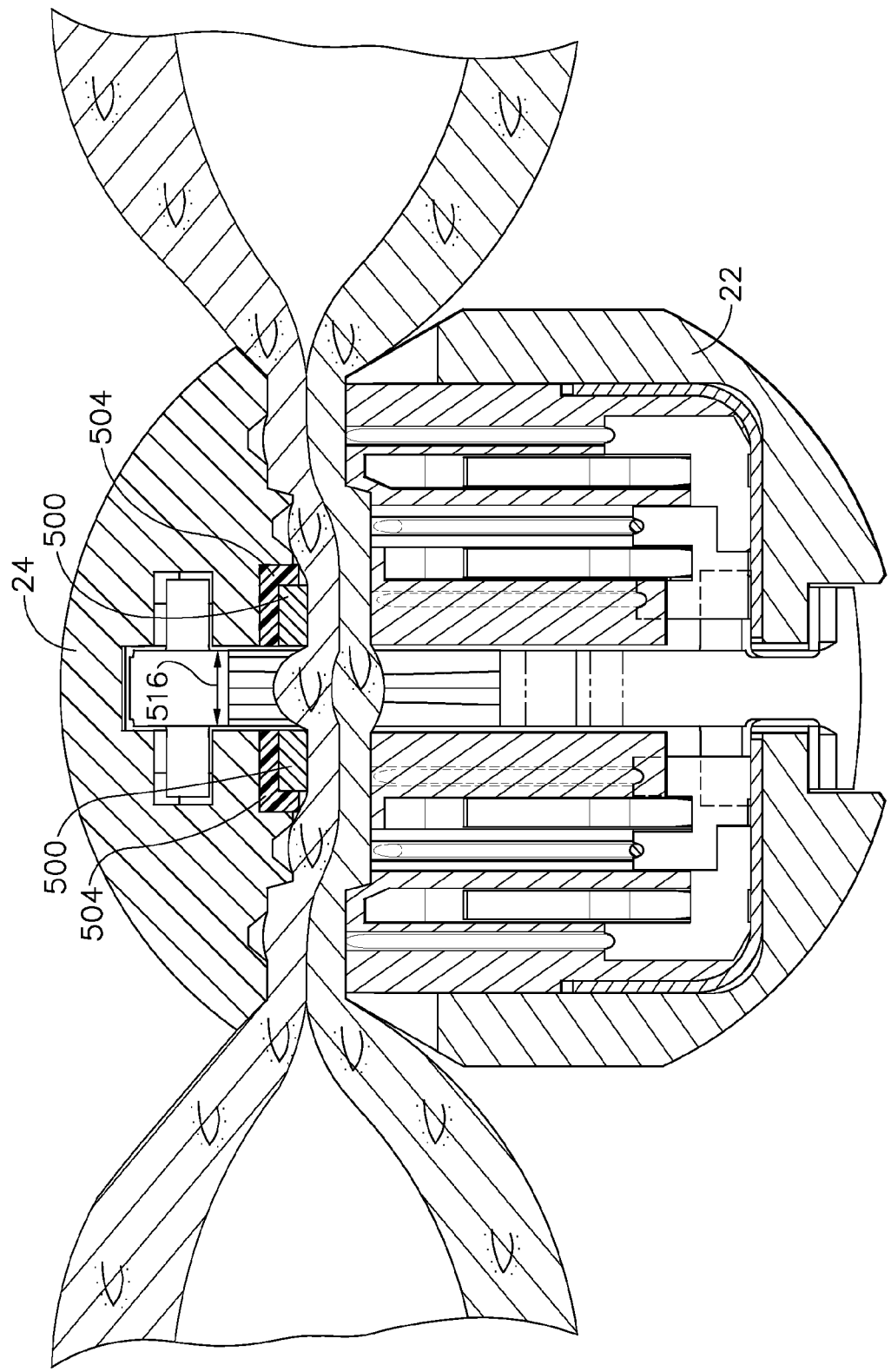
Figure 68:
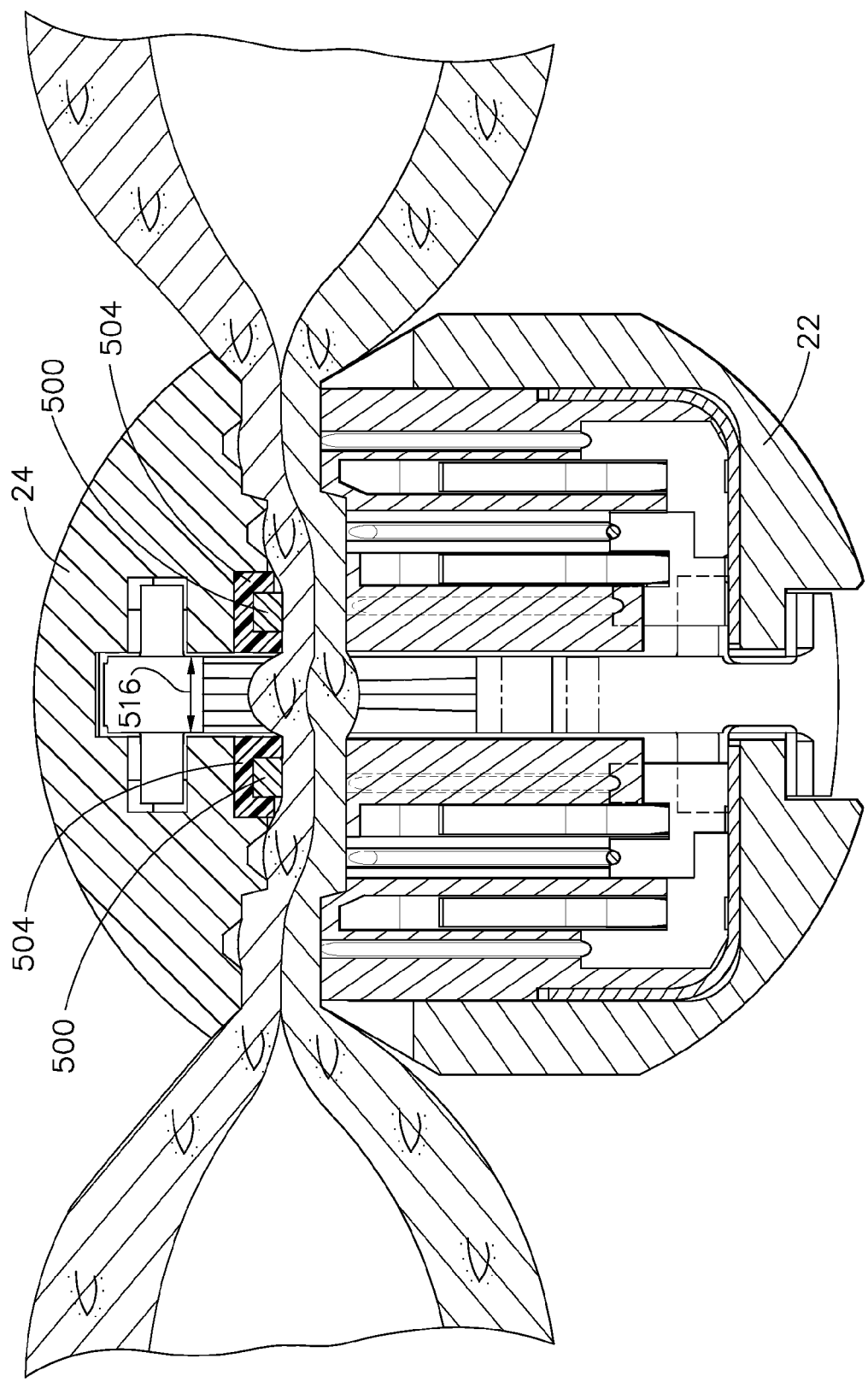

FIG. 26 is a cross-sectional view of the end effector 12 according to various embodiments where the electrodes are on the upper jaw (or anvil) 24. In the illustrated embodiment, the active electrodes 500 are positioned adjacent the knife slot 516. The metal anvil 24 may serve as the return electrode. Insulators 504, which may be made of ceramic, insulate the electrodes 500 from the metallic anvil 24. The embodiment of FIG. 68 is similar to that of FIG. 26, except that electrodes 500 are made smaller, such that a portion of the insulators 504 can extend between the respective electrodes 500 and the edges of the knife channel 516.

Figure 53:
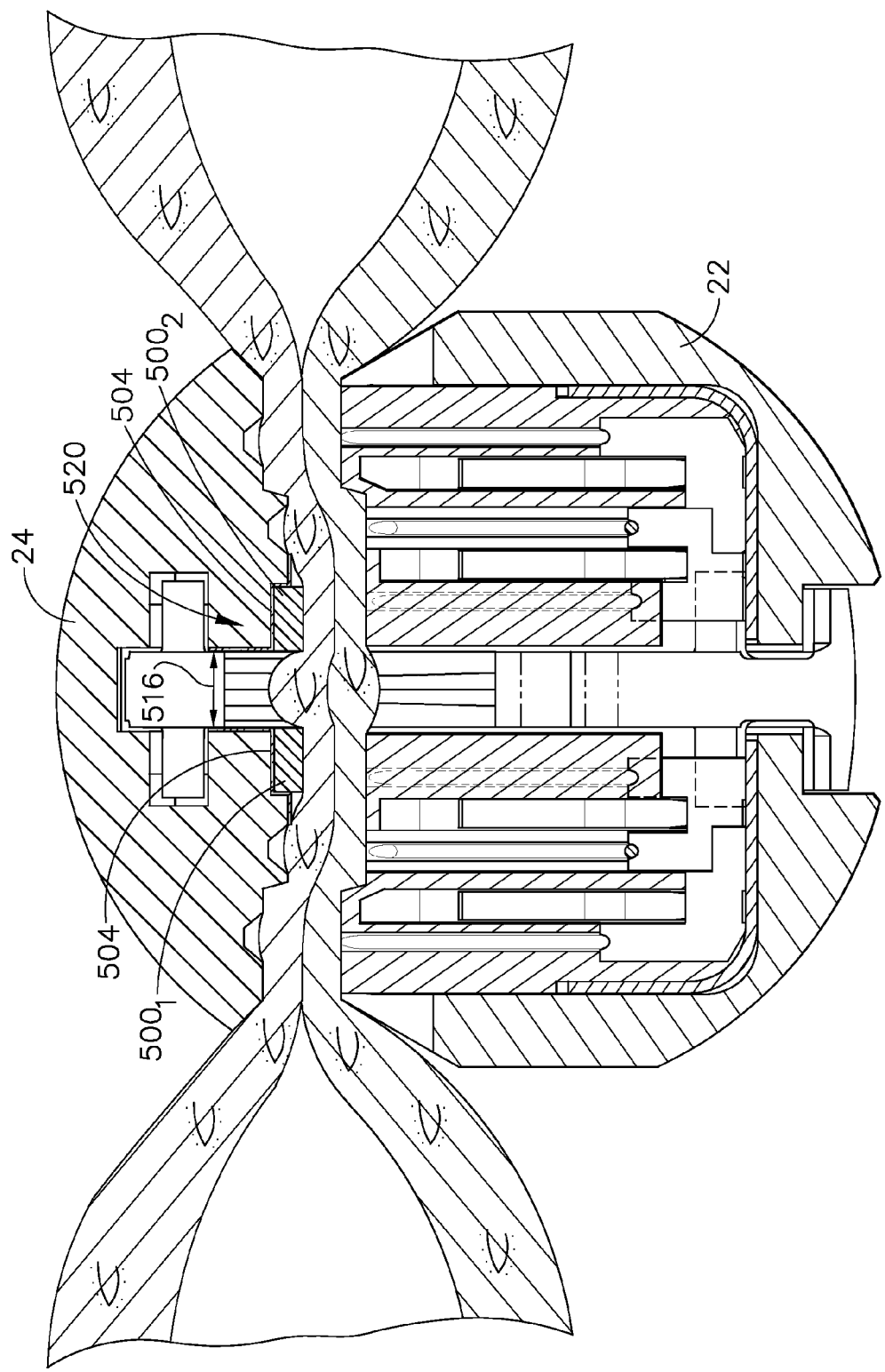

FIG. 53 is a cross-sectional end view of the end effector 12 according to another embodiment. In this embodiment, like the embodiment of FIG. 26, the active electrodes $500_1$, $500_2$ are on the anvil 24 on opposite sides of the knife channel. The electrodes $500_1$, $500_2$ are insulated from the metallic anvil by insulators 504, which again preferably comprise ceramic material. In this embodiment, however, the insulators 504 are made very thin (compare with FIG. 26). Making the insulators 504 very thin provides the potential advantage that the anvil 24 may include a relatively large metal section 520 above the electrodes 500, thereby potentially supporting a slimmer anvil profile for a given anvil stiffness, or a stiffer profile for a given anvil cross-sectional dimension. The insulators 504 may be cast in or sputter coated onto the anvil 24.

Figure 54:
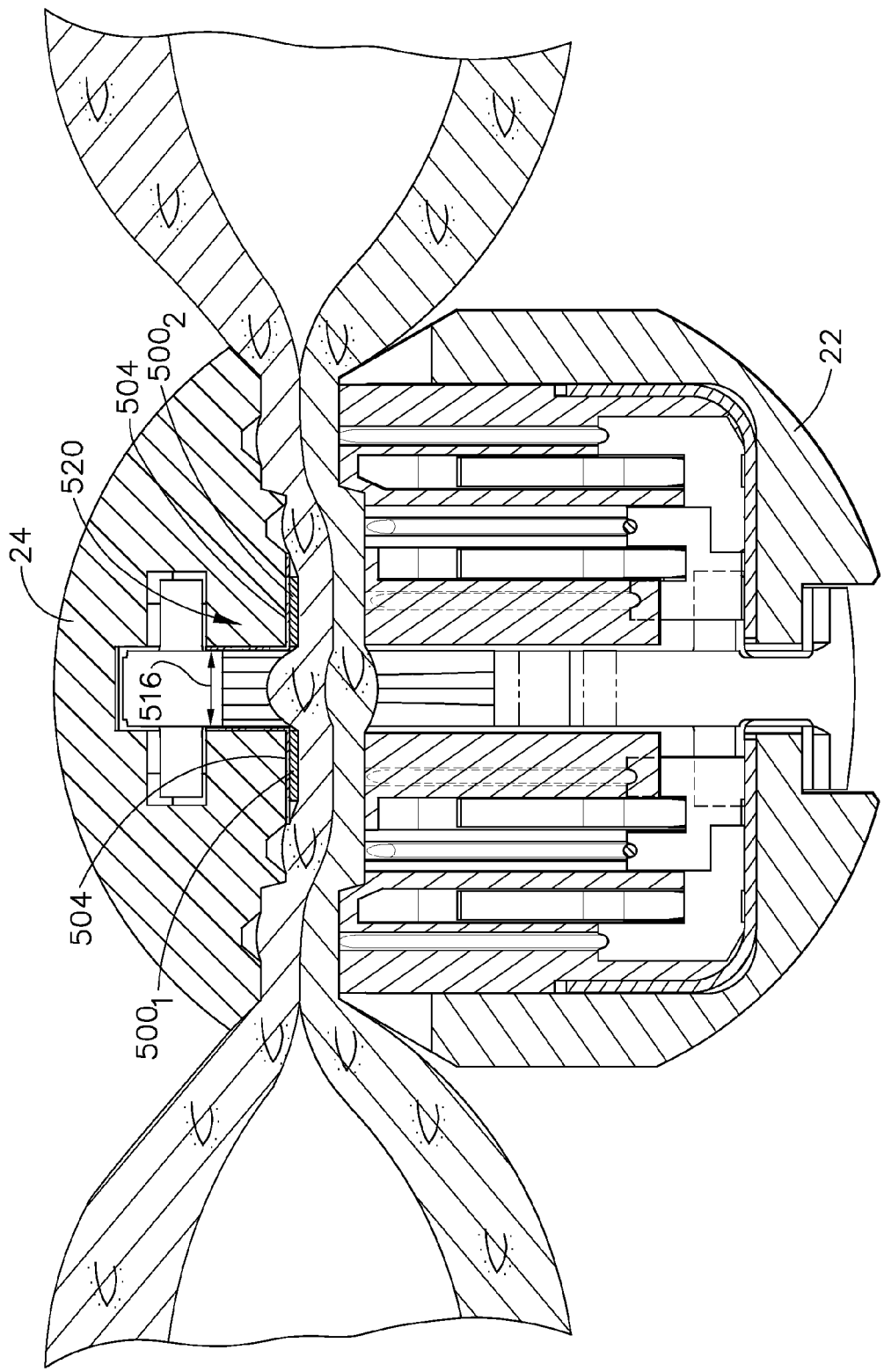

FIG. 54 illustrates another embodiment. In this embodiment, the active electrodes $500_1$, $500_2$ are sputter coated or bonded to the insulators 504, which may also be sputter coated or bonded to the anvil 24. Like the embodiment of FIG. 53, this design allows for more anvil material above the electrodes. In such an embodiment, the electrodes $500_1$, $500_2$ may comprise silver, which is a good conductor of electricity and has antimicrobial properties.

FIG. 55 shows a side view of the end effector according to another embodiment. In this embodiment, a thin film of electrically insulating material 530 is deposited on the face of the cartridge 34. The insulating film 530 preferably comprises a heat- and arc-resistant material, such as ceramic. This would tend to increase the resistance of the cartridge 34 to arc-tracking and shorting, permitting more firings between changes of the cartridge 34. In addition, if the cartridge 34 was a poor electrical conductor, it would support quicker heating of tissue and reduce the overall energy requirements. The active electrodes (not shown in FIG. 55) may be in the anvil 24, as described in embodiments above.

FIG. 56 shows an embodiment that is similar to that shown in FIG. 55, except that in FIG. 56, a thin layer 532 of slightly electrically conductive material is deposited on top of the insulating film 530. The conductivity of the thin, slightly conductive layer 532 may be lower than the conductive of the tissue clamped in the end effector 12 for treatment. As such, the thin, slightly conductive layer 532 would provide a reduced-conductivity path to provide additional heating of the clamped tissue. This would tend to reduce the time required to heat the tissue and achieve coagulation.

As described above, the instrument 10 may comprise an articulation pivot 14 for articulating the end effector 12. A clinician or operator of the instrument 10 may articulate the end effector 12 relative to the shaft 8 by utilizing the articulation control 16, as described in more detail in published U.S. patent application Pub. No. 2007/0158385 A1, entitled "Surgical Instrument Having An Articulating End Effector," by Geoffrey C. Hueil et al., which is incorporated herein by reference. In other embodiment, rather than a control device that is integrated with the instrument 10, the end effector 12 may be articulated by a separate instrument, such as gripper, that is inserted into the patient so that its operative portion is near the end effector 12 so that it can articulate the end effector 12 as desired. The separate instrument may be inserted through a different opening as the end effector 12, or through the same opening. Also, different operators can operate the separate instruments, or one person can operate both instruments, to articulate the end effector 12. In another passive articulation scenario, the end effector 12 may be articulated by carefully pushing it against other parts of the patient to achieve the desired articulation.

In another embodiment, the end effector 12 may be connected to the handle by a flexible cable. In such an embodiment, the end effector 12 could be positioned as desired and held in position by use of another instrument, e.g., a separate gripper instrument. In addition, in other embodiments, the end effector 12 could be positioned by a separate instrument and clamped by a second separate instrument. In addition, the end effector 12 could be made sufficiently small, such as 8 to 9 mm wide by 10 to 11 mm tall, so that a pull-to-close mechanism could be used to clamp the end effector from the handle 6. The pull-to-close mechanism could be adapted from that described in U.S. Pat. No. 5,562,701, entitled "Cable-Actuated Jaw Assembly For Surgical Instruments," which is incorporated herein by reference. The cable 600 could be disposed in or along a flexible endoscope for use, for example, in upper or lower gastro-intestinal tract procedures.

In yet another embodiment, as shown in FIGS. 69 and 70, the instrument 10 may comprise a flexible neck assembly 732 enabling articulation of the end effector 12. When an articulation transmission assembly 731 coupled to the shaft 8 is rotated, it may cause remote articulation of the flexible neck assembly 732. The flexible neck assembly 732 may comprise first and second flexible neck portions 733, 734, which receive first and second flexible band assemblies 735, 736. Upon rotation of the articulation transmission assembly 731, one of the first and second flexible transmission band assemblies 735, 736 is moved forwardly and the other band assembly is moved rearwardly. In response to the reciprocating movement of the band assemblies within the first and second flexible neck portions 733, 734 of the flexible neck assembly 732, the flexible neck assembly 732 bends to provide articulation. A further description of the flexible neck is described in U.S. Pat. No. 5,704,534, which is incorporated herein by reference.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the various embodiments of the invention described herein will be processed before surgery. First, a new or used instrument is obtained and if necessary cleaned. The instrument can then be sterilized. In one sterilization technique, the instrument is placed in a closed and sealed container, such as a thermoformed plastic shell covered with a sheet of TYVEK. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, steam and other methods.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. The various embodiments of the present invention represent vast improvements over prior staple methods that require the use of different sizes of staples in a single cartridge to achieve staples that have differing formed (final) heights.

Accordingly, the present invention has been discussed in terms of endoscopic procedures and apparatus. However, use herein of terms such as "endoscopic" should not be construed to limit the present invention to a surgical stapling and severing instrument for use only in conjunction with an endoscopic tube (i.e., trocar). On the contrary, it is believed that the present invention may find use in any procedure where access is limited, including but not limited to laparoscopic procedures, as well as open procedures. Moreover, the unique and novel aspects of the various staple cartridge embodiments of the present invention may find utility when used in connection with other forms of stapling apparatuses without departing from the spirit and scope of the present invention.

What is claimed is:

1. A surgical cutting and fastening instrument comprising:
   an end effector comprising:
      a cutting instrument for cutting tissue clamped in the end effector; and
      fastening means for fastening the tissue cut by the cutting instrument;
   a shaft connected to the end effector, the shaft comprising a drive train for powering the end effector;

an electric, DC motor connected to the drive train for powering the drive train; and a torque-limiting device connected between to an output pole of the motor and an input pole of the drive train.

2. The surgical cutting and fastening instrument of claim 1 further comprising a handle connected to the shaft, wherein the motor is located in the handle.

3. The surgical cutting and fastening instrument of claim 1, wherein the torque-limiting device comprises a clutch.

4. The surgical cutting and fastening instrument of claim 3, wherein the clutch comprises an electromagnetic clutch.

5. The surgical cutting and fastening instrument of claim 4, wherein the electromagnetic clutch comprises:

a horseshoe-shaped stator having a first magnetic disk at a first end of the stator and a second magnetic disk at a second end of the stator, wherein the first magnetic disk is connected to the output pole of the motor and the second magnetic disk is connected to the input pole of the drive train; and a coil, such that when the coil conducts a current, the electromagnetic flux from the coil actuates the clutch.

6. The surgical cutting and fastening instrument of claim 5, wherein:

when the coil conducts the current, the two magnetic disks are attracted to each other so that they come in contact; and when the coil is not conducting the current, the two magnetic disks are not in contact.

7. The surgical cutting and fastening instrument 6, wherein the coil is wrapped around the stator.

8. The surgical cutting and fastening instrument of claim 3, wherein the clutch comprises a permanent magnet.

9. The surgical cutting and fastening instrument of claim 8, wherein the clutch comprises a horseshoe-shaped stator having a first disk at a first end of the stator and a second disk at a second end of the stator, wherein the first disk is connected to the output pole of the motor and the second disk is connected to the input pole of the drive train, and wherein the permanent magnet is connected to the output pole of the motor and attracts the input pole of the drive train such that the magnetic disks are in contact.

10. The surgical cutting and fastening instrument of claim 1, wherein the end effector comprises:

upper and lower opposing jaws for clamping the tissue in the end effector; and wherein the cutting instrument comprises a knife that transverses for transversing a longitudinal channel of the lower jaw.

11. The surgical cutting and fastening instrument of claim 10, wherein the fastening means comprises at least one RF electrode.

12. The surgical cutting and fastening instrument of claim 1, wherein the torque-limiting device comprises a permanent magnet, horseshoe-shaped stator having a first disk at a first end of the stator and a second disk at a second end of the stator, wherein the first disk is connected to the output pole of the motor and the second disk is connected to the input pole of the drive train.

13. The surgical cutting and fastening instrument of claim 1, wherein the instrument is a linear endocutter.

14. The surgical cutting and fastening instrument of claim 1, wherein the instrument is a circular cutting and stapling device.

15. The surgical cutting and fastening instrument of claim 1, wherein the fastening means comprises a staple cartridge.

* * * * *

UNITED STATES PATENT AND TRADEMARK OFFICE
CERTIFICATE OF CORRECTION

| | | |
|---|---|---|
| PATENT NO. | : 8,459,525 B2 | Page 1 of 1 |
| APPLICATION NO. | : 12/031542 | |
| DATED | : June 11, 2013 | |
| INVENTOR(S) | : David C. Yates et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1503 days.

Signed and Sealed this
Sixth Day of January, 2015

Michelle K. Lee
*Deputy Director of the United States Patent and Trademark Office*